United States Patent
Rabovsky et al.

(10) Patent No.: US 11,207,388 B2
(45) Date of Patent: Dec. 28, 2021

(54) MULTI-SUPPLEMENT COMPOSITIONS

(71) Applicant: Melaleuca, Inc., Idaho Falls, ID (US)

(72) Inventors: Alexander B. Rabovsky, Idaho Falls, ID (US); Begonia Yeeman Ho, Idaho Falls, ID (US); Stephanie Y. Nielson, Idaho Falls, ID (US); Nasser A. Fredj, Idaho Falls, ID (US); Subhendu Nayak, Ammon, ID (US); Erin A. Stone, Ammons, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 14/987,584

(22) Filed: Jan. 4, 2016

(65) Prior Publication Data

US 2016/0193306 A1 Jul. 7, 2016

Related U.S. Application Data

(60) Provisional application No. 62/099,428, filed on Jan. 2, 2015, provisional application No. 62/099,410, filed
(Continued)

(51) Int. Cl.
| | | |
|---|---|---|
| A61K 38/48 | (2006.01) | |
| A23L 33/15 | (2016.01) | |
| A23L 33/10 | (2016.01) | |
| A61K 31/702 | (2006.01) | |
| A23L 33/175 | (2016.01) | |
| A23L 33/115 | (2016.01) | |
| A61K 45/06 | (2006.01) | |
| A23L 33/11 | (2016.01) | |
| A23L 33/105 | (2016.01) | |
| A23K 20/121 | (2016.01) | |
| A61K 33/42 | (2006.01) | |
| A23L 33/29 | (2016.01) | |
| A23L 33/135 | (2016.01) | |
| A23K 20/24 | (2016.01) | |
| A23K 20/168 | (2016.01) | |
| A23K 20/142 | (2016.01) | |
| A23K 20/189 | (2016.01) | |
| A23K 20/132 | (2016.01) | |
| A23K 20/174 | (2016.01) | |
| A23K 20/10 | (2016.01) | |
| A23K 10/18 | (2016.01) | |
| A23K 20/111 | (2016.01) | |
| A23K 20/158 | (2016.01) | |
| A23K 20/126 | (2016.01) | |
| A23K 20/163 | (2016.01) | |

(Continued)

(52) U.S. Cl.
CPC .......... *A61K 38/4873* (2013.01); *A23K 10/18* (2016.05); *A23K 20/10* (2016.05); *A23K 20/111* (2016.05); *A23K 20/121* (2016.05); *A23K 20/126* (2016.05); *A23K 20/132* (2016.05); *A23K 20/142* (2016.05); *A23K 20/158* (2016.05); *A23K 20/163* (2016.05); *A23K 20/168* (2016.05); *A23K 20/174* (2016.05); *A23K 20/189* (2016.05); *A23K 20/24* (2016.05); *A23L 33/10* (2016.08); *A23L 33/105* (2016.08); *A23L 33/11* (2016.08); *A23L 33/115* (2016.08); *A23L 33/135* (2016.08); *A23L 33/15* (2016.08); *A23L 33/175* (2016.08); *A23L 33/29* (2016.08); *A61K 31/10* (2013.01); *A61K 31/12* (2013.01); *A61K 31/122* (2013.01); *A61K 31/202* (2013.01); *A61K 31/205* (2013.01); *A61K 31/355* (2013.01); *A61K 31/385* (2013.01); *A61K 31/435* (2013.01); *A61K 31/593* (2013.01); *A61K 31/685* (2013.01); *A61K 31/702* (2013.01); *A61K 31/7004* (2013.01); *A61K 31/726* (2013.01); *A61K 33/06* (2013.01); *A61K 33/42* (2013.01); *A61K 35/60* (2013.01); *A61K 35/745* (2013.01); *A61K 35/747* (2013.01); *A61K 36/16* (2013.01); *A61K 36/68* (2013.01); *A61K 36/74* (2013.01); *A61K 36/81* (2013.01); *A61K 36/82* (2013.01); *A61K 36/87* (2013.01); *A61K 36/9068* (2013.01); *A61K 45/06* (2013.01); *A23Y 2220/03* (2013.01); *A23Y 2220/17* (2013.01); *A23Y 2220/67* (2013.01); *A23Y 2220/73* (2013.01); *A23Y 2300/25* (2013.01); *A23Y 2300/49* (2013.01); *A23Y 2300/55* (2013.01)

(58) Field of Classification Search
None
See application file for complete search history.

(56) References Cited

U.S. PATENT DOCUMENTS

| 4,897,224 A | 1/1990 | Kondo et al. |
| 5,502,045 A | 3/1996 | Miettinen et al. |

(Continued)

FOREIGN PATENT DOCUMENTS

| CN | 1254256 | 5/2000 |
| CN | 1875094 | 12/2006 |

(Continued)

OTHER PUBLICATIONS

U.S. Appl. No. 62/099,407, filed Jan. 2, 2015, Rabovsky et al..
U.S. Appl. No. 62/099,410, filed Jan. 2, 2015, Nayak.
U.S. Appl. No. 62/099,428, filed Jan. 2, 2015, Rabovsky et al..
Bassenge et al., "Dietary supplement with vitamin C prevents nitrate tolerance," *J Clin Invest.*, 102(1):67-71, Jul. 1, 1998.
(Continued)

*Primary Examiner* — Vera Afremova
(74) *Attorney, Agent, or Firm* — Fish & Richardson P.C.

(57) ABSTRACT

This document provides dietary supplement compositions. For example, multi-supplement compositions having combinations of dietary supplement formulations useful for human or animal consumption are provided.

24 Claims, 6 Drawing Sheets

Related U.S. Application Data on Jan. 2, 2015, provisional application No. 62/099,407, filed on Jan. 2, 2015.

(51) Int. Cl.

| | | |
|---|---|---|
| *A61K 31/10* | (2006.01) | |
| *A61K 31/12* | (2006.01) | |
| *A61K 31/122* | (2006.01) | |
| *A61K 31/202* | (2006.01) | |
| *A61K 31/205* | (2006.01) | |
| *A61K 31/355* | (2006.01) | |
| *A61K 31/385* | (2006.01) | |
| *A61K 31/435* | (2006.01) | |
| *A61K 31/593* | (2006.01) | |
| *A61K 31/685* | (2006.01) | |
| *A61K 31/7004* | (2006.01) | |
| *A61K 31/726* | (2006.01) | |
| *A61K 33/06* | (2006.01) | |
| *A61K 35/60* | (2006.01) | |
| *A61K 35/745* | (2015.01) | |
| *A61K 35/747* | (2015.01) | |
| *A61K 36/16* | (2006.01) | |
| *A61K 36/68* | (2006.01) | |
| *A61K 36/74* | (2006.01) | |
| *A61K 36/81* | (2006.01) | |
| *A61K 36/82* | (2006.01) | |
| *A61K 36/87* | (2006.01) | |
| *A61K 36/9068* | (2006.01) | |

(56) References Cited

U.S. PATENT DOCUMENTS

| | | | |
|---|---|---|---|
| 6,008,027 A | 12/1999 | Langner | |
| 6,087,353 A | 7/2000 | Stewart et al. | |
| 6,333,047 B1 | 12/2001 | Katagihara et al. | |
| 6,441,206 B1 | 8/2002 | Mikkonen et al. | |
| 6,596,306 B1 | 7/2003 | Ho et al. | |
| 6,713,096 B2* | 3/2004 | Cho | A61K 36/82 424/464 |
| 6,818,233 B2* | 11/2004 | Perkes | C12Y 304/00 424/725 |
| 6,964,969 B2 | 11/2005 | McCleary | |
| 7,138,149 B2 | 11/2006 | Cho | |
| 7,229,651 B2 | 6/2007 | Perkes | |
| 7,923,041 B2* | 4/2011 | Stock | A23F 3/16 424/400 |
| 8,071,610 B2 | 12/2011 | Reynolds | |
| 8,168,170 B2 | 5/2012 | Graham | |
| 8,273,393 B2* | 9/2012 | Rabovsky | A61K 45/06 426/271 |
| 8,491,939 B2 | 7/2013 | Rabovsky et al. | |
| 8,697,158 B2 | 4/2014 | Rabovsky et al. | |
| 8,722,035 B2* | 5/2014 | Porubcan | A61K 9/148 424/600 |
| 8,747,915 B1* | 6/2014 | Giampapa | A61K 36/00 424/725 |
| 9,034,399 B2* | 5/2015 | Rabovsky | A61K 36/16 424/725 |
| 9,179,693 B2 | 11/2015 | Romero et al. | |
| 9,210,945 B2 | 12/2015 | Horgan et al. | |
| 9,259,448 B2 | 2/2016 | Derrieu | |
| 10,576,112 B2 | 3/2020 | Nayak | |
| 2004/0001817 A1 | 1/2004 | Giampapa | |
| 2004/0175389 A1 | 9/2004 | Porubcan | |
| 2004/0228931 A1* | 11/2004 | Chokshi | A61K 9/1658 424/757 |
| 2005/0032757 A1 | 2/2005 | Cho | |
| 2005/0069627 A1 | 3/2005 | Mysore et al. | |
| 2005/0244510 A1 | 11/2005 | Smith | |
| 2006/0153764 A1 | 7/2006 | Sclimacher et al. | |
| 2006/0193842 A1 | 8/2006 | Porubcan | |
| 2007/0099986 A1 | 5/2007 | lShichi | |
| 2007/0154575 A1 | 7/2007 | Shimoda et al. | |
| 2008/0181937 A1 | 7/2008 | Fotuhi | |
| 2009/0175936 A1 | 7/2009 | Rohr | |
| 2009/0175968 A1 | 7/2009 | Ivie et al. | |
| 2009/0181974 A1 | 7/2009 | Bourgeade et al. | |
| 2009/0263492 A1 | 10/2009 | Cashman et al. | |
| 2010/0166721 A1 | 7/2010 | Masri | |
| 2011/0027418 A1 | 2/2011 | Horgan et al. | |
| 2011/0038848 A1 | 2/2011 | Rabovsky et al. | |
| 2011/0064720 A1 | 3/2011 | Amato | |
| 2011/0189132 A1 | 8/2011 | Garner et al. | |
| 2011/0206721 A1 | 8/2011 | Nair | |
| 2012/0009278 A1 | 1/2012 | Perry | |
| 2012/0034324 A1 | 2/2012 | Dubey | |
| 2012/0064051 A1 | 3/2012 | Mercenier et al. | |
| 2013/0216521 A1 | 8/2013 | Culver et al. | |
| 2014/0037582 A1 | 2/2014 | Dupont et al. | |
| 2014/0322282 A1 | 10/2014 | Tuason et al. | |
| 2014/0370091 A1 | 12/2014 | Kikuchi et al. | |
| 2015/0166466 A1 | 6/2015 | Kramer et al. | |
| 2016/0193261 A1 | 7/2016 | Nayak | |
| 2016/0193273 A1 | 7/2016 | Rabovsky et al. | |
| 2019/0167751 A1 | 6/2019 | Rabovsky | |
| 2020/0197454 A1 | 6/2020 | Nayak | |

FOREIGN PATENT DOCUMENTS

| | | |
|---|---|---|
| CN | 103193614 | 7/2013 |
| CN | 103524324 | 1/2014 |
| CN | 103664667 | 3/2014 |
| CN | 103880645 | 6/2014 |
| CN | 103951618 | 7/2014 |
| CN | 103976975 | 8/2014 |
| EP | 2520177 | 5/2017 |
| TW | 201431561 | 8/2014 |
| WO | WO1999007400 | 2/1999 |
| WO | WO 03/026687 | 4/2003 |
| WO | WO 2004/022031 | 3/2004 |
| WO | WO2006026713 | 3/2006 |
| WO | WO2006097043 | 9/2006 |
| WO | WO 2007/140621 | 12/2007 |
| WO | WD2010006173 | 1/2010 |
| WO | WO2011004375 | 1/2011 |
| WO | WO2011019867 | 2/2011 |
| WO | WO2011019875 | 2/2011 |
| WO | WO 2012/123 770 | 9/2012 |
| WO | WO2014025905 | 2/2014 |
| WO | WO2014070014 | 5/2014 |
| WO | WO2014151329 | 9/2014 |
| WO | WO 2014/195741 | 12/2014 |
| WO | WO2015017625 | 2/2015 |

OTHER PUBLICATIONS

Bobko et al., "Trityl-based EPR probe with enhanced sensitivity to oxygen," *Free Radic Biol Med.*, 47(5):654-658, Epub Jun. 10, 2009.
Dikalov et al., "ESR techniques for the detection of nitric oxide in vivo and in tissues," *Methods Enzymol.*, 396:597-610, 2005.
Falbe, Ed., "Emulsions (HLB Values)," Surfactants in Consumer Products, 4.2.4 pp. 149-153, 1989.
Feuerstein et al., "Cytokines, inflammation, and brain injury: role of tumor necrosis factor-alpha," *Cerebrovasc Brain Metab Rev.*, 6(4):341-360, Winter 1994.
Fink et al., "A new approach for extracellular spin trapping of nitroglycerin-induced superoxide radicals both in vitro and in vivo," *Free Radic Biol Med.*, 28(1):121-128, Jan. 1, 2000.
Komarov et al., "Electron paramagnetic resonance monitoring of ischemia-induced myocardial oxygen depletion and acidosis in isolated rat hearts using soluble paramagnetic probes," *Magn Reson Med.*, 68(2):649-655, Epub Dec. 12, 2011.
Mrakic-Sposta et al., "Assessment of a standardized ROS production profile in humans by electron paramagnetic resonance," *Oxid Med Cell Longev.*, vol. 2012 Article ID 973927, 10 pages, 2012.
Pisaneschi et al., "Compensatory feto-placental upregulation of the nitric oxide system during fetal growth restriction," *PLoS One*, 7(9):e45294, Epub Sep. 27, 2012.

(56) References Cited

OTHER PUBLICATIONS

Purest Colloids, Inc., "Theralac Probiotic," Purest Colloids [online] copyright 2014 [retrieved on Dec. 18, 2014]. Retrieved from the Internet: <URL:www.purestcolloids.com/inside-theralac.php>, 2 pages.
International Search Report and Written Opinion for PCT/US2016/012091, dated Mar. 17, 2016, 12 pages.
Wikipedia, "Acetylcarnitine," Wikipedia.org [online] last modified Sep. 20, 2014. Retrieved from the Internet: <URL:http://en.wikipedia.org/wiki/Acetylcarnitine>. Retrieved on Nov. 19, 2014, 4 pages.
Wikipedia, "Curcumin," Wikipedia.org [online] last modified Nov. 7, 2014. Retrieved from the Internet: <URL: http://en.wikipedia.org/wiki/Curcumin>, retrieved on Nov. 20, 2014, 6 pages.
Wikipedia, "Huperzine A," Wikipedia.org [online], last modified Nov. 10, 2014. Retrieved from the Internet: <http://en.wikipedia.org/wiki/Huperzine_A>, 4 pages.
Extended European Search Report in Application No. 16732905.1, dated Jun. 14, 2018, 9 pages.
International Preliminary Report on Patentability for International Application No. PCT/US2016/012091, dated Jul. 13, 2017, 7 pages.
Wong et al., "Treatment of non-alcoholic steatohepatitis with probiotics. A proof-of-concept study," *Annals of hepatology.*, 12(2):256-262, Mar. 1, 2013.
Partial Supplementary European Search Report in Application No. 16732909.3, dated Jul. 25, 2018, 12 pages.
Bryan, et al., J. Nutr., 132:1345. (Year: 2002).
Di Meo, et al., J. Exp. Clin. Cancer Res., 38:360. (Year: 2019).
Lee, et al., Cur. Neuropharmacol., 11:338. (Year: 2013).
Memory Pro 2011 product listing, retrieved from the Wayback Machine, Internet Archive, (https://web.archive.org/web/20111025131756/http://pureencapsulations.com/itemdy00.asp?T1=MEP1). (Year: 2011).
Memory Pro, Dietary Supplement, Manufacturer: Pure Encapsulations®, Available on Amazon.com, https://vwvw.amazon.com/Pure-Encapsulations-Supplement-Broad-Spectrum-Capsules/dp/B01N9VLPIZ?ref_=ast sto_dp#customerReviews. (Year: 2008).
Xu, et al., Acta Pharmacologice Sinica, 16:391. (Year: 1995).

\* cited by examiner

MULTI-SUPPLEMENT COMPOSITIONS

CROSS-REFERENCE TO RELATED APPLICATIONS

This application claims priority under 35 U.S.C. § 119(e) to U.S. Provisional Patent Application No. 62/099,428, filed Jan. 2, 2015, entitled "Multi-Supplement Compositions," U.S. Provisional Patent Application No. 62/099,407, filed Jan. 2, 2015, entitled "Dietary Supplement Compositions," and U.S. Provisional Patent Application No. 62/099,410, filed Jan. 2, 2015, and entitled "Bacterial Compositions," all of which are incorporated by reference herein in their entireties.

BACKGROUND

1. Technical Field

This document relates to the field of dietary supplements. For example, this document relates to multi-supplement compositions that include combinations of dietary supplement formulations useful for human or animal consumption.

2. Background Information

Many people desire improved health and well-being. In many cases, few, if any, supportive supplements are available for these people. In addition, many people strive to maintain a healthy diet and level of activity. Accordingly, many people take dietary supplements to support their health and well-being.

SUMMARY

This document provides dietary supplement compositions. For example, this document provides multi-supplement compositions having combinations of dietary supplement formulations useful for human or animal consumption. In some cases, the multi-supplement compositions provided herein can provide a broad range of supplementation to support a consumer's overall health and well-being.

In general, one aspect of this document features a multi-supplement composition comprising (a) a probiotic supplement; (b) a multivitamin and mineral supplement; (c) an antioxidant supplement; and (d) an anti-inflammatory supplement. The composition can further comprise a fish oil supplement.

In another aspect, this document features a multi-supplement composition comprising:
(a) a dietary supplement of a Supplement Formulation A comprising:
  (i) from about 5 billion to about 15 billion CFU of a mixture of *Lactobacillus acidophilus, Lactobacillus plantarum, Lactobacillus casei, Lactobacillus rhamnosus, Bifidobacterium longum, Bifidobacterium lactis,* and *Bifidobacterium bifidum,*
  (ii) a filler having a water activity less than 0.2, and
  (iii) a capsule,
  wherein the dietary supplement of a Supplement Formulation A releases the *Lactobacillus acidophilus, Lactobacillus plantarum, Lactobacillus casei, Lactobacillus rhamnosus, Bifidobacterium longum, Bifidobacterium lactis,* and *Bifidobacterium bifidum* within an intestine of a mammal following oral administration to the mammal;
(b) a dietary supplement of a Supplement Formulation B comprising one or more of:
  (i) a fat-soluble antioxidant,
  (ii) a phenolic compound, and
  (iii) a water soluble antioxidant;
(c) a dietary supplement of a Supplement Formulation C comprising one or more of:
  (i) an iridoid,
  (ii) a ginger component,
  (iii) an anthocyanin, and
  (iv) at least one agent selected from the group consisting of a coumarin, a curcuminoid, and a green tea extract;
(d) a dietary supplement of a Supplement Formulation E comprising one or more of:
  (i) a grape seed extract, and
  (ii) an enzyme selected from the group consisting of a fungal protease, an acid stable protease, and bromelain; and
(e) a dietary supplement of a Supplement Formulation F comprising a mineral-amino acid compound/polysaccharide complex.

The composition can further comprise a dietary supplement of a Supplement Formulation G comprising one or more of:
  (i) huperzine A,
  (ii) acetyl-L-carnitine,
  (iii) a *Bacopa monnieri* extract, and
  (iv) curcumin.

The composition can further comprise a dietary supplement of a Supplement Formulation H comprising one or more of:
  (i) phosphatidylserine,
  (ii) DHA,
  (iii) EPA,
  (iv) an antioxidant, and
  (v) *Ginkgo biloba.*

The composition can further comprise a dietary supplement of a Supplement Formulation D comprising fish oil.

The composition can further comprise a dietary supplement of a Supplement Formulation I comprising one or more of Vitamin $K_2$ and Vitamin $D_3$.

The composition can further comprise a dietary supplement of a Supplement Formulation J comprising one or more of CoQ10, a tocotrienol, and alpha-lipoic acid.

The composition can further comprise a dietary supplement of a Supplement Formulation K comprising one or more of:
  (i) a sterol compound, and
  (ii) an omega 3 fatty acid.

The composition can further comprise a dietary supplement of a Supplement Formulation L comprising calcium.

The composition can further comprise a dietary supplement of a Supplement Formulation M comprising one or more of chondroitin sulfate and methyl sulfonyl methane.

In some embodiments, the composition can further comprise a dietary supplement of a Supplement Formulation N comprising one or more of a green coffee bean extract, a *capsicum* extract, a green tea extract, or a green tea phytosome. In some embodiments, the composition can further comprise a dietary supplement of a Supplement Formulation N comprising a green coffee bean extract, a green tea phytosome, a green tea extract, and a red pepper extract.

In another aspect, this document features a multi-supplement composition comprising:
(a) a dietary supplement of a Supplement Formulation E comprising:
  (i) a grape seed extract, and
  (ii) an enzyme selected from the group consisting of a fungal protease, an acid stable protease, and bromelain;
(b) a dietary supplement of a Supplement Formulation I comprising Vitamin $K_2$ and Vitamin $D_3$;
(c) a dietary supplement of a Supplement Formulation J comprising CoQ10, a tocotrienol, and alpha-lipoic acid; and
(d) a dietary supplement of a Supplement Formulation K comprising:
  (i) a sterol compound, and
  (ii) an omega 3 fatty acid.

In another aspect, this document discloses a supplement composition comprising:
(a) from about 5 billion to about 15 billion cfu of a mixture of *Lactobacillus acidophilus, Lactobacillus plantarum, Lactobacillus casei, Lactobacillus rhamnosus, Bifidobacterium longum, Bifidobacterium lactis,* and *Bifidobacterium bifidum,*
(b) a fat-soluble antioxidant,
(c) a phenolic compound,
(d) a water soluble antioxidant,
(e) an iridoid,
(e) a ginger component,
(f) an anthocyanin,
(g) at least one agent selected from the group consisting of a coumarin, a curcuminoid, and a green tea extract;
(h) a grape seed extract,
(i) an enzyme selected from the group consisting of a fungal protease, an acid stable protease, and bromelain, and
(j) a mineral-amino acid compound/polysaccharide complex.

As used herein, the term "about" when used to refer to weight % in a composition means±10% of the reported weight %. As used herein, the term "about" when used to refer to measured characteristics of the composition means±20% of the reported value.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
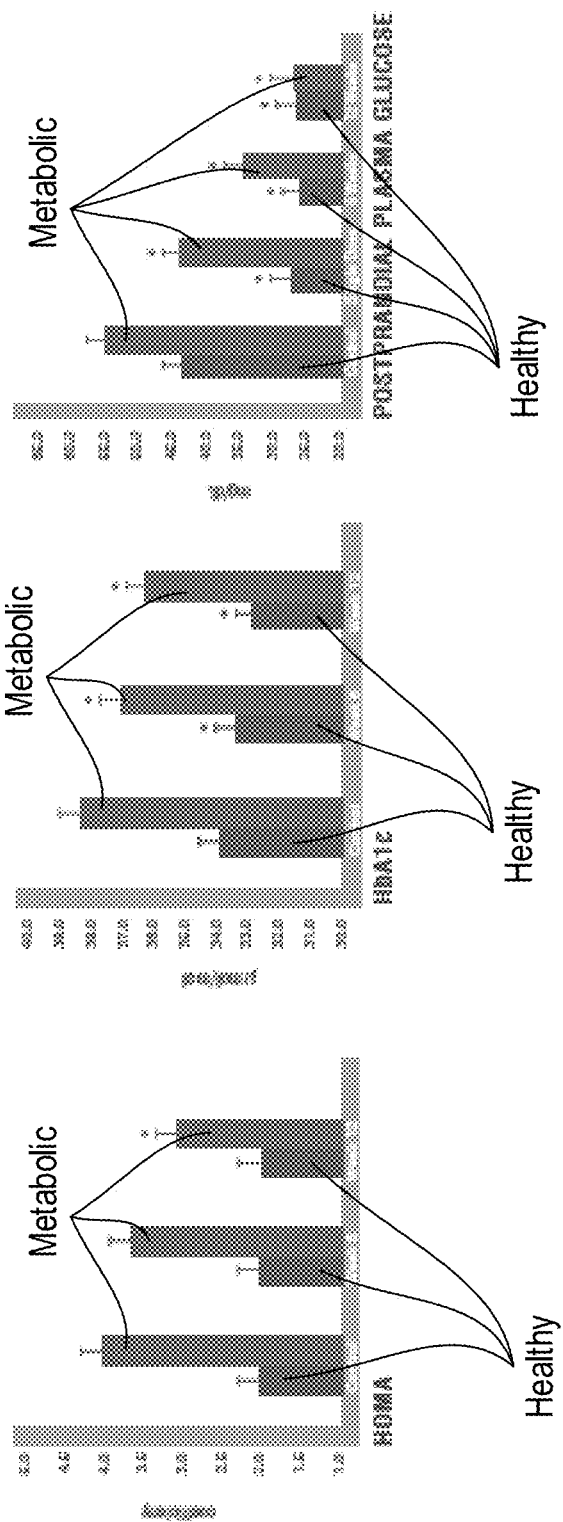
FIG. 1 provides bar graphs comparing control and test groups (i.e., healthy (left bar) and metabolic (right bar) groups) showing HOMA, HbA1c, and postprandial plasma glucose levels after one dose, 6 weeks, and 12 weeks.

This document provides multi-supplement compositions that can include three or more different dietary supplement formulations. A dietary supplement formulation can be in the form of a liquid, solution, suspension, tablet, powder, cream, mist, atomized vapor, aerosol, soft gelatin capsule, hard gelatin capsule, a gel, a confectionary, a shake, a bar, and a supplemented food. In some cases, a multi-supplement composition provided herein can include three, four, five, six, seven, eight, nine, ten, or more different dietary supplement formulations. For example, a multi-supplement composition provided herein can include (a) at least one capsule or tablet (or a collection of capsules or tablets) for each of Supplement Formulation A, Supplement Formulation B, Supplement Formulation C, Supplement Formulation D, Supplement Formulation E, and Supplement Formulation F, (b) at least one capsule or tablet (or a collection of capsules or tablets) for each of Supplement Formulation A, Supplement Formulation B, Supplement Formulation C, Supplement Formulation D, another Supplement Formulation D with a different composition than the first Supplement Formulation D, Supplement Formulation E, Supplement Formulation F, Supplement Formulation G, and Supplement Formulation H, (c) at least one capsule or tablet (or a collection of capsules or tablets) for each of Supplement Formulation E, Supplement Formulation I, Supplement Formulation J, and Supplement Formulation K, (d) at least one capsule or tablet (or a collection of capsules or tablets) for each of Supplement Formulation A, Supplement Formulation B, Supplement Formulation C, Supplement Formulation D, Supplement Formulation E, Supplement Formulation F, Supplement Formulation I, Supplement Formulation J, and Supplement Formulation K, or (e) at least one capsule or tablet (or a collection of capsules or tablets) for each of Supplement Formulation A, Supplement Formulation B, Supplement Formulation C, Supplement Formulation D, Supplement Formulation E, Supplement Formulation F, Supplement Formulation I, and Supplement Formulation L.

In some cases, a multi-supplement composition provided herein can include at least one capsule or tablet (or a collection of capsules or tablets) for each of Supplement Formulation A, Supplement Formulation B, Supplement Formulation C, a first Supplement Formulation D (e.g., a first Supplement Formulation D with more EPA than DHA), a second Supplement Formulation D different from the first Supplement Formulation D (e.g, a second Supplement Formulation D with more DHA than EPA), Supplement Formulation E, Supplement Formulation F, Supplement Formulation G, and Supplement Formulation H.

In some cases, a multi-supplement composition provided herein can include at least one capsule or tablet (or a collection of capsules or tablets) for each of Supplement Formulation A, Supplement Formulation B, a first Supplement Formulation C, a second Supplement Formulation C different from the first Supplement Formulation C, Supplement Formulation D, Supplement Formulation E, Supplement Formulation F, Supplement Formulation I, and Supplement Formulation L.

The collections of capsules or tablets of a particular dietary supplement formulation can be housed together within a separate container within a single multi-supplement composition. For example, a single multi-supplement composition having six different dietary supplements can be in the form of a package housing six different bottles, with each bottle containing a collection (e.g., 10, 15, 25, 50, 75, 100, or more) of capsules or tablets for one of the six different dietary supplements. The collections of capsules or tablets of a particular dietary supplement formulation can also be housed together as single dose packets. For example, a single dose of capsules or tablets of a particular dietary supplement formulation can be housed together in a sealed aluminum foil pouch. A daily regimen, by way of example, may include separate AM and PM pouches, each with a selection of dietary supplements as disclosed herein. Morning and evening supplementation to a user may occur at optimized delivery times.

The supplement formulations of the herein disclosed invention are not necessarily physically limited to separate supplement forms or to distinct combinations disclosed herein. For example, when the administration forms are compatible as is known to those skilled in the art, the various ingredients in the Supplement Formulations A-N can be combined in different tablets, capsules, powder, softgel, etc. arrangements than those listed herein. For example, components of Supplement Formulations B and F can be combined or divided into different tablet combinations than suggested herein. Alternatively, if a particular formulation component is repeated across different Supplement Formulations, it is understood that in some embodiments of the compositions provided herein that the particular formulation component need not be repeated across each Supplement Formulation. For example, some embodiments of the compositions provided herein may include each of Formulations C and G, wherein both of Formulations C and need not both contain curcumin, although doing so in distinct tablets can be another acceptable embodiment. As such, some embodiments described in this document include multiple formulations (e.g., Formulations C and G), wherein one or more individual formulations (e.g., Formulation C, but not Formulation G) that make up the multiple formulations contain a particular ingredient (e.g., curcumin) while other individual formulations do not contain the particular ingredient.

Supplement Formulation A

Supplement Formulation A can provide a stabilized mixture of probiotic bacteria. A dietary supplement of a Supplement Formulation A can include a combination of different bacterial strains (e.g., a combination of at least two, three, four, five, six, seven, eight, nine, or ten different bacterial strains) formulated in a manner to maintain the stability of the bacteria. A dietary supplement of a Supplement Formulation A can be in the form of powders, capsules, pills, tablets, chewing gums, lozenges, candy, or sachet. In some cases, a dietary supplement of a Supplement Formulation A can include a coating designed to prevent moisture adsorption and minimize the water activity of the final blend to provide a formulation with good long term stability.

For example, methacrylate coatings, hydroxy propyl methyl cellulose pthalate coatings, cellulose acetate succinate coatings, hydroxy propyl methyl cellulose acetate succinate coatings, polyvinyal acetate pthalate coatings, or cellulose acetate trimellitate, sodium alginate coatings can be used to deliver the bacterial contents of a dietary supplement of a Supplement Formulation A past the stomach. Such coatings can be made and applied as described elsewhere (e.g., U.S. Patent Application Publication No. 2014/370091, Chinese Patent No. CN103976975, and Taiwan Patent No. TW201431561).

In some cases, a dietary supplement of a Supplement Formulation A can include any combination of at least six (e.g., at least seven, eight, nine, or ten) different bacterial strains. Examples of different bacterial strains that can be formulated into a dietary supplement of a Supplement Formulation A include, without limitation, *Lactobacillus acidophilus, Lactobacillus plantarum, Lactobacillus casei, Lactobacillus rhamnosus, Bifidobacterium longum, Bifidobacterium lactis, Bifidobacterium bifidum, Bacillus coagulans, Lactobacillus paracasei, Lactobacillus johnsonii, Lactobacillus reuteri, Lactobacillus bulgaricus, Bifidobacterium breve, Lactobacillus brevis, Lactococcus lactis* and *Streptococcus thermophilus*. In some cases, a dietary supplement of a Supplement Formulation A can include one or more bacterial species such as *Saccharomyces boulardii*. In some cases, the only bacterial strains present within a particular dietary supplement of a Supplement Formulation A can be *Lactobacillus acidophilus, Lactobacillus plantarum, Lactobacillus casei, Lactobacillus rhamnosus, Bifidobacterium longum, Bifidobacterium lactis*, and *Bifidobacterium bifidum* or any combination of six selected from *Lactobacillus acidophilus, Lactobacillus plantarum, Lactobacillus casei, Lactobacillus rhamnosus, Bifidobacterium longum, Bifidobacterium lactis*, and *Bifidobacterium bifidum*.

In some cases, a dietary supplement of a Supplement Formulation A can include any combination of at least two difference bacterial strains, for example *Lactobacillus* and *Bifidobacterium*.

Unless otherwise noted, all bacteria amounts for a dietary supplement of a Supplement Formulation A are provided on a per gram of total bacterial composition in the composition basis. In some cases, a dietary supplement of a Supplement Formulation A can contain at least about $1 \times 10^9$ CFUs of each different bacterial strain included in the bacterial composition. In some cases, a dietary supplement of a Supplement Formulation A can contain between about $1 \times 10^8$ and about $1 \times 10^{11}$ bacteria of all species (e.g., between about $1 \times 10^9$ and about $4 \times 10^{10}$ bacteria of all species). For example, a dietary supplement of a Supplement Formulation A can include between about $1 \times 10^7$ CFUs and about $3 \times 10^9$ CFUs of *Lactobacillus acidophilus*, between about $1 \times 10^7$ CFUs and about $4 \times 10^9$ CFUs of *Lactobacillus plantarum*, between about $1 \times 10^7$ CFUs and about $3 \times 10^9$ CFUs of *Lactobacillus casei*, between about $1 \times 10^7$ CFUs and about $3.2 \times 10^9$ CFUs of *Lactobacillus rhamnosus*, between about $1 \times 10^7$ CFUs and about $1.6 \times 10^9$ CFUs of *Bifidobacterium*

*longum*, between about 1×10⁷ CFUs and about 3.6×10⁹ CFUs of *Bifidobacterium lactis*, and between about 1×10⁷ CFUs and about 1.6×10⁹ CFUs of *Bifidobacterium bifidum*.

Any appropriate method can be used to obtain the bacterial strains to be included within a dietary supplement of a Supplement Formulation A. For example, culturing techniques can be used to obtain large amounts of particular bacterial strains. In some cases, the bacterial strains to be included within a dietary supplement of a Supplement Formulation A can be obtained commercially. For example, *Lactobacillus acidophilus* can be obtained commercially from Dupont Inc. (Madison, Wis.; Cat. No. LA-14 200B); *Lactobacillus plantarum* can be obtained commercially from Dupont Inc. (Madison, Wis.; Cat. No. LP-115 400B); *Lactobacillus casei* can be obtained commercially from Dupont Inc. (Madison, Wis.; Cat. No. LC-11 300B), *Lactobacillus rhamnosus* can be obtained commercially from Dupont Inc. (Madison, Wis.; Cat. No. LR-32 200B), *Bifidobacterium longum* can be obtained commercially from Dupont Inc. (Madison, Wis.; Cat. No. BL-05 100B), *Bifidobacterium lactis*, can be obtained commercially from Dupont Inc. (Madison, Wis.; Cat. No. BL-04 450B), and *Bifidobacterium bifidum* can be obtained commercially from Dupont Inc. (Madison, Wis.; Cat. No. BB-06 100B).

A dietary supplement of a Supplement Formulation A can include one or more other ingredients. For example, a dietary supplement of a Supplement Formulation A can include fructooligosaccharides. In some cases, a dietary supplement of a Supplement Formulation A can include between about 0.5 mg and about 50 mg (e.g., between about 1 mg and about 50 mg, between about 5 mg and about 50 mg, between about 10 mg and about 50 mg, between about 0.5 mg and about 25 mg, between about 0.5 mg and about 20 mg, between about 0.5 mg and about 15 mg, between about 0.5 mg and about 10 mg, or between about 5 mg and about 20 mg) of fructooligosaccharides per bacterial composition. For example, a dietary supplement of a Supplement Formulation A can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 5 mg and about 20 mg of fructooligosaccharides.

In some cases, a dietary supplement of a Supplement Formulation A can include between about 1 mg and about 50 mg (e.g., between about 1 mg and about 20 mg, between about 2 mg and about 20 mg, or between about 2 mg and about 10 mg) of fructooligosaccharides for every gram of the bacterial composition. For example, a dietary supplement of a Supplement Formulation A that weighs 2 grams can contain between about 10 mg and about 100 mg of fructooligosaccharides.

Any appropriate method can be used to obtain fructooligosaccharides that can be included in a dietary supplement of a Supplement Formulation A. For example, fructooligosaccharides can be obtained by an inulin degradation process or by a transfructosylation process as described elsewhere (U.S. Patent Application Publication No. 2005/069627). In some cases, fructooligosaccharides can be obtained commercially from Agaviotica Inc. (Monterrey, NL (Mexico); Cat. No. Fructagave PR-95).

In some cases, a dietary supplement of a Supplement Formulation A can include a glidant (e.g., silica). Examples of glidants that can be included within a dietary supplement of a Supplement Formulation A include, without limitation, silica, stearic acid, calcium stearate, magnesium stearate, sodium stearate, glyceryl behapate (compritol), liquid paraffin, aerosil (colloidal silicon dioxide), starch and talc, DL-leucine, and sodium lauryl sulphate. For example, a dietary supplement of a Supplement Formulation A can include between about 2.00 mg and about 5.00 mg (e.g., between about 0.005 mg and about 010 mg, between about 0.01 mg and about 0.02 mg, or between about 0.25 mg and about 0.50 mg) of a glidant (e.g., silica) per bacterial composition. For example, a dietary supplement of a Supplement Formulation A can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 0.005 mg and about 0.02 mg of silica.

In some cases, a dietary supplement of a Supplement Formulation A can include between about 2.0 mg and about 5.0 mg of a glidant (e.g., silica) for every gram of the bacterial composition. For example, a dietary supplement of a Supplement Formulation A that weighs 2 grams can contain between about 4.0 mg and about 10.0 mg of a glidant (e.g., silica).

Any appropriate method can be used to obtain of a glidant (e.g., silica) that can be included in a dietary supplement of a Supplement Formulation A. For example, silica can be obtained as described elsewhere (U.S. Patent Application Publication No. 2006/153764). In some cases, silica can be obtained commercially from Grace Davison Inc. (Baltimore, Md.; Cat. No. Syloid 244).

In some cases, a dietary supplement of a Supplement Formulation A can include a filler having an $A_w$ of less than 0.2. Examples of such fillers include, without limitation, microcrystalline cellulose (MCC 112), rice maltodextrin, lactose anhydrous, mannitol, microcrystalline cellulose (MCC 302), microcrystalline cellulose (MCC 200 LM), microcrystalline cellulose (MCC 101), starch, xylitol, sorbitol, hydroxyl propyl cellulose, gelatin, poly vinyl pyrrolidone, and dibasic calcium phosphate. In some cases, a dietary supplement of a Supplement Formulation A can include between about 300 mg and about 700 mg of a filler having an $A_w$ of less than 0.2 (e.g., MCC 112) per bacterial composition. For example, a dietary supplement of a Supplement Formulation A can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 300 mg and about 700 mg of a filler having a $A_w$ of less than 0.2 (e.g., MCC 112). In some cases, a dietary supplement of a Supplement Formulation A can include between about 300 mg and about 700 mg of a filler having a $A_w$ of less than 0.2 (e.g., MCC 112) for every gram of the bacterial composition. For example, a dietary supplement of a Supplement Formulation A that weighs 2 grams can contain between about 600 mg and about 1400 mg of a filler having a $A_w$ of less than 0.2 (e.g., MCC 112). As a result, the final composition can have an $A_w$ of less than 0.3.

Any appropriate method can be used to obtain a filler having a $A_w$ of less than 0.2 for use in a dietary supplement of a Supplement Formulation A. For example, a filler having a $A_w$ of less than 0.2 can be obtained as described elsewhere (U.S. Patent Application Publication No. US20140322282, published Oct. 30, 2014). In some cases, a filler having an $A_w$ of less than 0.2 can be obtained commercially from Mingtai chemical Co Ltd., Taiwan, Cat. No. M112 D.

In some cases, a dietary supplement of a Supplement Formulation A can include magnesium stearate. For example, a dietary supplement of a Supplement Formulation A can include between about 10 mg and about 20 mg of magnesium stearate per bacterial composition. For example, a dietary supplement of a Supplement Formulation A can contain *Lactobacillus acidophilus, Lactobacillus plantarum, Lactobacillus casei, Lactobacillus rhamnosus, Bifidobacterium longum, Bifidobacterium lactis,* and *Bifidobacterium bifidum* and between about 10 mg and about 20 mg of magnesium stearate.

In some cases, a dietary supplement of a Supplement Formulation A can include between about 10 mg and about 20 mg of magnesium stearate for every gram of the bacterial composition. For example, a dietary supplement of a Supplement Formulation A that weighs 2 grams can contain between about 20 mg and about 40 mg of magnesium stearate.

Any appropriate method can be used to obtain magnesium stearate that can be included in a dietary supplement of a Supplement Formulation A. For example, magnesium stearate can be obtained as described elsewhere (e.g., Chinese Patent No. CN103880645, dated Jun. 25, 2014; Chinese Patent No. CN103524324, dated Jan. 22, 2014, and Chinese Patent No. CN10319361, dated Jul. 10, 2013). In some cases, magnesium stearate can be obtained commercially from Peter Greven Asia, Malaysia; Cat. No. Palmstar MGST 200.

A dietary supplement of a Supplement Formulation A (e.g., a capsule or tablet) can be formulated to have a particular dose. For example, a dietary supplement of a Supplement Formulation A can be in the form of a capsule or tablet with a total weight that is between about 150 mg and about 800 mg (e.g., between about 200 mg and about 800 mg, between about 300 mg and about 800 mg, between about 350 mg and about 800 mg, between about 150 mg and about 700 mg, between about 150 mg and about 650 mg, or between about 350 mg and about 700 mg).

As described herein, a single dietary supplement of a Supplement Formulation A (e.g., a capsule or tablet) can be formulated to include at least six different bacterial strains and a filler having an $A_w$ less than 0.2 (e.g., MCC 112) in a manner that helps maintain the stability of the bacteria within the composition. In some cases, a single dietary supplement of a Supplement Formulation A can be coated with at coating or placed into a capsule having the ability to deliver the contents to the intestines of a mammal following oral administration. For example, a dietary supplement of a Supplement Formulation A can be designed to release its contents when the composition reaches a location of the intestines having a pH above about 6.8. In some cases, a dietary supplement of a Supplement Formulation A that includes at least two different bacterial strains (e.g., at least two, three, four, five, six, seven, eight, nine, or more different bacterial strains) and a filler having an $A_w$ less than 0.2 (e.g., MCC 112) can include fructooligosaccharides, magnesium stearate, and/or silica. In some cases, the bacterial strains of a dietary supplement of a Supplement Formulation A can be lyophilized to form a dried powder containing viable bacteria. In some cases, a single dietary supplement of a Supplement Formulation A (e.g., a capsule or tablet or sachet) can be formulated to include at least seven different lyophilized bacterial strains, a filler having an $A_w$ less than 0.2 (e.g., MCC 112), fructooligosaccharides, magnesium stearate, and silica.

In some cases, a dietary supplement of a Supplement Formulation A can maintain the viability of at least about 80 percent (e.g. at least about 90, 95, or 99 percent) of the bacteria for at least 12 months (e.g., at least 40, 50, 60, 70, 80, or 90 days or at least 3, 6, 9, or 12 months) under standard storage conditions (e.g., room temperature under normal humidity). In some cases, a dietary supplement of a Supplement Formulation A can maintain the viability of at least about 80 percent of the bacteria for at least 18 months or for at least 24 months.

A dietary supplement of a Supplement Formulation A can be administered to a mammal (e.g., a human). In some cases, a human can be instructed to self-administer a number (e.g., one, two, three, four, five, or more) of dietary supplements of a Supplement Formulation A (e.g., capsules or tablets or sachets) per unit time (e.g., per day, per week, or per month). For example, a human can be instructed to self-administer one or two dietary supplements of a Supplement Formulation A per day.

In one example, a daily dose of a dietary supplement of a Supplement Formulation A can be designed to provide the following effective amounts:

| | |
|---|---|
| A blend of *Lactobacillus acidophilus, Lactobacillus plantarum, Lactobacillus casei, Lactobacillus rhamnosus, Bifidobacterium longum, Bifidobacterium lactis,* and *Bifidobacterium bifidum* | 10 billion CFU |
| Fructooligosaccharides | 10 mg |

A daily dose may be prepared and administered in the form of one or more capsules or tablets (e.g., two capsules or tablets, three capsules or tablets, four capsules or tablets, five capsules or tablets, and six capsules or tablets). In some cases, one or more capsules or tablets can be administered in one or more dosages over the course of 24 hours (e.g., one dose, two doses, three doses, four doses, five doses, and six doses), wherein the one or more dosages do not exceed the total daily dose.

In some cases, a dietary supplement of a Supplement Formulation A can be made and used as described in U.S. Provisional Patent Application No. 62/099,410, which is herein incorporated by reference in its entirety. For example, a dietary supplement of a Supplement Formulation A can be made to have the ingredients as set forth in U.S. Provisional Patent Application No. 62/099,410.

Supplement Formulation B

Supplement Formulation B can provide broad spectrum anti-aging and anti-oxidant protection at the cellular level that may block or slow damaging of DNA, lipid, and protein molecules. In some cases, a dietary supplement of a Supplement Formulation B can protect many classes of biomolecules involved in the aging process from damage.

In general, a dietary supplement of a Supplement Formulation B can include, without limitation, fat-soluble antioxidants, phenolic compounds, and/or water soluble antioxidants. For example, a dietary supplement of a Supplement Formulation B can include at least one fat-soluble antioxidant, at least one phenolic compound, and at least one water soluble antioxidant. Examples of fat-soluble antioxidants that can be included within a dietary supplement of a Supplement Formulation B include, without limitation, tocopherols such as α-tocopherol, β-tocopherol, γ-tocopherol, and δ-tocopherol, carotenoids such as α-carotene, β-carotene, criptoxanthin, zeaxanthin, lutein, and lycopene. In some cases, a dietary supplement of a Supplement Formulation B can include a carotenoid blend that includes α-carotene, β-carotene, criptoxanthin, zeaxanthin, lutein, and lycopene. Examples of phenolic compounds that can be included within a dietary supplement of a Supplement Formulation B include, without limitation, tyrosol, hydroxytyrosol, verbascoside, olive extract containing tyrosol, hydroxytyrosol, oleuropein, verbascoside and/or, oligomeric proanthocyanidins, grape seed extract containing oligomeric proanthocyanidins, catechin, epicatechin, gallic acid. An example of a water soluble antioxidant that can be included within a dietary supplement of a Supplement Formulation B includes, without limitation, Vitamin C (ascorbic acid). In some cases, a dietary supplement of a Supplement Formulation B can be formulated into a single composition (e.g., a capsule) having one or more of α-tocopherol, β-tocopherol, γ-tocopherol, δ-tocopherol, α-carotene, β-carotene, criptoxanthin, zeaxanthin, lutein, lycopene, olive fruit extract, grape seed extract, and vitamin C.

In some cases, a dietary supplement of a Supplement Formulation B can include ingredients having the ability to reduce the risk of cardiovascular disease, reduce the risk of cataracts, improve immune system function, improve vision (eye) function, improve regulation of gene expression, improve body and organ growth and development, improve red blood cell production, reduce lipid peroxidation markers, increase resistance of LDL to oxidation, reduce DNA peroxidation markers, reduce inflammation, reduce UV-light sensitivity or UV-light induced skin erythema, reduce risk of prostate cancer, reduce risk of breast cancer, reduce wrinkle formation, reduce cellular damage, increase protection against free radical DNA damage in cells, increase protection against sun damage or environmental aging, stimulate phase II detoxification enzyme activity, inhibit tumor invasion and angiogenesis, and/or reduce risk of stroke.

In some cases, a dietary supplement of a Supplement Formulation B can be formulated into a single composition (e.g., a capsule) that has from about 5 mg to about 150 mg α-tocopherol, from about 0.7 mg to about 20 mg β-tocopherol, from about 10 mg to about 300 mg γ-tocopherol, from about 2.5 mg to about 75 mg δ-tocopherol, from about 0.01 mg to about 0.3 mg α-carotene, from about 0.2 mg to about 6 mg β-carotene, from about 0.02 mg to about 0.6 mg criptoxanthin, from about 0.01 mg to about 0.3 mg zeaxanthin, from about 0.01 mg to about 0.3 mg lutein, from about 0.3 mg to about 9 mg lycopene, from about 15 mg to about 450 mg olive fruit extract (10% total phenolic content by weight), from about 2.5 mg to about 75 mg grape seed extract, and/or from about 30 mg to about 900 mg vitamin C. For example, a dietary supplement of a Supplement Formulation B can be formulated into a single composition (e.g., a capsule) that has from about 5 mg to about 150 mg α-tocopherol, from about 0.7 mg to about 20 mg β-tocopherol, from about 10 mg to about 300 mg γ-tocopherol, from about 2.5 mg to about 75 mg δ-tocopherol, from about 0.01 mg to about 0.3 mg α-carotene, from about 0.2 mg to about 6 mg β-carotene, from about 0.02 mg to about 0.6 mg criptoxanthin, from about 0.01 mg to about 0.3 mg zeaxanthin, from about 0.01 mg to about 0.3 mg lutein, from about 0.3 mg to about 9 mg lycopene, from about 15 mg to about 450 mg olive fruit extract (10% total phenolic content by weight), from about 2.5 mg to about 75 mg grape seed extract, and from about 30 mg to about 900 mg vitamin C.

In other cases, a dietary supplement of a Supplement Formulation B can be formulated into a single composition (e.g., a capsule) that has from about 5 mg to about 150 mg α-tocopherol, from about 0.7 mg to about 20 mg β-tocopherol, from about 10 mg to about 300 mg γ-tocopherol, from about 2.5 mg to about 75 mg δ-tocopherol, from about 0.01 mg to about 0.3 mg α-carotene, from about 0.2 mg to about 6 mg β-carotene, from about 0.02 mg to about 0.6 mg criptoxanthin, from about 0.01 mg to about 0.3 mg zeaxanthin, from about 0.01 mg to about 0.3 mg lutein, from about 0.3 mg to about 9 mg lycopene, from about 15 mg to about 450 mg olive fruit extract (10% total phenolic content by weight), from about 2.5 mg to about 75 mg grape seed extract, and/or from about 30 mg to about 900 mg vitamin C. For example, a dietary supplement of a Supplement Formulation B can be formulated into a single composition (e.g., a capsule) that has from about 5 mg to about 150 mg α-tocopherol, from about 0.7 mg to about 20 mg β-tocopherol, from about 10 mg to about 300 mg γ-tocopherol, from about 2.5 mg to about 75 mg δ-tocopherol, from about 0.01 mg to about 0.3 mg α-carotene, from about 0.2 mg to about 6 mg β-carotene, from about 0.02 mg to about 0.6 mg criptoxanthin, from about 0.01 mg to about 0.3 mg zeaxanthin, from about 0.01 mg to about 0.3 mg lutein, from about 0.3 mg to about 9 mg lycopene, from about 15 mg to about 450 mg olive fruit extract (10% total phenolic content by weight), from about 2.5 mg to about 75 mg grape seed extract, and from about 30 mg to about 900 mg vitamin C.

In other cases, a dietary supplement of a Supplement Formulation B can be formulated into a single composition (e.g., a capsule) that has from about 25 mg to about 100 mg α-tocopherol, from about 3.5 mg to about 13 mg β-tocopherol, from about 50 mg to about 200 mg γ-tocopherol, from about 12 mg to about 50 mg δ-tocopherol, from about 0.05 mg to about 0.2 mg α-carotene, from about 1 mg to about 4 mg β-carotene, from about 0.1 mg to about 0.4 mg criptoxanthin, from about 0.05 mg to about 0.2 mg zeaxanthin, from about 0.05 mg to about 0.2 mg lutein, from about 1.5 mg to about 6 mg lycopene, from about 75 mg to about 300 mg olive fruit extract (10% total phenolic content by weight), from about 12 mg to about 50 mg grape seed extract, and/or from about 150 mg to about 600 mg vitamin C. For example, a dietary supplement of a Supplement Formulation B can be formulated into a single composition (e.g., a capsule) that has from about 25 mg to about 100 mg α-tocopherol, from about 3.5 mg to about 13 mg β-tocopherol, from about 50 mg to about 200 mg γ-tocopherol, from about 12 mg to about 50 mg δ-tocopherol, from about 0.05 mg to about 0.2 mg α-carotene, from about 1 mg to about 4 mg β-carotene, from about 0.1 mg to about 0.4 mg criptoxanthin, from about 0.05 mg to about 0.2 mg zeaxanthin, from about 0.05 mg to about 0.2 mg lutein, from about 1.5 mg to about 6 mg lycopene, from about 75 mg to about 300 mg olive fruit extract (10% total phenolic content by weight), from about 12 mg to about 50 mg grape seed extract, and from about 150 mg to about 600 mg vitamin C.

In other cases, a dietary supplement of a Supplement Formulation B can be formulated into a single composition (e.g., a capsule) that has from about 40 mg to about 75 mg α-tocopherol, from about 5 mg to about 10 mg β-tocopherol, from about 80 mg to about 150 mg γ-tocopherol, from about 20 mg to about 40 mg δ-tocopherol, from about 0.08 mg to about 0.15 mg α-carotene, from about 1.5 mg to about 3 mg β-carotene, from about 0.15 mg to about 0.3 mg criptoxanthin, from about 0.08 mg to about 0.15 mg zeaxanthin, from about 0.08 mg to about 0.15 mg lutein, from about 2.5 mg to about 4.5 mg lycopene, from about 120 mg to about 225 mg olive fruit extract (10% total phenolic content by weight), from about 20 mg to about 40 mg grape seed extract, and/or from about 240 mg to about 450 mg vitamin C. For example, a dietary supplement of a Supplement Formulation B can be formulated into a single composition (e.g., a capsule) that has from about 40 mg to about 75 mg α-tocopherol, from about 5 mg to about 10 mg β-tocopherol, from about 80 mg to about 150 mg γ-tocopherol, from about 20 mg to about 40 mg δ-tocopherol, from about 0.08 mg to about 0.15 mg α-carotene, from about 1.5 mg to about 3 mg β-carotene, from about 0.15 mg to about 0.3 mg criptoxanthin, from about 0.08 mg to about 0.15 mg zeaxanthin, from about 0.08 mg to about 0.15 mg lutein, from about 2.5 mg to about 4.5 mg lycopene, from about 120 mg to about 225 mg olive fruit extract (10% total phenolic content by weight), from about 20 mg to about 40 mg grape seed extract, and from about 240 mg to about 450 mg vitamin C.

In some cases, a dietary supplement of a Supplement Formulation B can include ingredients having the ability to reduce the risk of cardiovascular disease, reduce the risk of cataracts, improve immune system function, improve vision (eye) function, improve regulation of gene expression, improve body and organ growth and development, improve red blood cell production, reduce lipid peroxidation markers, increase resistance of LDL to oxidation, reduce DNA peroxidation markers, reduce inflammation, reduce UV-light sensitivity or UV-light induced skin erythema, reduce risk of prostate cancer, reduce risk of breast cancer, reduce wrinkle formation, reduce cellular damage, increase protection against free radical DNA damage in cells, increase protection against sun damage or environmental aging, stimulate phase II detoxification enzyme activity, inhibit tumor invasion and angiogenesis, and/or reduce risk of stroke.

In some cases, a dietary supplement of a Supplement Formulation B can be administered to a mammal (e.g., a human) to reduce the risk of cardiovascular disease, reduce the risk of cataracts, improve immune system function, improve vision (eye) function, improve regulation of gene expression, improve body and organ growth and development, improve red blood cell production, reduce expression of lipid peroxidation markers, increase resistance of LDL to oxidation, reduce expression of DNA peroxidation markers, reduce inflammation, reduce UV-light sensitivity or UV-light induced skin erythema, reduce risk of prostate cancer, reduce risk of breast cancer, reduce wrinkle formation, reduce cellular damage, increase protection against free radical DNA damage in cells, increase protection against sun damage or environmental aging, stimulate phase II detoxification enzyme activity, inhibit tumor invasion and angiogenesis, and/or reduce risk of stroke.

In one example, a dietary supplement of a Supplement Formulation B can include:

Formula Example

| Vitamin A (as beta carotene) | 2500 IU |
|---|---|
| alpha-Carotene | 35 μg |
| Cryptoxanthin | 7 μg |
| Zeaxanthin | 7 μg |
| Lutein | 7 μg |
| Lycopene | 3 mg |
| Vitamin C (as ascorbic acid) | 300 mg |
| Vitamin E (as d-alpha tocopherol) | 60 IU |
| beta-Tocopherol | 0.38 mg |
| gamma-Tocopherol | 1 mg |
| delta-Tocopherol | 0.38 mg |
| Olive Extract | 150 mg |
| Grape Seed Extract | 25 mg |

In another example, a daily dose of dietary supplement of a Supplement Formulation B can be designed to provide the following effective amounts:

Formula Example

| Vitamin A (as beta carotene) | 2500 IU |
|---|---|
| Vitamin C (as ascorbic acid) | 300 mg |
| Vitamin E (as d-alpha tocopherol) | 60 IU |

-continued

| Calcium (as calcium carbonate) | 75 mg |
|---|---|
| Mixed Carotenoids Blend | 1000 μg |
| alpha-carotene | |
| cryptoxanthin | |
| zeaxanthin | |
| lutein | |
| Mixed Tocopherols | 32 mg |
| d-beta | |
| d-gamma | |
| d-delta | |
| Lycopene | 3 mg |
| Olive Fruit Extract | 150 mg |
| Grape Seed Extract | 25 mg |

In some cases, a dietary supplement of a Supplement Formulation B can be made and used as described in International Patent Application No. PCT/US2010/045271 or U.S. Pat. No. 8,491,939, both of which are herein incorporated by reference in their entirety. For example, a dietary supplement of a Supplement Formulation B can be made to have the ingredients as set forth in International Patent Application No. PCT/US2010/045271 or U.S. Pat. No. 8,491,939.

Supplement Formulation C

Supplement Formulation C can provide ingredients useful for reducing pain, inflammation, discomfort, and/or stiffness associated with inflammatory conditions such as arthritis and osteoarthritis. In general, a dietary supplement of a Supplement Formulation C can include, without limitation, one or more of an iridoid, a ginger component, an anthocyanin, a coumarin, a curcuminoid, and a green tea extract. In some cases, a dietary supplement of a Supplement Formulation C can contain a Devil's Claw extract, a ginger component, an *Aronia* extract, an *Angelica gigas* extract, a turmeric extract, and/or a green tea extract. In some cases, a dietary supplement of a Supplement Formulation C can contain a Devil's Claw extract, an *Aronia* extract, an *Angelica gigas* extract, and a turmeric extract.

Iridoid

Examples of iridoids include, without limitation, harpagoside, loganin, sweroside, vogeloside, and epi-vogeloside. In some cases, the iridoid of a dietary supplement of a Supplement Formulation C can be harpagoside:

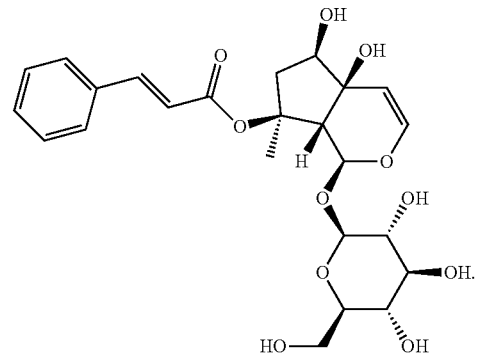 [SMILES: C[C@]1(OC(=O)/C=C/c2ccccc2)C[C@@H](O)[C@]2(O)C=CO[C@@H](O[C@@H]3O[C@H](CO)[C@@H](O)[C@H](O)[C@H]3O)[C@@H]21]

Iridoids can be synthesized or derivatized from natural sources. In some cases, an iridoid can be a component of a plant extract. For example, an iridoid can be a component of an extract of Devil's Claw. A Devil's Claw extract can be made using an ethanol or hydroalcoholic extraction. In some cases, iridoids and/or plant extracts containing iridoids (e.g., Devil's Claw) can be obtained commercially. For example, Devil's Claw extract can be obtained from Pharmline Inc. (NY, USA).

As described herein, a dietary supplement of a Supplement Formulation C can contain one or more than one iridoid. In some cases, a dietary supplement of a Supplement Formulation C can contain any appropriate amount of an iridoid. For example, at least 5 percent (e.g., at least 10, 15, 20, 25, 30, 35, 40, 50, 60, 70, 80, or 90 percent) of a dietary supplement of a Supplement Formulation C can be an iridoid. In some cases, a dietary supplement of a Supplement Formulation C can contain between 5 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of an iridoid.

In some cases, a dietary supplement of a Supplement Formulation C can be formulated into a single composition (e.g., a capsule or tablet) having between 300 mg and 3000 mg (e.g., between 300 and 2500 mg, between 300 mg and 2000 mg, between 300 mg and 1500 mg, between 300 mg and 1250 mg, between 300 mg and 900 mg, between 400 mg and 3000 mg, between 500 mg and 3000 mg, between 650 mg and 3000 mg, between 700 mg and 3000 mg, between 775 mg and 3000 mg, between 400 mg and 2000 mg, between 500 mg and 1500 mg, between 600 mg and 1200 mg, between 700 mg and 800 mg) of an iridoid.

In some cases, the iridoid of a dietary supplement of a Supplement Formulation C can be a component of a plant extract. For example, the iridoid can be a component of a Devil's Claw extract. In some cases, the Devil's Claw extract is obtained using standard extraction techniques. In some cases, a dietary supplement of a Supplement Formulation C can contain any appropriate amount of a plant extract, such as a standard Devil's claw extract. For example, at least 5 percent (e.g., at least 10, 15, 20, 25, 30, 35, 40, 50, 60, 70, 80, or 90 percent) of a dietary supplement of a Supplement Formulation C can be the plant extract. Typically, a dietary supplement of a Supplement Formulation C contains between 50 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of the plant extract. In some cases, a dietary supplement of a Supplement Formulation C can be formulated to contain an amount of the plant extract such that a daily dose of between 300 mg and 3000 mg (e.g., between 300 and 2500 mg, between 300 mg and 2000 mg, between 300 mg and 1500 mg, between 300 mg and 1250 mg, between 300 mg and 900 mg, between 400 mg and 3000 mg, between 500 mg and 3000 mg, between 650 mg and 3000 mg, between 700 mg and 3000 mg, between 775 mg and 3000 mg, between 400 mg and 2000 mg, between 500 mg and 1500 mg, between 600 mg and 1200 mg, between 700 mg and 800 mg) of the plant extract is conveniently administered.

Ginger

As described herein, a dietary supplement of a Supplement Formulation C can contain a ginger component. Examples of ginger components include, without limitation, dried ginger (e.g., dried gingerroot), ginger oil, and ginger extracts. In some cases, a ginger component can be a ginger root extract. A ginger component can be obtained from any of the estimated 1300 species of plants that belong to the Zingiberaceae family. Typically, a ginger component is derived from *Zingiber officinale, Alpinia officnarum*, or *Alpinia galanga.*

Any appropriate method can be used to prepare a ginger component. For example, standard harvesting and drying methods can be used to prepare dried gingerroot. Ginger oil can be obtained using standard methods and processed with cellulose for making tablet or powder compositions. A ginger extract can be made using an ethanol or hydroalcoholic extraction. Such extracts can be standardized to, for example, 5 to 75 percent gingerol or shogaol. In some cases, ginger components can be obtained commercially. For example, dried ginger, ginger oil, and ginger extract can be obtained from BattleChem Inc., (CA, USA).

In some cases, a dietary supplement of a Supplement Formulation C can contain one or more than one ginger component. For example, a dietary supplement of a Supplement Formulation C can contain dried gingerroot as well as a ginger root extract. In some cases, a dietary supplement of a Supplement Formulation C can contain any appropriate amount of a ginger component. For example, at least 5 percent (e.g., at least 10, 15, 20, 25, 30, 35, 40, 50, 60, 70, 80, or 90 percent) of a dietary supplement of a Supplement Formulation C can be a ginger component. In some cases, a dietary supplement of a Supplement Formulation C can contain between 5 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of a ginger component.

In some cases, a dietary supplement of a Supplement Formulation C can be formulated into a single composition (e.g., a capsule or tablet) designed to contain an amount of a ginger component such that a daily dose of between 50 mg to 1000 mg ginger component (e.g., between 50 mg and 900 mg between 50 mg and 850 mg, between 50 mg and 750 mg, between 100 mg and 1000 mg, between 200 mg and 1000 mg, between 350 mg and 1000 mg, between 450 mg and 1000 mg, between 600 mg and 1000 mg, between 700 mg and 1000 mg, between 300 mg to 900 mg, and between 600 mg and 800 mg ginger component) can be conveniently administered. For example, a dietary supplement of a Supplement Formulation C can be formulated to contain 180 mg of a ginger component. When ginger root extract is used, a dietary supplement of a Supplement Formulation C can be formulated to contain an amount of ginger root extract such that a daily dose of between 50 mg to 1000 mg ginger root extract (e.g., between 50 mg and 900 mg between 50 mg and 850 mg, between 50 mg and 750 mg, between 100 mg and 1000 mg, between 200 mg and 1000 mg, between 350 mg and 1000 mg, between 450 mg and 1000 mg, between 600 mg and 1000 mg, between 700 mg and 1000 mg, between 300 mg to 900 mg, and between 600 mg and 800 mg ginger root extract) can be conveniently administered.

Anthocyanin

As described herein, a dietary supplement of a Supplement Formulation C can contain an anthocyanin. Examples of anthocyanins include, without limitation, aurantinidin, cyaniding, delphinidin, europinidin, luteolinidin, pelargonidin, malvidin, peonidin, petunidin, and rosinidin.

Anthocyanins can be synthesized or derivatized from natural sources. In some cases, an anthocyanin can be a component of a plant extract. For example, an anthocyanin can be a component of an extract from an *Aronia* species. In some cases, the *Aronia* species is *Aronia melanocarpa*. An extract of *Aronia* can be made using an ethanol or hydroalcoholic extraction. In some cases, anthocyanins and plant extracts containing anthocyanins (e.g., *Aronia melanocarpa*) can be obtained commercially. For example, an *Aronia melanocarpa* extract can be obtained from Kaden Biochemicals GmbH (Germany).

In some cases, a dietary supplement of a Supplement Formulation C can contain one or more than one anthocyanin. In some cases, a dietary supplement of a Supplement Formulation C can contain any appropriate amount of an anthocyanin. For example, at least 5 percent (e.g., at least 10, 15, 20, 25, 30, 35, 40, 50, 60, 70, 80, or 90 percent) of a dietary supplement of a Supplement Formulation C can be an anthocyanin. In some cases, a dietary supplement of a Supplement Formulation C can contain between 5 mg and 500 mg (e.g., between 5 mg and 450 mg, between 5 mg and 400 mg, between 5 mg and 350 mg, between 5 mg and 320 mg, between 5 mg and 300 mg, between 5 mg and 250 mg, between 5 mg and 150 mg, between 5 mg and 100 mg, between 5 mg and 500 mg, between 10 mg and 500 mg, between 25 mg and 500 mg, between 35 mg and 500 mg, between 50 mg and 500 mg, between 62.5 mg and 500 mg, between 70 mg and 500 mg, between 5 mg and 100 mg, between 25 mg and 500 mg, between 50 mg and 400 mg, and between 100 mg and 300 mg) of an anthocyanin. In some cases, a dietary supplement of a Supplement Formulation C can be formulated to contain an amount of an anthocyanin such that a daily dose of between 100 mg and 1000 mg (e.g., between 100 and 900 mg, between 100 mg and 800 mg, between 100 mg and 600 mg, between 100 mg and 500 mg, between 100 mg and 400 mg, between 150 mg and 1000 mg, between 250 mg and 1000 mg, between 300 mg and 1000 mg, between 350 mg and 1000 mg, 200 mg and 900 mg, between 250 mg and 800 mg, between 300 mg and 600 mg, and between 350 mg and 500 mg) of the anthocyanin can be conveniently administered.

In some cases, the anthocyanin of a dietary supplement of a Supplement Formulation C can be a component of a plant extract. For example, the anthocyanin can be a component of an *Aronia* extract (e.g., *Aronia melanocarpa*). In some cases, the *Aronia* extract is obtained using standard extraction techniques. In some cases, a dietary supplement of a Supplement Formulation C can contain any appropriate amount of a plant extract, such as a standard *Aronia melanocarpa* extract. For example, at least 5 percent (e.g., at least 10, 15, 20, 25, 30, 35, 40, 50, 60, 70, 80, or 90 percent) of a dietary supplement of a Supplement Formulation C can be the plant extract. In some cases, a dietary supplement of a Supplement Formulation C can contain between 5 mg and 500 mg (e.g., between 5 mg and 450 mg, between 5 mg and 400 mg, between 5 mg and 350 mg, between 5 mg and 320 mg, between 5 mg and 300 mg, between 5 mg and 250 mg, between 5 mg and 150 mg, between 5 mg and 100 mg, between 5 mg and 500 mg, between 10 mg and 500 mg, between 25 mg and 500 mg, between 35 mg and 500 mg, between 50 mg and 500 mg, between 62.5 mg and 500 mg, between 70 mg and 500 mg, between 5 mg and 100 mg, between 25 mg and 500 mg, between 50 mg and 400 mg, and between 100 mg and 300 mg) of the plant extract. In some cases, a dietary supplement of a Supplement Formulation C can be formulated to contain an amount of the plant extract such that a daily dose of between 100 mg and 1000 mg (e.g., between 100 and 900 mg, between 100 mg and 800 mg, between 100 mg and 600 mg, between 100 mg and 500 mg, between 100 mg and 400 mg, between 150 mg and 1000 mg, between 250 mg and 1000 mg, between 300 mg and 1000 mg, between 350 mg and 1000 mg, 200 mg and 900 mg, between 250 mg and 800 mg, between 300 mg and 600 mg, and between 350 mg and 500 mg) of the plant extract can be conveniently administered.

Coumarin

As described herein, a dietary supplement of a Supplement Formulation C can contain a coumarin. Examples of coumarins include, without limitation, decursin, decursinol, nodakenetin, umbelliferon, nodakenin, and β-sitosterol. In some cases, the courmarin can be decursinol:

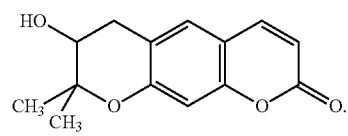 [SMILES: CC1(C)Oc2cc3oc(=O)ccc3cc2CC1O]

Coumarins can be synthesized or derivatized from natural sources. In some cases, a coumarin can be a component of a plant extract. For example, a coumarin can be a component of an extract of *Angelica gigas*. In some cases, the extract of *Angelica gigas* is a root extract. An extract of *Angelica gigas* can be made using an ethanol or hydroalcoholic extraction. In some cases, coumarins and plant extracts containing coumarins (e.g., *Angelica gigas*) can be obtained commercially. For example, *Angelica gigas* root extract can be obtained from FCC Inc., (NJ, USA).

In some cases, a dietary supplement of a Supplement Formulation C can contain one or more than one coumarin. A dietary supplement of a Supplement Formulation C can contain any appropriate amount of a coumarin. For example, at least 5 percent (e.g., at least 10, 15, 20, 25, 30, 35, 40, 50, 60, 70, 80, or 90 percent) of a dietary supplement of a Supplement Formulation C can be an anthocyanin. In some cases, a dietary supplement of a Supplement Formulation C can contain between 5 mg and 500 mg (e.g., between 5 mg and 450 mg, between 5 mg and 400 mg, between 5 mg and 350 mg, between 5 mg and 300 mg, between 5 mg and 250 mg, between 5 mg and 150 mg, between 5 mg and 100 mg, between 5 mg and 75 mg, between 10 mg and 500 mg, between 25 mg and 500 mg, between 35 mg and 500 mg, between 50 mg and 500 mg, between 10 mg and 400 mg, between 25 mg and 300 mg, and between 30 mg and 100 mg) of a coumarin. In some cases, a dietary supplement of a Supplement Formulation C can be formulated to contain an amount of a coumarin such that a daily dose of between 50 mg and 1000 mg (e.g., between 50 and 900 mg, between 50 mg and 800 mg, between 50 mg and 600 mg, between 50 mg and 500 mg, between 50 mg and 400 mg, between 50 mg and 300 mg, between 100 mg and 1000 mg, between 150 mg and 1000 mg, between 200 mg and 1000 mg, 75 mg and 900 mg, between 100 mg and 800 mg, between 125 mg and 600 mg, and between 150 mg and 300 mg) of the coumarin can be conveniently administered.

In some cases, the coumarin of a dietary supplement of a Supplement Formulation C can be a component of a plant extract. For example, the coumarin can be a component of an *Angelica gigas* extract (e.g., a root extract of *Angelica gigas*). In some cases, the *Angelica gigas* extract is obtained using standard extraction techniques. In some cases, a dietary supplement of a Supplement Formulation C can contain any appropriate amount of a plant extract, such as a standard *Angelica gigas* root extract. For example, at least 5 percent (e.g., at least 10, 15, 20, 25, 30, 35, 40, 50, 60, 70, 80, or 90 percent) of a dietary supplement of a Supplement Formulation C can be the plant extract. In some cases, a dietary supplement of a Supplement Formulation C can contain between 5 mg and 500 mg (e.g., between 5 mg and 450 mg, between 5 mg and 400 mg, between 5 mg and 350 mg, between 5 mg and 300 mg, between 5 mg and 250 mg, between 5 mg and 150 mg, between 5 mg and 100 mg, between 5 mg and 75 mg, between 10 mg and 500 mg, between 25 mg and 500 mg, between 35 mg and 500 mg, between 50 mg and 500 mg, between 10 mg and 400 mg, between 25 mg and 300 mg, and between 30 mg and 100 mg) of the plant extract. In some cases, a dietary supplement of a Supplement Formulation C can be formulated to contain an amount of the plant extract such that a daily dose of between 50 mg and 1000 mg (e.g., between 50 and 900 mg, between 50 mg and 800 mg, between 50 mg and 600 mg, between 50 mg and 500 mg, between 50 mg and 400 mg, between 50 mg and 300 mg, between 100 mg and 1000 mg, between 150 mg and 1000 mg, between 200 mg and 1000 mg, 75 mg and 900 mg, between 100 mg and 800 mg, between 125 mg and 600 mg, and between 150 mg and 300 mg) of the plant extract can be conveniently administered.

Curcuminoid

As described herein, a dietary supplement of a Supplement Formulation C can contain a curcuminoid. An example of a curcuminoid is curcumin:

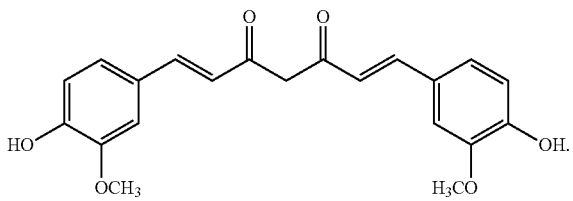 [SMILES: COc1cc(/C=C/C(=O)CC(=O)/C=C/c2ccc(O)c(OC)c2)ccc1O]

Curcuminoids can be synthesized or derivatized from natural sources. In some cases, a curcuminoid can be a component of a plant extract. For example, a curcuminoid can be a component of an extract of turmeric. An extract of turmeric can be made using an ethanol or hydroalcoholic extraction. In some cases, curcuminoid and plant extracts containing curcuminoid (e.g., turmeric) can be obtained commercially. For example, turmeric extract or curcumin can be obtained from BattleChem Inc., (CA, USA).

In some cases, a dietary supplement of a Supplement Formulation C can contain one or more than one curcuminoid. A dietary supplement of a Supplement Formulation C can contain any appropriate amount of a curcuminoid. For example, at least 5 percent (e.g., at least 10, 15, 20, 25, 30, 35, 40, 50, 60, 70, 80, or 90 percent) of a dietary supplement of a Supplement Formulation C can be a curcuminoid. In some cases, a dietary supplement of a Supplement Formulation C can contain between 1 mg and 300 mg (e.g., between 1 mg and 250 mg, between 1 mg and 200 mg, between 1 mg and 150 mg, between 1 mg and 100 mg, between 1 mg and 50 mg, between 5 mg and 300 mg, between 10 mg and 300 mg, between 20 mg and 300 mg, between 10 mg and 100 mg, and between 20 mg and 60 mg) of a curcuminoid. In some cases, a dietary supplement of a Supplement Formulation C can be formulated to contain an amount of a curcuminoid such that a daily dose of between 25 mg and 500 mg (e.g., between 25 mg and 450 mg, between 25 mg and 400 mg, between 25 mg and 350 mg, between 25 mg and 300 mg, between 25 mg and 250 mg, between 10 mg and 500 mg, between 50 mg and 500 mg, between 75 mg and 500 mg, between 90 mg and 500 mg, between 10 mg and 400 mg, between 25 mg and 300 mg, and between 50 mg and 150 mg) of the curcuminoid.

In some cases, the curcuminoid can be a component of a plant extract. For example, the curcuminoid of a dietary supplement of a Supplement Formulation C can be a component of a turmeric extract. In some cases, the turmeric extract is obtained using standard extraction techniques. In some cases, a dietary supplement of a Supplement Formulation C can contain any appropriate amount of a plant extract, such as a standard turmeric extract. For example, at least 5 percent (e.g., at least 10, 15, 20, 25, 30, 35, 40, 50, 60, 70, 80, or 90 percent) of a dietary supplement of a Supplement Formulation C can be the plant extract. Typically, a dietary supplement of a Supplement Formulation C contains between 1 mg and 300 mg (e.g., between 1 mg and 250 mg, between 1 mg and 200 mg, between 1 mg and 150 mg, between 1 mg and 100 mg, between 1 mg and 50 mg, between 5 mg and 300 mg, between 10 mg and 300 mg, between 20 mg and 300 mg, between 10 mg and 100 mg, and between 20 mg and 60 mg) of the plant extract. In some cases, a dietary supplement of a Supplement Formulation C can be formulated to contain an amount of the plant extract such that a daily dose of between 25 mg and 500 mg (e.g., between 25 mg and 450 mg, between 25 mg and 400 mg, between 25 mg and 350 mg, between 25 mg and 300 mg, between 25 mg and 250 mg, between 10 mg and 500 mg, between 50 mg and 500 mg, between 75 mg and 500 mg, between 90 mg and 500 mg, between 10 mg and 400 mg, between 25 mg and 300 mg, and between 50 mg and 150 mg) of the plant extract can be conveniently administered.

Green Tea

As described herein, a dietary supplement of a Supplement Formulation C can contain a green tea extract. A green tea extract is an extract derived from *Camellia sinensis*. Any appropriate method can be used to obtain a green tea extract. For example, a green tea extract can be obtained by drying (e.g., freeze drying or spray drying) a liquor from an alcoholic, hydroalcoholic, or other hydrocarbon extraction. In some cases, a green tea extract can be dried and standardized to contain at least about 25 percent total phenols. A green tea extract can contain catechin, epicatechin, gallocatechin, epigallocatechin, epicatechin gallate, epicatchingallate, and epigallocatechin gallate. In some cases, a dietary supplement of a Supplement Formulation C can contain a green tea extract having at least about 15 percent of catechin group compounds. A green tea extract can be caffeinated or decaffeinated. In some cases, a green tea extract can be obtained commercially. For example, a green tea extract can be obtained from Buckton Scott Nutrition, Inc. (Fairfield, N.J.), Pure World, Inc. (Hackensack, N.J.), Sabinsa Corporation (Piscatawayt, N.J.), or Stauber Performance Ingredients Inc., (Fullerton, Calif.).

In some cases, a dietary supplement of a Supplement Formulation C can contain one or more than one green tea extract. A dietary supplement of a Supplement Formulation C can contain any appropriate amount of a green tea extract. For example, at least 5 percent (e.g., at least 10, 15, 20, 25, 30, 35, 40, 50, 60, 70, 80, or 90 percent) of a dietary supplement of a Supplement Formulation C can be a green tea extract. In some cases, a dietary supplement of a Supplement Formulation C can contain between 5 mg and 500 mg (e.g., between 5 mg and 450 mg, between 5 mg and 400 mg, between 5 mg and 350 mg, between 5 mg and 300 mg, between 5 mg and 250 mg, between 5 mg and 150 mg, between 5 mg and 100 mg, between 5 mg and 75 mg, between 10 mg and 500 mg, between 25 mg and 500 mg, between 35 mg and 500 mg, between 50 mg and 500 mg, between 10 mg and 400 mg, between 25 mg and 300 mg, and between 30 mg and 100 mg) of a green tea extract. In some cases, a dietary supplement of a Supplement Formulation C can be formulated to contain an amount of a green tea extract such that a daily dose of between 50 mg and 1000 mg (e.g., between 50 and 900 mg, between 50 mg and 800 mg, between 50 mg and 600 mg, between 50 mg and 500 mg, between 50 mg and 400 mg, between 50 mg and 300 mg, between 100 mg and 1000 mg, between 150 mg and 1000 mg, between 200 mg and 1000 mg, 75 mg and 900 mg, between 100 mg and 800 mg, between 125 mg and 600 mg, and between 150 mg and 300 mg) of a green tea extract can be conveniently administered. For example, a dietary supplement of a Supplement Formulation C can be formulated to contain between 50 and 60 mg (e.g., about 60 mg) of a green tea extract.

In one example, a dietary supplement of a Supplement Formulation C can include:

Formula Example

| | |
|---|---|
| Turmeric | 26 mg |
| Ginger Root Extract | 180 mg |
| Green Tea Extract | 60 mg |
| Aroma (Chokeberry) Powder | 90 mg |
| Angelica gigas root (Decursinol) | 50 mg |
| Devil's Claw Extract | 200 mg |

Formula Example 2

| | |
|---|---|
| Turmeric | 6 mg |
| Ginger Root Extract | 42 mg |
| Green Tea Extract | 14 mg |
| Aroma (Chokeberry) Powder | 21 mg |
| Angelica gigas root (Decursinol) | 12 mg |
| Devil's Claw Extract | 46 mg |

In some cases, a dietary supplement of a Supplement Formulation C can include a blend of two or more of turmeric, ginger root extract, green tea extract, *Aronia* powder, *Angelica gigas* root, and Devil's Claw extract. In some cases, a dietary supplement of a Supplement Formulation C can include a blend that includes turmeric, ginger root extract, green tea (leaf) extract, and Devil's Claw extract. In some cases, a daily dose of a dietary supplement of a Supplement Formulation C can include a blend containing from about 100 mg to about 1000 mg (e.g., from about 100 mg to about 300 mg, from about 100 mg to about 500 mg, from about 500 mg to about 100 mg, from about 500 mg to about 750 mg, or from about 500 mg to about 1000 mg) of the total blend.

In one example, a daily dose of a dietary supplement of a Supplement Formulation C can be designed to provide the following effective amounts:

| | |
|---|---|
| Devil's Claw Extract, Ginger Root Extract, Chokeberry Extract, Green Tea Leaf Extract, *Angelica Gigas* Root, And Tumeric Root Extract Blend | 605 mg |

In some cases, a dietary supplement of a Supplement Formulation C can be made and used as described in International Patent Application No. PCT/US2010/045260, which is herein incorporated by reference in its entirety. For example, a dietary supplement of a Supplement Formulation C can be made to have the ingredients as set forth in International Patent Application No. PCT/US2010/045260.

Supplement Formulation D

A dietary supplement of a Supplement Formulation D can include, without limitation, fish oil containing an omega 3 fatty acid such as eicosapentaenoic acid (EPA) and/or docosahexaenoic acid (DHA). For example, a dietary supplement of a Supplement Formulation D can contain fish oil obtained, for example, from salmon, herring, mackerel, or tuna. Fish oils can contain varying amounts of EPA and DHA. In some cases, if it desired to have a fish oil with an emphasis in EPA, a dietary supplement of a Supplement Formulation D can include fish oil having a ratio of EPA to DHA of about 20 to 1, 10 to 1, 9 to 1, 8 to 1, 7, to 1, 6 to 1, 5 to 1, 4 to 1, 3 to 1, 2 to 1, or 1 to 1. In other cases, if it desired to have more DHA, a dietary supplement of a Supplement Formulation D can include fish oil having a ratio of EPA to DHA of about 1 to 5, 2 to 5, 3 to 5, 4 to 5, or 1 to 1. Fish oils can be obtained commercially from a variety of providers.

In some cases, a dietary supplement of a Supplement Formulation D can contain between 5 mg and 5000 mg (e.g., between 5 mg and 4500 mg, between 5 mg and 4000 mg, between 5 mg and 3500 mg, between 5 mg and 3200 mg, between 5 mg and 3000 mg, between 5 mg and 2500 mg, between 5 mg and 1500 mg, between 5 mg and 1000 mg, between 5 mg and 750 mg, between 5 mg and 600 mg, between 5 mg and 500 mg, between 5 mg and 400 mg, between 5 mg and 300 mg, between 5 mg and 250 mg, between 5 mg and 100 mg, between 5 mg and 50 mg, between 25 mg and 5000 mg, between 50 mg and 5000 mg, between 100 mg and 5000 mg, between 250 mg and 5000 mg, between 350 mg and 5000 mg, between 500 mg and 5000 mg, between 625 mg and 5000 mg, between 700 mg and 5000 mg, between 750 mg and 1300 mg, between 900 mg and 5000 mg, between 1000 mg and 5000 mg, between 1500 mg and 5000 mg, between 2000 mg and 5000 mg, between 3500 mg and 5000 mg, between 5 mg and 1000 mg, between 25 mg and 500 mg, between 50 mg and 400 mg, between 100 mg and 300 mg, and between 150 mg and 250 mg) of fish oil. In some cases, a dietary supplement of a Supplement Formulation D can be formulated to contain an amount of the fish oil such that a daily dose of between 300 mg and 3000 mg (e.g., between 300 and 2500 mg, between 300 mg and 2000 mg, between 300 mg and 1500 mg, between 300 mg and 1250 mg, between 300 mg and 900 mg, between 400 mg and 3000 mg, between 500 mg and 3000 mg, between 650 mg and 3000 mg, between 700 mg and 3000 mg, between 775 mg and 3000 mg, between 400 mg and 2000 mg, between 500 mg and 1500 mg, between 600 mg and 1200 mg, or between 700 mg and 800 mg) of the fish oil can be conveniently administered.

In some embodiments, a dietary supplement of a Supplement Formulation D can include a fish oil concentrate containing a higher ratio of EPA to DHA, for example, a fish oil concentrate (2 g) containing EPA (1000 mg) and DHA (100 mg). Without being bound by any theory, such a supplement may aid in the anti-inflammatory and cardiovascular health benefits of the formulation. In some cases, a dietary supplement of a Supplement Formulation D can include a fish oil concentrate containing a higher ratio of DHA to EPA, for example, a fish oil concentrate (1470 mg) containing EPA (270 mg) and DHA (660 mg). Without being bound by any theory, such a supplement may aid in the brain health, eye health, and cardiovascular health benefits of the formulation In another example, a daily dose of a dietary supplement of a Supplement Formulation E can be designed to provide the following effective amounts:

Example Formula

| Fish Oil Concentrate containing: | 2000 mg |
|---|---|
| (1) EPA | 1000 mg |
| (2) DHA | 100 mg |

Supplement Formulation E

A dietary supplement of a Supplement Formulation E can include, without limitation, at least one flavonoid source and an enzyme. Examples of flavonoid sources that can be included within a dietary supplement of a Supplement Formulation E include, without limitation, grape seed extracts, grape skin extracts, *Ginkgo biloba* extracts, quercetin, and bilberry extracts. A flavonoid source can be derived from any appropriate source and may include synthetic or purified flavonoids from known sources. For example, catechins, procyanidins, proanthocyanidins, quercetin, rutin, and glycosidic forms of flavonoids can be used to make a dietary supplement of a Supplement Formulation E. The flavonoid source may also be, for example, one or more flavonoids determined to be highly active alone or as a combination wherein the flavonoid is isolated from a complex mixture, such as a plant extract, containing numerous flavonoids. Examples of enzymes that can be included within a dietary supplement of a Supplement Formulation E include, without limitation, fungal proteases, acid stable proteases, bromelain, pepsin, papain, neutral stable proteases, alkaline stable proteases, and combinations thereof (e.g., a blend of Fungal Protease 20053, Fungal Protease 20054, an acid stable protease, and bromelain). In some cases, a dietary supplement of a Supplement Formulation E can be effective for inhibiting blood platelet activity and LDL cholesterol oxidation in a mammal at a dosage of about 30 mg/Kg or less.

In some cases, a dietary supplement of a Supplement Formulation E can include, without limitation, fruit extracts, vegetable extracts, digestive enzymes, herbs, flavonoids, antioxidants, and combinations thereof. In some cases, a dietary supplement of a Supplement Formulation E can include one or more of the following: grape seed extract, grape skin extract, *Ginkgo biloba* extract, bilberry extract, quercetin and an enzyme blend. A dietary supplement of a Supplement Formulation E may be formulated by weight in the following manner: grape seed extract at 12% w/w, grape skin extract at 20% w/w, *Ginkgo biloba* extract at 10% w/w, bilberry extract at 10% w/w, quercetin at 24% w/w, and an enzyme blend at 24% w/w. In some cases, a dietary supplement of a Supplement Formulation E can be PROVEXCV®, which is a dietary supplement available from Melaleuca, Inc. (Idaho Falls, Id.).

One example formula is as follows:

| Ingredient | % Formulation | Amount |
|---|---|---|
| Grape Seed Extract | 12% | 45 mg |
| *Ginkgo Biloba* Extract | 10% | 38 mg |
| Bilberry Extract | 10% | 38 mg |
| Grape Skin Extract | 20% | 76 mg |
| Quercetin | 24% | 92 mg |
| Enzyme Blend | 24% | 91 mg |
| Total | 100% | 380 mg |

An enzyme blend for according to the above formula can contain the following enzymes (Table 2):

TABLE 2

Enzyme blend.

| Ingredient | % of Enzyme blend | Activity Units |
|---|---|---|
| Fungal Protease 20053 | 25% | 11,250 HUT |
| Fungal Protease 20054 | 25% | 11,250 HUT |
| Acid Stable Protease | 25% | 3,375 SAPU |
| Bromelain | 25% | 5,760,000 PU |
| Total | 100% | |

The fungal proteases 20053 and 20054 are enzyme mixtures of acid, neutral, and alkaline protease enzymes. HUT activity is the activity of an enzyme measured in the FCC HUT assay, which is based on the hydrolysis of denatured hemoglobin. One HUT unit is defined as that amount of enzyme that produces a hydrosylate whose absorbance at 275 nm is equal to a solution of 1.10 mg/mL of tyrosine in 0.006 N HCl in one minute. SAPU activity is measured in the FCC SAPU assay, which is based on hydrolysis of Hammarstan casein substrate. One SAPU unit is defined as that amount of enzyme that will liberate one μmole of tyrosine per minute at pH 3 and 37° C. PU activity is the activity of an enzyme measure in the FCC PU assay, which is based on the hydrolysis of casein. One PU unit is defined as the amount of enzyme that liberates 1 μg of tyrosine per hour at pH 6.0 and 40° C. More information concerning the above referenced enzymes is available from the National Enzyme Company, Forsyth, Mo., through technical bulletins concerning the enzymes.

The ingredients contained in these formulations can be obtained from the following sources (Table 3).

TABLE 3

Sources.

| Ingredient/Extract | Available from |
|---|---|
| Grape Seed Extract | Indena - Milan, Italy |
| | Polyphenolics - Canandaigua, NY |
| | InterHealth - Concord, CA |
| | Tri-K Industries - Fanerson, NJ |
| *Ginkgo Biloba* Extract | Indena - Milan, Italy |
| | Weinstein Nutritional - Irvine, CA |
| | OptiPure - Los Angeles, CA |
| | Botanicals International - Long Beach, CA |
| Bilberry Extract | Indena - Milan, Italy |
| | OptiPure - Los Angeles, CA |
| | Chemco Industries - Los Angeles, CA |
| Grape Skin Extract | Freeman Industries - Tuckahoe, NY |
| | Weinstein Nutritional - Irvine, CA |
| | Brucia Extracts - California |
| Quercetin | Weinstein Nutritional - Irvine, CA |
| | Botanicals International - Long Beach, CA |
| | Triarco Industries - Wayne, NY |
| Enzyme Blend | National Enzyme Co. - Forsyth, MO |
| | MakWood - Thiensville, WI |
| | Botanicals International - Long Beach, CA |
| *Citrus* Extract | Botanicals International - Long Beach, CA |

Resveratrol (as *Polygonum cuspidatum* extract) available from Naturex, NJ, USA

Two example compositions can contain the following ingredients per capsule (Tables 4a and 4b):

TABLE 4a

Example Formula

| Ingredient | % Formulation | Amount |
|---|---|---|
| Grape Seed Extract | 20% | 25 mg |
| *Ginkgo Biloba* Extract | 8% | 10 mg |
| Bilberry Extract | 8% | 10 mg |
| Grape Skin Extract | 24% | 30 mg |
| *Citrus* Extract | 40% | 50 mg |
| Total | 100% | 125 mg |

TABLE 4b

Example Formula

| Ingredient | Amount |
|---|---|
| Grape Seed Extract | 50 mg |
| *Ginkgo Biloba* Extract | 20 mg |

TABLE 4b-continued

Example Formula

| Ingredient | Amount |
|---|---|
| Bilberry Extract | 20 mg |
| Grape Skin Extract | 60 mg |
| *Citrus* Extract | 100 mg |
| Total | 250 mg |

Another example formula contains the following ingredients per capsule (Table 5):

TABLE 5

Example formula

| Ingredient | % Formulation | Amount |
|---|---|---|
| Enzyme Blend | 4.58% | 75 mg |
| Grape Seed Extract | 3.30% | 54 mg |
| Grape Skin Extract | 67.77% | 1,110 mg |
| Quercetin | 7.32% | 120 mg |
| *Ginkgo Biloba* Extract | 9.71% | 159 mg |
| Bilberry Extract | 7.32% | 120 mg |
| Total | 100% | 1,638 mg |

The ingredients for a dietary supplement of a Supplement Formulation E can be obtained from any appropriate supplier. For example, the suppliers listed above can be used to obtain all the ingredients for a dietary supplement of a Supplement Formulation E. In some cases, the ingredients can be obtained from sources that were not subjected to a fermentation process. For example, unfermented grape seed extract and unfermented grape skin extract can be used as ingredients for a dietary supplement of a Supplement Formulation E. Such unfermented ingredients can be obtained from any supplier such as Polyphenolics (Canandaigua, N.Y.).

It is noted that the percentage for each ingredient in Supplement Formulation E can be changed, provided the resulting composition can inhibit platelet activity or LDL cholesterol oxidation. For example, the percentage of *Ginkgo biloba* extract can be increased to greater than 10%.

In another example, a dietary supplement of a Supplement Formulation E can include:

Example Formula

| | |
|---|---|
| Grape Seed & Skin Extract Blend | 330.0 mg |
| Resveratrol Blend | 60.0 mg |
| Green Tea (leaf) Extract | 100.0 mg |
| Quercetin, Bromelain, Fungal Proteases, Bilberry (berry) Extract, and *Ginkgo Biloba* (leaf) Extract Blend | 60.0 mg |

In another example, a daily dose of a dietary supplement of a Supplement Formulation E can be designed to provide the following effective amounts:

Example Formula

| | |
|---|---|
| Grape Seed & Skin Extract Blend | 330 mg |
| Resveratrol Extract | 60 mg |
| Green Tea (leaf) Extract | 100 mg |

| | |
|---|---|
| Quercetin, Bromelain Proteases, Fungal Proteases, Bilberry (berry) Extract, and *Ginkgo Biloba* (leaf) Extract. | 60 mg |

The blend of quercetin, bromelain, fungal proteases, bilberry (berry) extract, and *Ginkgo biloba* (leaf) extract can include effective amounts of each of the ingredients. The composition can use, for example, from about 20 to about 200 mg of quercetin powder or from about 40 to about 60 mg of quercetin powder. The composition can include, for example, from about 0.1 to 200 mg of bilberry (berry) extract, from about 0.1 to 100 mg of bilberry (berry) extract, or from about 0.1 to 10 mg of bilberry (berry) extract. The composition can include, for example, from about 0.1 to 30 mg of *Ginkgo biloba* (leaf) extract, from about 0.1 to 100 mg of *Ginkgo biloba* (leaf) extract, or from about 0.1 to 10 mg of *Ginkgo biloba* (leaf) extract. The composition can include, for example, from about 100 HUT to about 1000 HUT or from about 200 HUT to about 700 HUT of one or more fungal proteases such as *Aspergillus oryzae* var.

In some cases, a dietary supplement of a Supplement Formulation E can be made and used as described in International Patent Application No. PCT/US98/16181, U.S. Pat. No. 6,818,233, or U.S. Pat. No. 7,229,651, each of which is herein incorporated by reference in its entirety. For example, a dietary supplement of a Supplement Formulation E can be made to have the ingredients as set forth in International Patent Application No. PCT/US98/16181, U.S. Pat. No. 6,818,233, or U.S. Pat. No. 7,229,651.

Supplement Formulation F

A dietary supplement of a Supplement Formulation F can include, without limitation, a mineral-amino acid compound and a polysaccharide. In some embodiments, the mineral-amino acid compound and the polysaccharide of a dietary supplement of a Supplement Formulation F can be conjugated together for form a complex. In some embodiments, the conjugation includes one or more of a covalent, coordinate covalent, Van der Waals interactions, hydrophobic, hydrogen, or ionic bond.

A mineral-amino acid compound can include any mineral having a dietary benefit that is chelated with (e.g., forms a salt with) an amino acid. In some cases, the mineral-amino acid compound can be an amino acid chelated mineral. In some cases, the mineral-amino acid compound can be a mineral-amino acid salt. Any appropriate mineral having a dietary or health benefit can be used as a component of a dietary supplement of a Supplement Formulation F. For example, chromium, calcium, copper, iron, magnesium, manganese, molybdenum, potassium, zinc, selenium, or iodine can be used as a mineral for a mineral-amino acid compound.

In addition, any appropriate amino acid can used to form a chelate with a mineral to create a mineral-amino acid compound that can be included in a dietary supplement of a Supplement Formulation F. In some cases, the amino acid portion of a mineral-amino acid compound can be one or more natural or unnatural amino acids. For example, an amino acid can be a natural amino acid. As used herein, the term "natural" amino acid refers to one of the twenty commonly occurring amino acids. Natural amino acids can be in their D or L form. For example, a natural amino acid can be selected from the group consisting of L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, and mixtures thereof. In some cases, an amino acid is selected from L-glycine and L-aspartic acid.

Any appropriate polysaccharide can be conjugated with a mineral-amino acid compound to form a complex that can be included in a dietary supplement of a Supplement Formulation F. For example, cellulose derivatives, polyhexoses, polypentoses, polydextrose, starch, polygalactan, polymannan, chitin, chitosan, chondroitin, polyfructose, polyfructose (e.g., inulin), pectin, and derivatives thereof can be used. In some cases, inulin having a degree of polymerization ranging from about 2 to about 100 (e.g., about 2-10; about 12-15; about 20-30; about 25-45; about 30-40; about 50-75; about 45-65; about 50-55; about 70-80; about 75-90; and about 92-100) can be conjugated with a mineral-amino acid compound to form a complex that can be included in a dietary supplement of a Supplement Formulation F.

A complex of a mineral-amino acid compound and polysaccharide can be prepared by heating a composition including water, one or more mineral-amino acid compounds, and one or more polysaccharides at a temperature from about 100° F. to about 180° F. (e.g., 100° F.; 110° F.; 120° F.; 125° F.; 130° F.; 140° F.; 145° F.; 150° F.; 160° F.; 165° F.; 170° F.; 175° F.; and 180° F.). In some cases, the composition can be heated at from about 140° F. to about 180° F. In some cases, the composition can be heated at about 160° F. In some cases, the composition can be heated for from about 5 minutes to about 30 minutes (e.g., about 5 minutes; about 10 minutes; about 15 minutes; about 20 minutes; about 25 minutes; and about 30 minutes). In some cases, the composition can be heated for about 20 minutes. In some cases, the complex can be dried, for example, to a moisture content of less than about 15% (e.g., less than about 14%, less than about 12%, less than about 10%, less than about 8%, less than about 5%, and less than about 2%) following heating.

A complex of a mineral-amino acid compound and polysaccharide can be prepared using a ratio of mineral-amino acid compound to polysaccharide ranging from 10:1 to 1:10 (e.g., 10:1; 6:1; 5:1; 4:1; 3:1; 2:1; 1:1.5; 1:1; 1:1.5; 1:2; 1:3; 1:4; 1:5; 1:6; and 1:10). For example, a ratio of mineral-amino acid compound to polysaccharide can be 5:1 or 1:1. In some cases, a mineral-amino acid compound/polysaccharide complex can be zinc aspartate:zinc glycinate:inulin (degree of polymerization of 12-15) having a ratio of 50:30:20 by weight. In some cases, a mineral-amino acid compound/polysaccharide complex can be iron aspartate:iron glycinate:inulin (degree of polymerization of 2-10) having a ratio of 25:25:50 by weight.

Mineral-amino acid compound/polysaccharide complexes can have properties that distinguish them from a simple mixture of the same mineral-amino acid compound and polysaccharide. For example, a complex of a mineral-amino acid compound and a polysaccharide can diffuse slower across a 3500 MW cutoff dialysis membrane than an uncomplexed mixture of the same mineral-amino acid compound and polysaccharide. In some cases, a mineral-amino acid compound/polysaccharide complex included in a dietary supplement of a Supplement Formulation F can exhibit a different Fourier-Transform Near-IR (FT-NIR) spectrum compared to a similar uncomplexed mixture as determined by an industry standard correlation factor.

In some cases, a dietary supplement of a Supplement Formulation F can include two or more different mineral-amino acid compound/polysaccharide complexes. For example, a dietary supplement of a Supplement Formulation F can include two or more of a calcium-amino acid compound/polysaccharide complex, an iron-amino acid compound/polysaccharide complex, an iodine-amino acid compound/polysaccharide complex, a magnesium-amino acid compound/polysaccharide complex, a zinc-amino acid compound/polysaccharide complex, a selenium-amino acid compound/polysaccharide complex, a copper-amino acid compound/polysaccharide complex, a manganese-amino acid compound/polysaccharide complex, a molybdenum-amino acid compound/polysaccharide complex, and a boron-amino acid compound/polysaccharide complex. In some cases, the mineral-amino acid compound/polysaccharide complex can include a mineral-amino acid compound that has 75% aspartate and 25% glycinate. In some cases, the mineral-amino acid compound/polysaccharide complex can include polyfructose. In some cases, the mineral-amino acid compound/polysaccharide complex can include inulin having a degree of polymerization ranging from about 2 to about 100. In some cases, the mineral-amino acid compound/polysaccharide complex can include inulin having a degree of polymerization of about 12-15.

In some cases, a dietary supplement of a Supplement Formulation F can include one or more of vitamin A, vitamin C, vitamin D, vitamin E, vitamin K, thiamin, riboflavin, niacin, vitamin B6, folate, vitamin B12, biotin, pantothenic acid, and phosphorous.

In some cases, a dietary supplement of a Supplement Formulation F can be a composition that includes (Table 6):

TABLE 6

|  | Total Daily Dose |
| --- | --- |
| Vitamin A (as beta carotene) | 1-5000 IU |
| Vitamin C (as ascorbic acid) | 30-240 mg |
| Vitamin D (as cholecalciferol) | 1-600 IU |
| Vitamin E (as d-alpha tocopheryl succinate) | 15-60 IU |
| Vitamin K (as phytonadione) | 0-56 μg |
| Thiamin (as thiamin HCl) | 1.5-15 mg |
| Riboflavin | 1.7-17 mg |
| Niacin (as niacinamide) | 20-100 mg |
| Vitamin B6 (as pyridoxine HCl) | 2-20 mg |
| Folate (as folic acid) | 200-800 μg |
| Vitamin B12 (as cyanocobalamin) | 6-18 μg |
| Biotin (as d-biotin) | 20-400 μg |
| Pantothenic Acid (as calcium pantothenate) | 10-200 mg |
| Calcium (as calcium carbonate, dicalcium phosphate, calcium citrate, calcium gluconate, calcium amino acid polysaccharide complex) | 200-1000 mg |
| Iron (as iron amino acid polysaccharide complex) | 0-18 mg |
| Phosphorous (as dicalcium phosphate) | 0-300 mg |
| Iodine (as iodine amino acid polysaccharide complex) | 100-300 μg |
| Magnesium (as magnesium oxide, magnesium lactate, magnesium citrate, magnesium amino acid polysaccharide complex) | 100-400 mg |
| Zinc (zinc amino acid polysaccharide complex) | 5-30 mg |
| Selenium (as selenium amino acid polysaccharide complex) | 35-150 μg |
| Copper (copper amino acid polysaccharide complex) | 1-5 mg |
| Manganese (as manganese amino acid polysaccharide complex) | 1-5 mg |
| Chromium (as chromium amino acid polysaccharide complex) | 60-360 μg |
| Molybdenum (as molybdenum amino acid polysaccharide complex) | 50-150 μg |
| Boron (as boron amino acid polysaccharide complex) | 0-300 μg |

The phrase "total daily dose" as used herein refers to the amount of active ingredient administered over a 24 hour period. For example, the amount of zinc-amino acid compound/polysaccharide complex in a total daily dose is calculated based on the amount of zinc administered over 24 hours, not on the amount of zinc-amino acid compound/polysaccharide complex administered over 24 hours. A total daily dose may be prepared and administered in the form of one or more capsules or tablets (e.g., two capsules or tablets, three capsules or tablets, four capsules or tablets, five capsules or tablets, and six capsules or tablets). In some cases, one or more capsules or tablets can be administered in one or more dosages over the course of 24 hours (e.g., one dose, two doses, three doses, four doses, five doses, and six doses), wherein the one or more dosages do not exceed the total daily dose.

In some cases, a dietary supplement of a Supplement Formulation F can be a composition that includes (Table 7):

TABLE 7

|  | Total Daily Dose |
| --- | --- |
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Vitamin K (as phytonadione) | 28 μg |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 800 μg |
| Vitamin B12 (as cyanocobalamin) | 12 μg |
| Biotin (as d-biotin) | 300 μg |
| Pantothenic Acid (as calcium pantothenate) | 20 mg |
| Calcium (as calcium carbonate, dicalcium phosphate, calcium citrate, calcium gluconate, calcium amino acid polyfructose complex) | 250 mg |
| Iron (as iron amino acid polyfructose complex) | 9 mg |
| Phosphorous (as dicalcium phosphate) | 65 mg |
| Iodine (as iodine amino acid polyfructose complex) | 150 μg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 μg |
| Copper (copper amino acid polyfructose complex) | 3 mg |
| Manganese (as manganese amino acid polyfructose complex) | 2.5 mg |
| Chromium (as chromium amino acid polyfructose complex) | 120 μg |
| Molybdenum (as molybdenum amino acid polyfructose complex) | 75 μg |
| Boron (as boron amino acid polyfructose complex) | 150 μg |

In some cases, a dietary supplement of a Supplement Formulation F can be a composition that includes (Table 8):

TABLE 8

|  | Total Daily Dose |
| --- | --- |
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 600 μg |
| Vitamin B12 (as cyanocobalamin) | 12 μg |
| Biotin (as d-biotin) | 60 μg |
| Pantothenic Acid (as calcium pantothenate) | 20 mg |
| Calcium (as calcium carbonate, dicalcium phosphate, calcium citrate, calcium gluconate, calcium amino acid polyfructose complex) | 250 mg |
| Phosphorous (as dicalcium phosphate) | 65 mg |
| Iodine (as iodine amino acid polyfructose complex) | 150 μg |
| Magnesium (as magnesium oxide, magnesium lactate, magnesium citrate, magnesium amino acid polyfructose complex) | 200 mg |

TABLE 8-continued

|  | Total Daily Dose |
|---|---|
| Zinc (zinc amino acid polyfructose complex) | 15 mg |
| Selenium (as selenium amino acid polyfructose complex) | 105 μg |
| Copper (copper amino acid polyfructose complex) | 3 mg |
| Manganese (as manganese amino acid polyfructose complex) | 4 mg |
| Chromium (as chromium amino acid polyfructose complex) | 120 μg |
| Molybdenum (as molybdenum amino acid polyfructose complex) | 75 μg |
| Boron (as boron amino acid polyfructose complex) | 150 μg |

In some cases, a dietary supplement of a Supplement Formulation F can be a composition that includes (Table 9):

TABLE 9

|  | Total Daily Dose |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Thiamin (as thiamin HCl) | 8.5 mg |
| Riboflavin | 10 mg |
| Niacin (as niacinamide) | 75 mg |
| Vitamin B6 (as pyridoxine HCl) | 10 mg |
| Folate (as folic acid) | 1000 μg |
| Vitamin B12 (as cyanocobalamin) | 16 μg |
| Biotin (as d-biotin) | 300 μg |
| Pantothenic Acid (as calcium pantothenate) | 20 mg |
| Calcium (as calcium carbonate, dicalcium phosphate, calcium citrate, calcium gluconate, calcium amino acid polyfructose complex) | 300 mg |
| Iron (as iron amino acid polyfructose complex) | 9 mg |
| Phosphorous (as dicalcium phosphate) | 65 mg |
| Iodine (as iodine amino acid polyfructose complex) | 150 μg |
| Magnesium (as magnesium oxide, magnesium lactate, magnesium citrate, magnesium amino acid polyfructose complex) | 225 mg |
| Zinc (zinc amino acid polyfructose complex) | 15 mg |
| Selenium (as selenium amino acid polyfructose complex) | 105 μg |
| Copper (copper amino acid polyfructose complex) | 3 mg |
| Manganese (as manganese amino acid polyfructose complex) | 2.5 mg |
| Chromium (as chromium amino acid polyfructose complex) | 120 μg |
| Molybdenum (as molybdenum amino acid polyfructose complex) | 75 μg |
| Boron (as boron amino acid polyfructose complex) | 150 μg |

In some cases, a dietary supplement of a Supplement Formulation F can be a composition that includes (Table 10):

TABLE 10

|  | Total Daily Dose |
|---|---|
| Vitamin A (as beta carotene) | 2500 IU |
| Vitamin C (as ascorbic acid) | 80 mg |
| Vitamin D (as cholecalciferol) | 200 IU |
| Vitamin E (as d-alpha tocopheryl succinate) | 15 IU |
| Thiamin (as thiamin HCl) | 0.7 mg |
| Riboflavin | 0.8 mg |
| Niacin (as niacinamide) | 9 mg |
| Vitamin B6 (as pyridoxine HCl) | 1.05 mg |
| Folate (as folic acid) | 200 μg |
| Vitamin B12 (as cyanocobalamin) | 3 μg |
| Biotin (as d-biotin) | 30 μg |
| Pantothenic Acid (as calcium pantothenate) | 5 mg |
| Calcium (as calcium carbonate, dicalcium phosphate, calcium citrate, calcium gluconate, calcium amino acid polyfructose complex) | 160 mg |
| Iron (as iron amino acid polyfructose complex) | 5 mg |
| Phosphorous (as dicalcium phosphate) | 20 mg |
| Iodine (as iodine amino acid polyfructose complex) | 70 μg |
| Magnesium (as magnesium oxide, magnesium lactate, magnesium citrate, magnesium amino acid polyfructose complex) | 40 mg |
| Zinc (zinc amino acid polyfructose complex) | 4 mg |
| Copper (copper amino acid polyfructose complex) | 0.5 mg |
| Manganese (as manganese amino acid polyfructose complex) | 0.5 mg |
| Chromium (as chromium amino acid polyfructose complex) | 10 μg |
| Molybdenum (as molybdenum amino acid polyfructose complex) | 10 μg |

In some cases, a dietary supplement of a Supplement Formulation F can be a composition that includes (Table 11):

TABLE 11

|  | Total Daily Dose |
|---|---|
| Vitamin A (as beta carotene) | 5000 IU |
| Vitamin C (as ascorbic acid) | 160 mg |
| Vitamin D (as cholecalciferol) | 400 IU |
| Vitamin E (as d-alpha tocopheryl succinate) | 30 IU |
| Thiamin (as thiamin HCl) | 1.4 mg |
| Riboflavin | 1.6 mg |
| Niacin (as niacinamide) | 18 mg |
| Vitamin B6 (as pyridoxine HCl) | 2.1 mg |
| Folate (as folic acid) | 400 μg |
| Vitamin B12 (as cyanocobalamin) | 6 μg |
| Biotin (as d-biotin) | 60 μg |
| Pantothenic Acid (as calcium pantothenate) | 10 mg |
| Calcium (as calcium carbonate, dicalcium phosphate, calcium citrate, calcium gluconate, calcium amino acid polyfructose complex) | 320 mg |
| Iron (as iron amino acid polyfructose complex) | 10 mg |
| Phosphorous (as dicalcium phosphate) | 40 mg |
| Iodine (as iodine amino acid polyfructose complex) | 140 μg |
| Magnesium (as magnesium oxide, magnesium lactate, magnesium citrate, magnesium amino acid polyfructose complex) | 80 mg |
| Zinc (zinc amino acid polyfructose complex) | 8 mg |
| Copper (copper amino acid polyfructose complex) | 1 mg |
| Manganese (as manganese amino acid polyfructose complex) | 1 mg |
| Chromium (as chromium amino acid polyfructose complex) | 20 μg |
| Molybdenum (as molybdenum amino acid polyfructose complex) | 20 μg |

In some cases, a dietary supplement of a Supplement Formulation F can be a composition that includes (Table 12):

TABLE 12

|  | Total Daily Dose |
|---|---|
| Vitamin A (as beta carotene) | 3500 IU |
| Vitamin C (as ascorbic acid) | 150 mg |
| Vitamin D (as cholecalciferol) | 200 IU |
| Vitamin E (as d-alpha tocopheryl succinate) | 45 IU |
| Thiamin (as thiamin HCl) | 7.5 mg |
| Riboflavin | 8.5 mg |
| Niacin (as niacinamide) | 75 mg |
| Vitamin B6 (as pyridoxine HCl) | 10 mg |
| Folate (as folic acid) | 600 μg |
| Vitamin B12 (as cyanocobalamin) | 12 μg |
| Biotin (as d-biotin) | 60 μg |
| Pantothenic Acid (as calcium pantothenate) | 15 mg |
| Calcium (as calcium carbonate, dicalcium phosphate, calcium citrate, calcium gluconate, calcium amino acid polyfructose complex) | 250 mg |

TABLE 12-continued

| | Total Daily Dose |
|---|---|
| Phosphorous (as dicalcium phosphate) | 65 mg |
| Iodine (as iodine amino acid polyfructose complex) | 150 μg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 μg |
| Copper (copper amino acid polyfructose complex) | 3 mg |
| Manganese (as manganese amino acid polyfructose complex) | 3 mg |
| Chromium (as chromium amino acid polyfructose complex) | 180 μg |
| Molybdenum (as molybdenum amino acid polyfructose complex) | 90 μg |
| Boron (as boron amino acid polyfructose complex) | 150 μg |

In some cases, a dietary supplement of a Supplement Formulation F can be a composition that includes (Table 13):

TABLE 13

| | Total Daily Dose |
|---|---|
| Vitamin D (as cholecalciferol) | 300 IU |
| Calcium (as calcium carbonate, dicalcium phosphate, calcium citrate, calcium gluconate, calcium amino acid polyfructose complex) | 750 mg |
| Phosphorous (as dicalcium phosphate) | 100 mg |
| Magnesium (as magnesium oxide, magnesium lactate, magnesium citrate, magnesium amino acid polyfructose complex) | 150 mg |

In some cases, a dietary supplement of a Supplement Formulation F can be a composition that includes (Table 14):

TABLE 14

| | Total Daily Dose |
|---|---|
| Vitamin D (as cholecalciferol) | 400 IU |
| Calcium (as calcium carbonate, dicalcium phosphate, calcium citrate, calcium gluconate, calcium amino acid polyfructose complex) | 1000 mg |
| Phosphorous (as dicalcium phosphate) | 130 mg |
| Magnesium (as magnesium oxide, magnesium lactate, magnesium citrate, magnesium amino acid polyfructose complex) | 200 mg |

In some cases, a dietary supplement of a Supplement Formulation F can be a composition that includes (Table 15):

TABLE 15

| | Total Daily Dose |
|---|---|
| Vitamin D (as cholecalciferol) | 200 IU |
| Calcium (as calcium carbonate, dicalcium phosphate, calcium citrate, calcium gluconate, calcium amino acid polyfructose complex) | 500 mg |
| Phosphorous (as dicalcium phosphate) | 64 mg |
| Magnesium (as magnesium oxide, magnesium lactate, magnesium citrate, magnesium amino acid polyfructose complex) | 100 mg |

In some cases, a dietary supplement of a Supplement Formulation F can be a composition that includes (Table 16):

TABLE 16

| | Total Daily Dose |
|---|---|
| Vitamin D (as cholecalciferol) | 500 IU |
| Calcium (as calcium carbonate, dicalcium phosphate, calcium citrate, calcium gluconate, calcium amino acid polyfructose complex) | 1250 mg |
| Phosphorous (as dicalcium phosphate) | 160 mg |
| Magnesium (as magnesium oxide, magnesium lactate, magnesium citrate, magnesium amino acid polyfructose complex) | 250 mg |

A mineral-amino acid compound/polysaccharide complex of a dietary supplement of a Supplement Formulation F can reduce the formation of free radicals in the intestinal tract as compared to an uncomplexed mineral (e.g., a mineral sulfate, chloride, citrate, or gluconate). In some cases, the mineral-amino acid compound/polysaccharide complex can be an iron-amino acid compound/polyfructose complex or a copper-amino acid compound/polyfructose complex. In some cases, the mineral-amino acid compound/polysaccharide complex can be a glycinate or aspartic acid-iron or copper species complexed with inulin.

In one example, a dietary supplement of a Supplement Formulation F can include:

| | |
|---|---|
| Vitamin A (as beta carotene) | 3500 IU |
| Vitamin C (as ascorbic acid) | 150 mg |
| Vitamin D (as cholecalciferol) | 200 IU |
| Vitamin E (as d-alpha tocopheryl succinate) | 45 IU |
| Thiamin (as thiamin HCl) | 7.5 mg |
| Riboflavin | 8.5 mg |
| Niacin (as niacinamide) | 75 mg |
| Vitamin B6 (as pyridoxine HCl) | 10 mg |
| Folate (as folic acid) | 600 μg |
| Vitamin B12 (as cyanocobalamin) | 12 μg |
| Biotin (as d-biotin) | 60 μg |
| Pantothenic Acid (as calcium pantothenate) | 15 mg |
| Calcium (as calcium carbonate, dicalcium phosphate, calcium citrate, calcium gluconate, calcium amino acid polyfructose complex) | 250 mg |
| Iodine (as iodine amino acid polyfructose complex) | 150 μg |
| Magnesium (as magnesium oxide, magnesium lactate, magnesium citrate, magnesium amino acid polyfructose complex) | 200 mg |
| Zinc (zinc amino acid polyfructose complex) | 15 mg |
| Selenium (as selenium amino acid polyfructose complex) | 105 μg |
| Copper (copper amino acid polyfructose complex) | 3 mg |
| Manganese (as manganese amino acid polyfructose complex) | 3 mg |
| Chromium (as chromium amino acid polyfructose complex) | 180 μg |
| Molybdenum (as molybdenum amino acid polyfructose complex) | 90 μg |
| Boron (as boron amino acid polyfructose complex) | 150 μg |

In another example, a daily dose of a dietary supplement of a Supplement Formulation F can be designed to provide the following effective amounts:

| | |
|---|---|
| Vitamin A (as beta carotene) | 3500 IU |
| Vitamin C (as ascorbic acid) | 150 mg |
| Vitamin D (as cholecalciferol) | 200 IU |
| Vitamin E (as d-alpha tocopheryl succinate) | 45 IU |
| Thiamin (as thiamin HCl) | 7.5 mg |
| Riboflavin | 8.5 mg |
| Niacin (as niacinamide) | 75 mg |
| Vitamin B6 (as pyridoxine HCl) | 10 mg |
| Folate (as folic acid) | 600 μg |
| Vitamin B12 (as cyanocobalamin) | 12 μg |
| Biotin (as d-biotin) | 60 μg |
| Pantothenic Acid (as calcium pantothenate) | 15 mg |
| Calcium (as calcium carbonate, dicalcium phosphate, calcium citrate, calcium gluconate, calcium amino acid oligofructose complex) | 250 mg |

| | |
|---|---|
| Iodine (as iodine amino acid oligofructose complex) | 150 µg |
| Magnesium (as magnesium oxide, magnesium lactate, magnesium citrate, magnesium amino acid oligofructose complex) | 200 mg |
| Zinc (as zinc amino acid oligofructose complex) | 15 mg |
| Selenium (as selenium amino acid oligofuctose complex) | 105 µg |
| Copper (as copper amino acid oligofructose complex) | 3 mg |
| Manganese (as manganese amino acid oligofructose complex) | 3 mg |
| Chromium (as chromium amino acid oligofructose complex) | 180 µg |
| Molybdenum (as molybdenum amino acid oligofructose complex) | 90 µg |
| Boron (as boron amino acid oligofructose complex) | 150 µg |

In another example, a daily dose of a dietary supplement of a Supplement Formulation F can be designed to provide the following effective amounts:

| | |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 600 µg |
| Vitamin B12 (as cyanocobalamin) | 12 µg |
| Biotin (as d-biotin) | 60 µg |
| Pantothenic Acid (as calcium pantothenate | 20 mg |
| Calcium (as calcium carbonate, dicalcium phosphate, calcium citrate, calcium gluconate, calcium amino acid oligofructose complex) | 250 mg |
| Iodine (as iodine amino acid oligofructose complex) | 150 µg |
| Magnesium (as magnesium oxide, magnesium lactate, magnesium citrate, magnesium amino acid oligofructose complex) | 200 mg |
| Zinc (as zinc amino acid oligofructose complex) | 15 mg |
| Selenium (as selenium amino acid oligofuctose complex) | 105 µg |
| Copper (as copper amino acid oligofructose complex) | 3 mg |
| Manganese (as manganese amino acid oligofructose complex) | 4 mg |
| Chromium (as chromium amino acid oligofructose complex) | 120 µg |
| Molybdenum (as molybdenum amino acid oligofructose complex) | 75 µg |
| Boron (as boron amino acid oligofructose complex) | 150 µg |

In another example, a daily dose of a dietary supplement of a Supplement Formulation F can be designed to provide the following effective amounts:

| | |
|---|---|
| Vitamin A (as beta carotene) | 3000 IU |
| Vitamin C (as ascorbic acid) | 150 mg |
| Vitamin D (as cholecalciferol) | 200 IU |
| Vitamin E (as d-alpha tocopheryl succinate) | 30 IU |
| Vitamin K (as phytonadione) | 28 µg |
| Thiamin (as thiamin HCl) | 15 mg |
| Riboflavin | 17 mg |
| Niacin (as niacinamide) | 75 mg |
| Vitamin B6 (as pyridoxine HCl) | 10 mg |
| Folate (as folic acid) | 800 µg |
| Vitamin B12 (as cyanocobalamin) | 12 µg |
| Biotin (as d-biotin) | 300 µg |
| Pantothenic Acid (as calcium pantothenate | 20 mg |
| Calcium (as calcium carbonate, dicalcium phosphate, calcium citrate, calcium gluconate, calcium amino acid oligofructose complex) | 250 mg |
| Iodine (as iodine amino acid oligofructose complex) | 150 µg |
| Magnesium (as magnesium oxide, magnesium lactate, magnesium citrate, magnesium amino acid oligofructose complex) | 200 mg |
| Zinc (as zinc amino acid oligofructose complex) | 15 mg |
| Selenium (as selenium amino acid oligofuctose complex) | 105 µg |
| Copper (as copper amino acid oligofructose complex) | 3 mg |
| Manganese (as manganese amino acid oligofructose complex) | 4 mg |
| Chromium (as chromium amino acid oligofructose complex) | 120 µg |
| Molybdenum (as molybdenum amino acid oligofructose complex) | 75 µg |
| Boron (as boron amino acid oligofructose complex) | 150 µg |
| Iron (as iron amino acid oligofructose complex) | 9 mg |

In some cases, a dietary supplement of a Supplement Formulation F can be made and used as described in International Patent Application No. PCT/US2009/050111, U.S. Pat. No. 8,273,393, or U.S. Pat. No. 8,697,158, each of which is herein incorporated by reference in its entirety. For example, a dietary supplement of a Supplement Formulation F can be made to have the ingredients as set forth in International Patent Application No. PCT/US2009/050111, U.S. Pat. No. 8,273,393, or U.S. Pat. No. 8,697,158.

Supplement Formulation G

Supplement Formulation G can provide ingredients useful for a mammal's health. In general, a dietary supplement of a Supplement Formulation G can include one or more of an acetylcholinesterase inhibitor (e.g., huperzine A), a Bacopa monnieri extract, acetyl-L-carnitine or acetyl CoA, and a curcuminoid (e.g., curcumin). For example, a dietary supplement of a Supplement Formulation G can include an acetylcholinesterase inhibitor (e.g., huperzine A), a Bacopa monnieri extract, acetyl-L-carnitine or acetyl CoA, and a curcuminoid (e.g., curcumin). A dietary supplement of a Supplement Formulation G can be in the form of a liquid, solution, suspension, tablet, powder, cream, mist, atomized vapor, aerosol, soft gelatin capsule, hard gelatin capsule, a gel, a confectionary, a shake, a bar, and a supplemented food.

Examples of acetylcholinesterase inhibitors that can be included within a dietary supplement of a Supplement Formulation G include, without limitation, huperzine A, carbamates (e.g., physostigmine, neostigmine, pyridostigmine, ambenonium, demarcarium, and rivastigmine), caffeine, piperidines (e.g., donepezil), xanthostigmine, aminobenzoic acid, flavonoids, pyrrolo-isoxazole, edrophonium, ladostigil, ungeremine, lactucopicrin, coumarin, donepezil, galantamine, rivastigmine, and tacrine.

Acetylcholinesterase inhibitors can be obtained as described elsewhere (e.g., Chinese Patent No. CN103951618, dated Jul. 30, 2014). In some cases, an acetylcholinesterase inhibitor such as huperzine A can be obtained commercially. For example, huperzine A can be obtained from Novel Ingredients Services (Los Angeles, Calif.; Catalog No. 018302.1).

In some cases, a dietary supplement of a Supplement Formulation G can contain one or more than one acetylcholinesterase inhibitor. A dietary supplement of a Supplement Formulation G can contain any appropriate amount of an acetylcholinesterase inhibitor. In some cases, a dietary supplement of a Supplement Formulation G can contain between about 0.01 mg and about 8 mg (e.g., between about 0.02 mg and about 0.4 mg, between about 0.03 mg and about 0.4 mg, between about 0.05 mg and about 0.4 mg, between about 0.1 mg and about 0.4 mg, between about 0.02 mg and about 0.3 mg, or between about 0.03 mg and about 0.1 mg) of an acetylcholinesterase inhibitor. In some cases, a dietary supplement of a Supplement Formulation G can be formulated to contain an amount of an acetylcholinesterase inhibitor such that a daily dose of between 0.02 mg and 0.4 mg (e.g., between 0.03 mg and 0.4 mg, between 0.05 mg and 0.4 mg, between 0.1 mg and 0.4 mg, between 0.02 mg and 0.3 mg, or between 0.03 mg and 0.1 mg) of the acetylcholinesterase inhibitor can be conveniently administered.

As described herein, a dietary supplement of a Supplement Formulation G can contain a *Bacopa monnieri* extract. A *Bacopa monnieri* extract can be obtained as described elsewhere (e.g., PCT International Patent Application No. WO2006097043, dated Sep. 21, 2006). In some cases, a *Bacopa monnieri* extract can be obtained commercially. For example, a *Bacopa monnieri* extract can be obtained from Vidya Herbs (Banglore, India).

In some cases, a dietary supplement of a Supplement Formulation G can contain one or more than one *Bacopa monnieri* extract. A dietary supplement of a Supplement Formulation G can contain any appropriate amount of a *Bacopa monnieri* extract. For example, at least 10 percent (e.g., at least 15, 20, 25, 30, 35, 40, 50, 60, 70, 80, or 90 percent) of a dietary supplement of a Supplement Formulation G can be a *Bacopa monnieri* extract. In some cases, a dietary supplement of a Supplement Formulation G can contain between about 25 mg and about 500 mg (e.g., between about 100 mg and about 500 mg, between about 150 mg and about 500 mg, between about 200 mg and about 500 mg, between about 100 mg and about 450 mg, between about 100 mg and about 400 mg, between about 200 mg and about 400 mg, or between about 250 mg and about 350 mg) of a *Bacopa monnieri* extract. In some cases, a dietary supplement of a Supplement Formulation G can be formulated to contain an amount of a *Bacopa monnieri* extract such that a daily dose of between about 25 mg and about 500 mg (e.g., between about 100 mg and about 500 mg, between about 150 mg and about 500 mg, between about 200 mg and about 500 mg, between about 100 mg and about 450 mg, between about 100 mg and about 400 mg, between about 200 mg and about 400 mg, or between about 250 mg and about 350 mg) of the *Bacopa monnieri* extract can be conveniently administered.

As described herein, a dietary supplement of a Supplement Formulation G can contain acetyl-L-carnitine or acetyl CoA. In some cases, a dietary supplement of a Supplement Formulation G can contain both acetyl-L-carnitine and acetyl CoA.

Acetyl-L-carnitine and acetyl CoA can be obtained as described elsewhere (e.g., Chinese Patent Application No. CN103664667, dated Mar. 26, 2014). In some cases, acetyl-L-carnitine and acetyl CoA can be obtained commercially. For example, acetyl-L-carnitine and acetyl CoA can be obtained from Huanggang Huayang Pharmaceutical Co. Ltd. (China).

A dietary supplement of a Supplement Formulation G can contain any appropriate amount of acetyl-L-carnitine and/or acetyl CoA. For example, at least 10 percent (e.g., at least 15, 20, 25, 30, 35, 40, 50, 60, 70, 80, or 90 percent) of a dietary supplement of a Supplement Formulation G can be acetyl-L-carnitine and/or acetyl CoA. In some cases, a dietary supplement of a Supplement Formulation G can contain between about 100 mg and about 3000 mg (e.g., between about 200 mg and about 3000 mg, between about 300 mg and about 3000 mg, between about 400 mg and about 3000 mg, between about 200 mg and about 2000 mg, between about 200 mg and about 1000 mg, between about 500 mg and about 700 mg, or between about 550 mg and about 650 mg) of acetyl-L-carnitine and/or acetyl CoA. In some cases, a dietary supplement of a Supplement Formulation G can be formulated to contain an amount of acetyl-L-carnitine and/or acetyl CoA such that a daily dose of between 200 mg and 3000 mg (e.g., between 300 mg and 3000 mg, between 400 mg and 3000 mg, between 200 mg and 2000 mg, between 200 mg and 1000 mg, between 500 mg and 700 mg, or between 550 mg and 650 mg) of the acetyl-L-carnitine and/or acetyl CoA can be conveniently administered.

As described herein, a dietary supplement of a Supplement Formulation G can contain a curcuminoid. An example of a curcuminoid that can be included within a dietary supplement of a Supplement Formulation G includes, without limitation, curcumin. Curcuminoids can be synthesized or derivatized from natural sources. In some cases, a curcuminoid can be a component of a plant extract. For example, a curcuminoid can be a component of an extract of turmeric. An extract of turmeric can be made using an ethanol or hydroalcoholic extraction. In some cases, curcuminoid and plant extracts containing curcuminoid (e.g., turmeric) can be obtained commercially. For example, turmeric extract or curcumin can be obtained from BattleChem Inc. (CA, USA).

In some cases, a dietary supplement of a Supplement Formulation G can contain one or more than one curcuminoid. A dietary supplement of a Supplement Formulation G can contain any appropriate amount of a curcuminoid. For example, at least 3 percent (e.g., at least 5, 10, 15, 20, 25, 30, 35, 40, 50, 60, 70, 80, or 90 percent) of a dietary supplement of a Supplement Formulation G can be a curcuminoid. In some cases, a dietary supplement of a Supplement Formulation G can contain between 10 mg and 500 mg (e.g., between 25 mg and 500 mg, between 50 mg and 500 mg, between 100 mg and 500 mg, between 10 mg and 400 mg, between 10 mg and 300 mg, between 10 mg and 200 mg, between 10 mg and 150 mg, between 50 mg and 150 mg, between 60 mg and 140 mg, and between 75 mg and 125 mg) of a curcuminoid. In some cases, a dietary supplement of a Supplement Formulation G can be formulated to contain an amount of a curcuminoid such that a daily dose of between 10 mg and 500 mg (e.g., between 25 mg and 500 mg, between 50 mg and 500 mg, between 100 mg and 500 mg, between 10 mg and 400 mg, between 10 mg and 300 mg, between 10 mg and 200 mg, between 10 mg and 150 mg, between 50 mg and 150 mg, between 60 mg and 140 mg, and between 75 mg and 125 mg) of the curcuminoid.

In some cases, the curcuminoid can be a component of a plant extract. For example, the curcuminoid of a dietary supplement of a Supplement Formulation G can be a component of a turmeric extract. In some cases, the turmeric extract is obtained using standard extraction techniques. In some cases, a dietary supplement of a Supplement Formulation G can contain any appropriate amount of a plant extract, such as a standard turmeric extract. For example, at least 5 percent (e.g., at least 10, 15, 20, 25, 30, 35, 40, 50, 60, 70, 80, or 90 percent) of a dietary supplement of a Supplement Formulation G can be the plant extract. Typically, a dietary supplement of a Supplement Formulation G contains between 10 mg and 500 mg (e.g., between 25 mg and 500 mg, between 50 mg and 500 mg, between 100 mg and 500 mg, between 10 mg and 400 mg, between 10 mg and 300 mg, between 10 mg and 200 mg, between 10 mg and 150 mg, between 50 mg and 150 mg, between 60 mg and 140 mg, and between 75 mg and 125 mg) of the plant extract. In some cases, a dietary supplement of a Supplement Formulation G can be formulated to contain an amount of the plant extract such that a daily dose of between 10 mg and 500 mg (e.g., between 25 mg and 500 mg, between 50 mg and 500 mg, between 100 mg and 500 mg, between 10 mg and 400 mg, between 10 mg and 300 mg, between 10 mg and 200 mg, between 10 mg and 150 mg, between 50 mg and 150 mg, between 60 mg and 140 mg, and between 75 mg and 125 mg) of the plant extract can be conveniently administered.

In some cases, a dietary supplement of a Supplement Formulation G can include one or more of the following ingredients in place of or in addition to a curcuminoid: carotenoids (e.g., alpha-carotene, beta-carotene, lycopene, lutein, zeaxanthin, and cryptoxanthin), phenolic compounds (e.g., flavonoids, flavonols, flavanones, catechins, anthocyanins, isoflavones, dihydroflavonols, and chalcones), phenolic acids (e.g., ellagic acid, tannic acid, and vanillin), hydroxycinnamic acid derivatives (e.g., caffeic, chlorogenic, ferulic acids, curcumin, and coumarins), lignans, allyl sulphides from onion or garlic, and essential oils (e.g., melaleuca oil, clove oil, cinnamon bark oil, thyme oil, oregano oil, mountain savory oil, cistus oil, eucalyptus globulus oil, orange oil, lemongrass oil, helichrysum oil, ravensara oil, lemon oil, spearmint oil, and lavender oil).

In some cases, a dietary supplement of a Supplement Formulation G can include one or more of Vitamin E, tocopherol, tocotrienol, Vitamin A, carotene, lutein, astaxanthin, CoQ10, Vitamin C, folate, uric acid, Vitamin B12, and folic acid. For example, a dietary supplement of a Supplement Formulation G can include between 10 IU (or mg) and 800 IU (or mg) (e.g., between 100 IU (or mg) and 300 IU (or mg) or between 150 IU (or mg) and 250 IU (or mg)) of any one or more of Vitamin E, tocopherol, tocotrienol, Vitamin A, carotene, lutein, astaxanthin, CoQ10, Vitamin C, folate, and uric acid. In some cases, a dietary supplement of a Supplement Formulation G can include between 0.006 mg and 2.5 mg (e.g., between 0.01 mg and 2.5 mg, between 0.1 mg and 2.5 mg, between 0.5 mg and 2.5 mg, between 0.006 mg and 1.5 mg, between 0.006 mg and 1.0 mg, or between 0.5 mg and 1.5 mg) of Vitamin B12. In some cases, a dietary supplement of a Supplement Formulation G can include between 0.4 mg and 1.0 mg (e.g., between 0.5 mg and 1.0 mg, between 0.6 mg and 1.0 mg, between 0.7 mg and 1.0 mg, between 0.4 mg and 0.9 mg, between 0.6 mg and 0.9 mg, or between 0.7 mg and 0.9 mg) of folic acid.

A dietary supplement of a Supplement Formulation G can be formulated for oral administration and can include suitable excipients, flavorings, colorants, and other ingredients. For oral administration, tablets or capsules can be prepared with pharmaceutically acceptable excipients such as binding agents, fillers, lubricants, disintegrants, or wetting agents. In some cases, tablets can include a coating (e.g., a polymer or polysaccharide-based coating with or without plasticizers and/or pigments). Liquid preparations for oral administration can take the form of, for example, solutions, syrups, or suspension, or they can be presented as a dry product for constitution with saline or other suitable liquid vehicle before use. In some cases, liquid preparations can contain pharmaceutically acceptable additives such as suspending agents, emulsifying agents, non-aqueous vehicles, preservatives, buffer salts, flavoring agents, coloring agents, and sweetening agents as appropriate. Preparations for oral administration can be suitably formulated to give controlled release of one or more compounds. In some cases, tablets or capsules can be coated with a methacrylic acid copolymer (e.g., Eudragit L100-55 or Eudragit S 100) for release beyond the stomach (e.g., in the intestine, colon, or both).

In some cases, a dietary supplement of a Supplement Formulation G can contain a pharmaceutically acceptable carrier for administration to a mammal, including, without limitation, sterile aqueous, or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Pharmaceutically acceptable carriers also can include physiologically acceptable aqueous vehicles (e.g., physiological saline) or other carriers appropriate for oral administration.

In some cases, a dietary supplement of a Supplement Formulation G can be in the form of a capsule or tablet configured to have a unit dosage equal to the daily desired dosage for a particular mammal. For example, if a mammal desires 100 mg of a particular agent, each tablet can include about 100 mg in weight of that agent. As used herein, mammals generally refer to humans, but also can include domesticated mammals (e.g., dogs, cats, and livestock such as cows, horses, pigs, or sheep). The dosages of a particular dietary supplement of a Supplement Formulation G will depend on many factors including the general health of a mammal. In some cases, a total daily dose may be prepared and administered in the form of one or more dosage forms (e.g., two tablets or capsules, three tablets or capsules, four tablets or capsules, five tablets or capsules, or six tablets or capsules).

In some cases, a dietary supplement of a Supplement Formulation G can be made and used as described in U.S. Provisional Patent Application No. 62/099,407, which is herein incorporated by reference in its entirety. For example, a dietary supplement of a Supplement Formulation G can be made to have the ingredients as set forth in U.S. Provisional Patent Application No. 62/099,407.

Supplement Formulation H

Supplement Formulation H can provide ingredients useful for a mammal's health. In general, a dietary supplement of a Supplement Formulation H can include, without limitation, one or more of a phosphatidylserine, at least one omega-3 fatty acid (e.g., docosahexaenoic acid (DHA) and/or eicosapentaenoic acid (EPA)), antioxidants, and *Ginkgo biloba*.

Any appropriate form of phosphatidylserine can be included in a dietary supplement of a Supplement Formulation H. Phosphatidylserine is a phospholipid nutrient found in fish, green leafy vegetables, soybeans, and rice. Phosphatidylserine can be obtained using any appropriate process. In some cases, phosphatidylserine can be obtained commercially. For example, phosphatidylserine can be obtained from Chemi Nutra (Minnesota, USA).

A dietary supplement of a Supplement Formulation H can contain any appropriate amount of phosphatidylserine. For example, a dietary supplement of a Supplement Formulation H can contain from 0.01 µg to about 1 g (e.g., from about 0.01 µg to about 750 mg; from about 0.01 µg to about 500 mg; from about 0.1 µg to about 1 g; from about 1 µg to about 1 g; from about 10 µg to about 1 g; or from about 100 µg to about 500 mg) of phosphatidylserine. In some cases, a dietary supplement of a Supplement Formulation H can contain about 10, 20, 30, 40, 50, 60, 70, 80, 90, 100, 110, 120, 130, 140, 150, 160, 170, 180, 190, 200, 210, 220, 230, 240, 250, 300, 400, 500, 600, 700, 800, 900, 1000 mg or more of phosphatidylserine, about any amount of phosphatidylserine between these enumerated amounts, or any range of phosphatidylserine amounts encompassing one or more of these enumerated amounts (e.g., from about one of the enumerated amounts of phosphatidylserine to about another of the enumerated amounts of phosphatidylserine). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary supplement of a Supplement Formulation H can be phosphatidylserine. In some cases, a dietary supplement of a Supplement Formulation H can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of phosphatidylserine, about any percentage of phosphatidylserine between these enumerated percentages, or any range of phosphatidylserine percentages encompassing one or more of these enumerated percentages (e.g., from about one of the enumerated percentages of phosphatidylserine to about another of the enumerated percentages of phosphatidylserine).

In some cases, phosphatidylserine can be provided in a dietary supplement of a Supplement Formulation H as substantially pure phosphatidylserine. As used herein, the term "substantially pure" refers to a compound having a purity greater than about 90% based on the weight of the compound, e.g., greater than about 90, 91, 92, 93, 94, 95, 96, 97, 98, and 99% pure by weight, including a compound that is about 100% pure by weight. In some cases, phosphatidylserine can be provided in a dietary supplement of a Supplement Formulation H as part of a complex (e.g., a complex that contains phosphatidylserine in addition to one or more other components). Phosphatidylserine can be in any form, for example, a solution, a powder, or a soluble powder.

In some cases, a dietary supplement of a Supplement Formulation H can include at least one omega-3 fatty acid source. One non-limiting omega-3 fatty acid source is docosahexaenoic acid (DHA). For example, a dietary supplement of a Supplement Formulation H can include DHA. DHA is an omega-3 fatty acid found commonly in cold-water fish. DHA is a carboxylic acid with a 22-carbon chain. DHA can be in any form, for example, a solution, a powder, or a soluble powder.

In some cases, a dietary supplement of a Supplement Formulation H can contain any appropriate type or derivative of DHA. Any appropriate method can be used to obtain DHA. For example, extraction can be used to obtain a preparation of DHA. In some cases, DHA can be extracted from naturally-occurring sources. In some cases, a liquid-liquid extraction process can be performed using fish oil as a source material to obtain a preparation of DHA. A dietary supplement of a Supplement Formulation H can contain any appropriate amount of DHA. For example, a dietary supplement of a Supplement Formulation H can contain from 0.01 μg to about 2 g (e.g., from about 0.01 μg to about 2 g; from about 0.01 μg to about 1 g; from about 0.1 μg to about 750 mg; from about 1 μg to about 500 mg; from about 10 μg to about 1 g; or from about 100 μg to about 750 mg) of DHA. In some cases, a dietary supplement of a Supplement Formulation H can contain about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 mg or more of DHA, about any amount of DHA between these enumerated amounts, or any range of DHA amounts encompassing one or more of these enumerated amounts (e.g., from about one of the enumerated amounts of DHA to about another of the enumerated amounts of DHA). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary supplement of a Supplement Formulation H can be DHA. In some cases, a dietary supplement of a Supplement Formulation H can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of DHA, about any percentage of DHA between these enumerated percentages, or any range of DHA percentages encompassing one or more of these enumerated percentages (e.g., from about one of the enumerated percentages of DHA to about another of the enumerated percentages of DHA).

Another non-limiting omega-3 fatty acid source is eicosapentaenoic acid (EPA). EPA is an omega-3 fatty acid found commonly in cold-water fish. EPA is a carboxylic acid with a 22-carbon chain (all-cis-5,8,11,14,17-eicosapentaenoic acid). EPA can be in any form, for example, a solution, a powder, or a soluble powder.

A dietary supplement of a Supplement Formulation H can contain any appropriate type or derivative of EPA. Any appropriate method can be used to obtain EPA. For example, extraction can be used to obtain a preparation of EPA. In some cases, EPA can be extracted from naturally-occurring sources. In some cases, a liquid-liquid extraction process can be performed using fish oil as a source material to obtain a preparation of EPA. A dietary supplement of a Supplement Formulation H can contain any appropriate amount of EPA. For example, a dietary supplement of a Supplement Formulation H can contain from 0.01 μg to about 2 g (e.g., from about 0.01 μg to about 2 g; from about 0.01 μg to about 1 g; from about 0.1 μg to about 750 mg; from about 1 μg to about 500 mg; from about 10 μg to about 1 g; or from about 100 μg to about 750 mg) of EPA. In some cases, a dietary supplement of a Supplement Formulation H can contain about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 mg or more of EPA, about any amount of EPA between these enumerated amounts, or any range of EPA amounts encompassing one or more of these enumerated amounts (e.g., from about one of the enumerated amounts of EPA to about another of the enumerated amounts of EPA). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary supplement of a Supplement Formulation H can be EPA. In some cases, a dietary supplement of a Supplement Formulation H can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of EPA, about any percentage of EPA between these enumerated percentages, or any range of EPA percentages encompassing one or more of these enumerated percentages (e.g., from about one of the enumerated percentages of EPA to about another of the enumerated percentages of EPA).

In some cases, a dietary supplement of a Supplement Formulation H can include DHA, EPA, or both, wherein the DHA, EPA, or both are provided as components of another ingredient. For example, a dietary supplement of a Supplement Formulation H can contain an oil, which oil contains DHA, EPA, or both. In some cases, such oil can be fish oil, e.g., derived from cold-water fish. In some cases, a dietary supplement of a Supplement Formulation H can contain about 100, 110, 120, 130, 140, 150, 160, 170, 180, 190, 200, 210, 220, 230, 240, 250, 260, 270, 280, 290, 300, 31, 320, 330, 340, 350, 360, 370, 380, 390, 400, 410, 420, 430, 440, 450, 460, 470, 480, 490, 500 mg or more of fish oil, about any amount of fish oil between these enumerated amounts, or any range of fish oil amounts encompassing one or more of these enumerated amounts (e.g., from about one of the enumerated amounts of fish oil to about another of the enumerated amounts of fish oil).

In some cases, a dietary supplement of a Supplement Formulation H can include at least one antioxidant source. An antioxidant can be any appropriate molecule capable of slowing or preventing the oxidation of another molecule. Any appropriate type of antioxidant can be included in a dietary supplement of a Supplement Formulation H. Examples of antioxidants include, without limitation, flavonoid, flavongycoside, anthocyanin, tocopherol, D-alpha-tocopherol or other Vitamin E, tocoptrienol, and carotenoid antioxidants. Antioxidants can be in any appropriate form, for example, a solution, a powder, or a soluble powder. In some cases, a dietary supplement of a Supplement Formulation H can contain an antioxidant in an amount that provides a particular potency when ingested. As one non-limiting example, International Units or "IUs" are used as a standard measure of potency. In some cases, a dietary supplement of a Supplement Formulation H can contain an antioxidant in an amount that provides about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more IUs, an antioxidant in about any appropriate amount that provides an IU between these enumerated IUs, or any range of amounts of antioxidants that provides an IU encompassing one or more of these enumerated IUs (e.g., from about one amount that provides one of the enumerated IUs to about another amount that provides another of the enumerated IUs).

A dietary supplement of a Supplement Formulation H can contain any number of different antioxidants. For example, a dietary supplement of a Supplement Formulation H can contain one, two, three, four, five, six, seven, eight, nine, ten, or more different antioxidants. Any appropriate method can be used to obtain antioxidants. For example, extraction can be used to obtain a preparation of antioxidants. In some cases, antioxidants can be extracted from naturally-occurring sources, such as plants. In particular, *Ginkgo biloba* and blueberry can be used as sources of antioxidants. In some cases, a solid phase extraction process can be performed using *Ginkgo biloba* leafs as a source material to obtain a preparation of antioxidant. In some cases, an antioxidant to be included in a dietary supplement of a Supplement Formulation H can be derived from blueberry skin. A dietary supplement of a Supplement Formulation H can contain any appropriate amount of an antioxidant. For example, a dietary supplement of a Supplement Formulation H can contain from 0.01 µg to about 0.5 g (e.g., from about 0.01 µg to about 250 mg; from about 0.01 µg to about 100 mg; from about 0.1 µg to about 50 mg; from about 1 µg to about 500 mg; from about 10 µg to about 500 mg; or from about 100 µg to about 500 mg) of antioxidant. In some cases, a dietary supplement of a Supplement Formulation H can contain about 1, 2, 3, 4, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 mg or more of an antioxidant, about any amount of antioxidant between these enumerated amounts, or any range of antioxidant amounts encompassing one or more of these enumerated amounts (e.g., from about one of the enumerated amounts of antioxidant to about another of the enumerated amounts of antioxidant). In some cases, between about 0.01 percent to about 90 percent (e.g., between about 0.01 percent to about 80 percent; between about 0.01 percent to about 70 percent; between about 0.01 percent to about 60 percent; between about 0.1 percent to about 90 percent; between about 1 percent to about 90 percent; or between about 10 percent to about 90 percent) of a dietary supplement of a Supplement Formulation H can be antioxidants. In some cases, a dietary supplement of a Supplement Formulation H can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90 percent or more of an antioxidant, about any percentage of antioxidant between these enumerated percentages, or any range of antioxidant amounts encompassing one or more of these enumerated percentages (e.g., from about one of the enumerated percentages of antioxidant to about another of the enumerated percentages of antioxidant).

In some cases, a dietary supplement of a Supplement Formulation H can include *Ginkgo biloba*. *Ginkgo biloba* can include any species of tree contained within the genus Ginkgo. *Ginkgo biloba* is also known as the Maidenhair Tree. Any appropriate type of *Ginkgo biloba* can be included in a dietary supplement of a Supplement Formulation H. In some cases, a *Ginkgo biloba* extract can be provided in a dietary supplement of a Supplement Formulation H. In some case, a *Ginkgo biloba* extract can be obtained from a *Ginkgo biloba* leaf. *Ginkgo biloba* can be in any form, for example, a solution, a powder, or a soluble powder.

In general, extraction is a process whereby the desired constituents of a source material (e.g., a fruit, vegetable, plant, or plant part) are removed using, for example, a solvent. To produce an extract, fruit, vegetable, plant, or plant part material can be first cleaned and dried, if necessary. Drying can be performed naturally (e.g., by air drying) or artificially (e.g., using warm-air fans or conveyor dryers). Fruit, vegetable, plant, or plant part material can then be ground, cut, or shredded using, for example, hammer action, pressure, friction, or impact cutting. Methods of removing the desired constituents from the plant material include, without limitation, organic solvent extraction, supercritical gas extraction, and steam distillation.

The ability to use a number of different solutes, diluents, extractants, and aqueous phases as well as rapid extraction kinetics for many separations, can make solvent extraction a powerful separation method. By way of example, there are a number of procedures for organic solvent extraction, including maceration (soaking and agitating the fruit, vegetable, plant, or plant part material with a solvent), percolation (repeated rinsing of the fruit, vegetable, plant, or plant part material with a solvent), and countercurrent extraction (continuous flow of a solvent in the opposite direction as the fruit, vegetable, plant, or plant part material).

Representative solvents include, without limitation, water, methanol, hexane, ethanol, benzene, toluene, and ether. Aqueous extracts, such as decoctions (produced by boiling the fruit, vegetable, plant, or plant part material such as hard tissues), infusions (produced by steeping the fruit, vegetable, plant, or plant part material such as soft tissues), or macerations, can also be produced. In some cases, numerous separation procedures can be used to further purify desired components or remove unwanted or contaminating components. Examples of such separation procedures include, without limitation, decanting, filtration, sedimentation, centrifugation, heating, adsorption, precipitation, chromatography, or ion exchange. The resulting products can be subsequently evaporated, vaporized, lyophilized, spray dried, freeze-dried, or vacuum dried.

In some cases, a dietary supplement of a Supplement Formulation H can contain one or more radical scavengers, antioxidants, reducing agents, or mixtures thereof. For example, a dietary supplement of a Supplement Formulation H can contain one or more radical scavengers, antioxidants, reducing agents, or mixtures thereof in an amount that effectively reduces oxidation or degradation of other ingredients present within the supplement. Examples of radical scavengers and antioxidants include, without limitation, ascorbic acid, flavonoids, flavongycosides, anthocyanins, tocopherols, D-alpha-tocopherol or other Vitamin E, tocoptrienols, and carotenoids, and butyl hydroxytoluene. Sodium bisulfite is an example of a reducing agent that can be incorporated into a dietary supplement of a Supplement Formulation H.

In some cases, a dietary supplement of a Supplement Formulation H can contain phosphatidylserine, DHA, EPA, antioxidants, and *Ginkgo biloba*. The weight ratio of phosphatidylserine to other, optional ingredients (e.g., DHA, EPA, antioxidants, *Ginkgo Biloba*, and other additives) can be from about 1:20 to about 4:1. The ratio can be based, for example, on the dry weight of each ingredient or extract.

In some cases, a dietary supplement of a Supplement Formulation H can be designed to contain the following: 60 mg of DHA, 60 mg of EPA, 100 mg of phosphatidylserine, 40 mg of *Ginkgo biloba* extract, 17 mg of blueberry powder, 6.7 mg of α-tocopherol, and 14 mg of phosphatidylcholine.

A dietary supplement of a Supplement Formulation H can be ingested. For example, a dietary supplement of a Supplement Formulation H can be administered orally or intragastrically. Any amount of a dietary supplement of a Supplement Formulation H can be administered to a mammal. The dosages of a dietary supplement of a Supplement Formulation H can depend on many factors, including the mode of administration. The amount of phosphatidylserine, DHA, EPA, antioxidants, and *Ginkgo Biloba* contained within a single dose of a dietary supplement of a Supplement Formulation H can be an amount that can effectively maintain a desired result in a mammal without inducing significant toxicity. For example, a dietary supplement of a Supplement Formulation H can be formulated in a dose such that an individual receives from about 10 mg up to about 1000 mg of phosphatidylserine, from about 10 mg up to about 2000 mg of DHA, from about 10 mg up to about 2000 mg of EPA, from about 1 mg up to about 500 mg of antioxidants, from about 5 mg up to about 200 mg of *Ginkgo Biloba*, per day.

In some cases, a dietary supplement of a Supplement Formulation H can include phosphatidylserine, DHA, EPA, antioxidants, and *Ginkgo biloba*. The phosphatidylserine can be present from about 2 percent to about 20 percent by weight. The DHA can be present from about 2 percent to about 15 percent by weight. The EPA can be present from about 2 percent to about 15 percent by weight. The antioxidants can be present from about 0.5 percent to about 10 percent by weight. The *Ginkgo biloba* can be present from about 0.5 percent to about 10 percent by weight.

In some cases, a dietary supplement of a Supplement Formulation H can include between 17 and 170 mg of phosphatidylserine, between 17 and 130 mg of DHA, between 17 and 130 mg of EPA, between 4 and 90 mg of antioxidants, and between 4 and 90 mg of *Ginkgo biloba*.

In some cases, a dietary supplement of a Supplement Formulation H can include between about 100 and about 1000 mg of phosphatidylserine complex, between about 17 and about 130 mg of DHA, between about 17 and about 130 mg of EPA, between about 4 and about 90 mg of *Ginkgo biloba*, and between 4 and 90 mg of antioxidants.

In some cases, a dietary supplement of a Supplement Formulation H can include about 500 mg of phosphatidylserine complex, about 60 mg of DHA, about 60 mg of EPA, and an amount of Vitamin E that provides about 10 IUs of Vitamin E.

In some cases, a dietary supplement of a Supplement Formulation H can include an effective amount of two different omega-3-fatty acids, a phospholipid, an antioxidant, a flavonoid, and a glycoside. One of the omega-3-fatty acids can be EPA. One of the omega-3 fatty acids can be DHA. The phospholipid can be phosphatidylserine. The phospholipid can be phosphatidylcholine. The antioxidant can be D-alpha-tocopherol or other Vitamin E. The flavonoid can be a blueberry extract or a *Ginkgo biloba* extract. The glycoside can be a *Ginkgo biloba* extract.

In one example, a dietary supplement of a Supplement Formulation H can include:

| | |
|---|---|
| Fish Oil | 60 mg EPA, 60 mg DHA |
| PS (Phosphatidylserine) | 100 mg |
| PC (Phosphatidylcholine) | 14 mg |
| Ginkgo Biloba Extract | 40 mg |
| Blueberry Extract | 17 mg |
| Vitamin E (as d-alpha tocopherol) | 10 IU |

In some cases, a dietary supplement of a Supplement Formulation H can be made and used as described in U.S. Patent Application Publication No. 2009/0175968, which is herein incorporated by reference in its entirety. For example, a dietary supplement of a Supplement Formulation H can be made to have the ingredients as set forth in U.S. Patent Application Publication No. 2009/0175968.

Supplement Formulation I

A dietary supplement of a Supplement Formulation I can include, without limitation, Vitamin $K_2$ and Vitamin $D_3$ (cholecalciferol). Vitamin $K_2$ and Vitamin $D_3$ can be obtained commercially. For example, Vitamin $K_2$ can be obtained from Japan Bio Science Laboratory Co., Ltd. (Japan), and Vitamin $D_3$ can be obtained from Prinova USA (IL, United States).

In some cases, a dietary supplement of a Supplement Formulation I can contain any appropriate amount of Vitamin $K_2$. In some cases, a dietary supplement of a Supplement Formulation I can contain between about 10 mg and about 400 mg (e.g., between about 50 mg and about 150 mg) of Vitamin $K_2$. In some cases, a dietary supplement of a Supplement Formulation I can be formulated to contain the above referenced amount of Vitamin $K_2$ such that it can be conveniently administered.

In some cases, a dietary supplement of a Supplement Formulation I can contain any appropriate amount of Vitamin $D_3$. In some cases, a dietary supplement of a Supplement Formulation I can contain between about 200 mg and about 4000 mg (e.g., between about 400 mg and about 2500 mg) of Vitamin $D_3$. In some cases, a dietary supplement of a Supplement Formulation I can be formulated to contain the above reference amounts of Vitamin $D_3$ such that it can be conveniently administered.

In one example, a given dosage (e.g., a daily dose) of a dietary supplement of a Supplement Formulation I can be designed to provide the following effective amounts:

| | |
|---|---|
| Vitamin $D_3$ | 2,000 IU |
| Vitamin $K_2$ | 90 μg |

In another example, a given dosage (e.g., a daily dose) of a dietary supplement of a Supplement Formulation I can be designed to provide the following effective amounts:

| | |
|---|---|
| Vitamin $D_3$ | 4,000 IU |
| Vitamin $K_2$ | 200 µg |

Supplement Formulation J

A dietary supplement of a Supplement Formulation J can include, without limitation, CoQ10, alpha lipoic acid, and one or more forms of tocotrienol. In some cases, CoQ10 can be obtained commercially. For example, CoQ10 can be obtained from Xiamen Kingdomway Group Company (China). Tocotrienol can be obtained from Caroteh Inc. (Edison, N.J.). A tocotrienol blend can be obtained as described elsewhere (e.g., U.S. Pat. No. 6,596,306).

In some cases, a dietary supplement of a Supplement Formulation J can contain any appropriate amount of CoQ10. In some cases, a dietary supplement of a Supplement Formulation J can contain between about 10 mg and about 200 mg (e.g., between about 30 mg and about 100 mg) of CoQ10. In some cases, a dietary supplement of a Supplement Formulation J can be formulated to contain an amount of CoQ10 such that a daily dose as described above can be conveniently administered.

In some cases, a dietary supplement of a Supplement Formulation J can contain any appropriate amount of alpha lipoic acid. In some cases, a dietary supplement of a Supplement Formulation J can contain between about 10 mg and about 200 mg (e.g., between about 30 mg and about 100 mg) of alpha lipoic acid. In some cases, a dietary supplement of a Supplement Formulation J can be formulated to contain an amount of alpha lipoic acid such that a daily dose as described above can be conveniently administered.

In some cases, a dietary supplement of a Supplement Formulation J can contain any appropriate amount of tocotrienol. In some cases the formulation can include different forms of tocotrienol, such as for example, d-alpha-tocotrienol, d-beta-tocotrienol, d-gamma-tocotrienol, and d-delta-tocotrienol. In some cases, a dietary supplement of a Supplement Formulation J can contain between about 1 mg and about 100 mg (e.g., between about 5 mg and about 15 mg) of tocotrienol. In some cases, a dietary supplement of a Supplement Formulation J can be formulated to contain an amount of tocotrienol such that a daily dose as described above can be conveniently administered.

In one example, a given dosage (e.g., a daily dose) of a dietary supplement of a Supplement Formulation J can be designed to provide the following effective amounts:

| | |
|---|---|
| Coenzyme $Q_{10}$ | 70 mg |
| Alpha Lipoic Acid | 70 mg |
| d-alpha-Tocotrienol | 2.5 mg |
| d-beta-Tocotrienol | 0.25 mg |
| d-gamma-Tocotrienol | 3.75 mg |
| d-delta-Tocotrienol | 1.4 mg |

Supplement Formulation K

A dietary supplement of a Supplement Formulation K can include, without limitation, one or more sterol compounds, one or more fatty acid compounds, or a mixture of one or more sterol compounds and one or more fatty acid compounds. In some cases, a dietary supplement of a Supplement Formulation K can include one or more of the following: a sterol compound (e.g., a phytosterol compound), a fatty acid compound (e.g., an omega 3 fatty acid compound), a carboxylic acid ester (e.g., a small carboxylic acid ester), a surfactant (e.g., lecithin), and an enzyme (e.g., papain) or enzyme blend (e.g., bromelain). Other optional ingredients of a dietary supplement of a Supplement Formulation K can include antioxidants, reducing agents, and radical scavengers. A package containing a dietary supplement of a Supplement Formulation K can include a label recommending a serving size of at least 1 g of one or more sterol compounds and/or at least 300 mg of one or more fatty acid compounds per day.

A dietary supplement of a Supplement Formulation K can be designed to contain a high percentage of a mixture of one or more sterol compounds with one or more fatty acid compounds. For example, 50, 55, 60, 65, 70, 75, 80, 85, 90, 95, or more percent of the material of a dietary supplement of a Supplement Formulation K can be sterol and fatty acid compounds. A mixture of sterol and fatty acid compounds can be a homogeneous mixture. A ratio of the total sterol compounds to the total fatty acid compounds can be ≤5:1. In some cases, a capsule form of a dietary supplement of a Supplement Formulation K can lack beeswax or other typical fillers. In addition, a capsule form of a dietary supplement of a Supplement Formulation K can provide material that is homogeneous and stable. Further, a capsule form of a dietary supplement of a Supplement Formulation K can allow the formulated material to be absorbed by the user. For example, a dietary supplement of a Supplement Formulation K can be formulated such that 1, 2, 3, 4, 5, 6, 7, 8, 9, 10, 15, 20, 25, 30, 35, 40, 45, 50, 60, 70, 80, 90, or more percent of a particular compound (e.g., sterol compound or fatty acid compound) formulated within the dietary supplement is absorbed.

In some cases, a dietary supplement of a Supplement Formulation K can contain a phytosterol compound and an omega 3 fatty acid compound. A dietary supplement of a Supplement Formulation K can have a ratio of the total sterol compounds to total fatty acid compounds of ≤5:1 (e.g., about 4.5:1, 4:1, 3.5:1, 3:1, 2.5:1, 2:1, 1.5:1, 1:1, or 0.5:1). A dietary supplement of a Supplement Formulation K can be provided as a nutritional supplement with a label recommending a serving size of at least 1 g (e.g., 1 g, 1.3 g, 1.5 g, 1.7 g, 1.8 g, 2.0 g, 2.5 g, 2.75 g, 3.0 g, 3.25 g, or 3.5 g) of the one or more sterol compounds and/or at least 300 mg of the one or more fatty acid compounds (e.g., ω-3 fatty acid compounds) per day. In some cases, a dietary supplement of a Supplement Formulation K can contain other ingredients such as one or more small chain carboxylic acid esters, one or more surfactants, one or more enzymes or enzyme blends, one or more antioxidants, one or more reducing agents, or one or more radical scavengers. For example, a dietary supplement of a Supplement Formulation K can contain a phytosterol compound and a small carboxylic acid ester. In some cases, a dietary supplement of a Supplement Formulation K can contain an ω-3 fatty acid compound and a small carboxylic acid ester. In some cases, a dietary supplement of a Supplement Formulation K can contain a phytosterol compound, an ω-3 fatty acid compound, and a small carboxylic acid ester. In some cases, a dietary supplement of a Supplement Formulation K can contain a phytosterol compound, an ω-3 fatty acid compound, and an enzyme or enzyme blend. Dietary supplement of a Supplement Formulation K having a phytosterol compound and a ω-3 fatty acid compound can contain an antioxidant. A surfactant can be included in any of the dietary supplements of a Supplement Formulation K. For example, a dietary supplement of a Supplement Formulation K can contain a phytosterol compound, an ω-3 fatty acid compound, a small carboxylic acid ester, an antioxidant, a surfactant, and an enzyme or enzyme blend. Typically, a dietary supplement of a Supplement Formulation K is formulated as soft gel capsules or hard shell capsules without the addition of beeswax or other fillers. Soft gel cap or hard shell caplet formulations described herein can exhibit improved stability and homogeneity of the material contained within the soft gel cap or hard shell caplet.

Sterol Compounds

As described herein, a dietary supplement of a Supplement Formulation K can contain a sterol compound such as a phytosterol compound. In some cases, the sterol can be synthetic. The term "sterol" includes, without limitation, plant, animal, and synthetic sterols, sterol esters, stanols, and stanol esters. Plant sterols (and sterol esters) are naturally occurring substances present in the diet as minor components of vegetable oils, while plant stanols (and stanol esters) are hydrogenation compounds of the plant sterols.

A sterol compound can have the following structure:

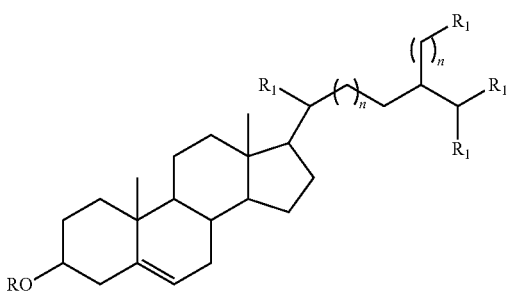

Structure Ia, where $R_1$ can be —H, a linear or branched, saturated or unsaturated C1, C2, C3, C4, C5, or C6 alkyl, —OH, or —OR", where R" can be a linear or branched, saturated or unsaturated C1, C2, C3, C4, C5, or C6 alkyl or

where n can be zero, one, or two; and where R can be H, R', or

Alternatively, a sterol compound can have the following structure:

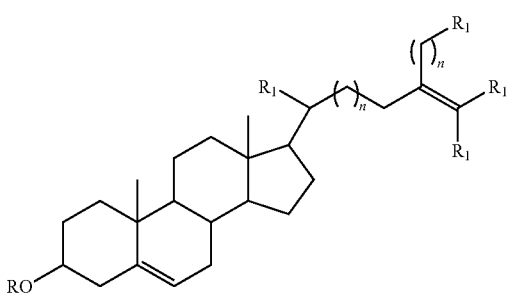

Structure Ib, where $R_1$ and R are defined as in Structure Ia above.

Some compounds according to Structures Ia or Ib can be called phytosterols or phytosterol esters. In addition, they can be provided in a free alcohol (sterol) or esterified form. When R is H, the compound can be referred to as a sterol. On the other hand, when R in Structure Ia or Ib is

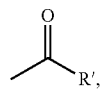

the compound can be called a sterol ester. In these embodiments, R' can be a linear or branched, saturated or unsaturated alkyl chain having 6 to 30 carbon atoms. In certain embodiments, R' is a linear or branched, saturated or unsaturated alkyl chain having 12 to 18 carbon atoms.

Sterol compounds (e.g., phytosterols and phytosterol esters) can be obtained commercially from, e.g., Cargill, Inc. (Minneapolis, Minn.), Loders and Croklaan (Channahon, Ill.), Cognis Nutrition and Health (La Grange, Ill.), Forbes Meditech (Vancouver, B.C. Canada), and ADM (Decatur, Ill.) and can demonstrate a range of sterol profiles. For example, Vegapure™ 95 sterol esters from Cognis Nutrition and Health is a mixture of sterol esters produced from a mixture of soy, rapeseed and other vegetable oil distillates. Vegapure™ 95 can include at least 90% (e.g. about 91%, 92%, 93%, 94%, 95%, 96%, 97%, 98%, or 99%) free sterols and sterol esters, with β-sitosterol ester ranging from about 40% to about 60% by weight, campesterol ester ranging from about 20% to about 40% by weight, stigmasterol ester ranging from about 12% to about 23% by weight, brassicasterol ester ranging from about 0 to about 12% by weight, and free sterols ranging from 0% to about 6% by weight. CoroWise™ Phytosterol Esters from Cargill, Inc. has a typical phytosterol content of greater than 88%, with sitosterol ranging from about 40-58%, campesterol ranging from about 20-28%, and stigmasterol ranging from about 14-23%. ADM Phytosterols 040095 include a mixture of sterols having about 40-58% by weight β-sitosterol, 20-30% by weight campesterol, 14-22% by weight stigmasterol, 0-6% by weight brassicasterol, 0-5% by weight sitostanol, and total phytosterols at a minimum of 90% by weight. In addition, sterol compounds can be synthesized and/or obtained from natural sources such as soy oil, canola oil, or wheat germ oil as described elsewhere (U.S. Pat. Nos. 6,211,406; 5,502,045; 6,087,353; and 4,897,224).

Suitable examples of phytosterol esters that can be used to prepare a dietary supplement of a Supplement Formulation K include, without limitation, beta-sitosterol laurate ester, alpha-sitosterol laurate ester, gamma-sitosterol laurate ester, campesterol myristearate ester, stigmasterol oleate ester, campesterol stearate ester, beta-sitosterol oleate ester, beta-sitosterol palmitate ester, beta-sitosterol linoleate ester, alpha-sitosterol oleate ester, gamma-sitosterol oleate ester, beta-sitosterol myristearate ester, beta-sitosterol ricinoleate ester, campesterol laurate ester, campesterol ricinoleate ester, campesterol oleate ester, campesterol linoleate ester, stigmasterol linoleate ester, stigmasterol laurate ester, stigmasterol caprate ester, alpha-sitosterol stearate ester, gamma-sitosterol stearate ester, alpha-sitosterol myristearate ester, gamma-sitosterol palmitate ester, campesterol ricinoleate ester, stigmasterol ricinoleate ester, campesterol ricinoleate ester, beta-sitosterol, alpha-sitosterol, gamma-sitosterol, campesterol, stigmasterol, and stigmasterol stearate ester.

In some embodiments, a sterol compound can have the following structure:

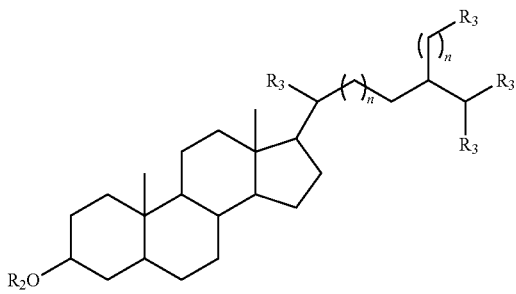

Structure IIa. In these embodiments, $R_3$ can be —H, a linear or branched, saturated or unsaturated C1, C2, C3, C4, C5, or C6 alkyl, —OH, or —OR"", where R"" can be a linear or branched, saturated or unsaturated C1, C2, C3, C4, C5, or C6 alkyl or

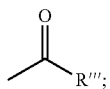

n can be zero, one, or two; and $R_2$ can be H, R''' or

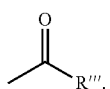

In some cases, a sterol compound can have the following formula:

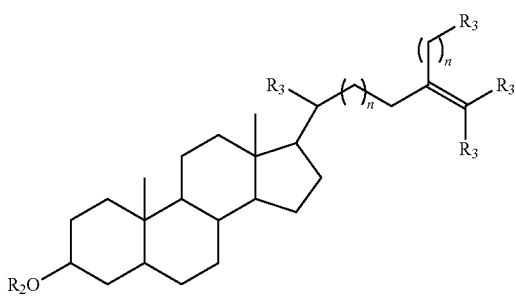

Structure IIb, where $R_2$ and $R_3$ are defined as for Structure IIa above.

When $R_2$ is H, the compound can be referred to as a phytostanol. When $R_2$ is

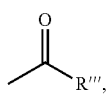

the compound can be called a phytostanol ester. In these embodiments, R''' can be a linear or branched, saturated or unsaturated alkyl chain having 6 to 26 carbon atoms. In certain embodiments, R''' can be a linear or branched, saturated or unsaturated alkyl chain having 12 to 22 carbon atoms.

Sterol compounds such as phytostanols and phytostanol esters can be obtained commercially from, e.g., Forbes Meditech (Vancouver, B.C. Canada), or can be readily synthesized. Alternatively, phytostanols and phytostanol esters can be obtained from natural sources such as soy oil, canola oil, or wheat germ oil as described elsewhere (U.S. Pat. Nos. 6,211,206; 5,502,045; 6,087,353; and 4,897,224).

Examples of phytostanol esters that can be used to make a dietary supplement of a Supplement Formulation K include, without limitation, beta-sitostanol laurate ester, campestanol myristearate ester, stigmastanol oleate ester, campestanol stearate ester, beta-sitostanol oleate ester, beta-sitostanol palmitate ester, beta-sitostanol linoleate ester, beta-sitostanol myristearate ester, beta-sitostanol ricinoleate ester, campestanol laurate ester, campestanol ricinoleate ester, campestanol oleate ester, campestanol linoleate ester, stigmastanol linoleate ester, stigmastanol laurate ester, stigmastanol caprate ester, stigmastanol stearate ester, alpha-sitostanol laurate ester, gamma-sitostanol laurate ester, alpha-sitostanol oleate ester, gamma-sitostanol oleate ester, alpha-sitostanol stearate ester, gamma-sitostanol stearate ester, alpha-sitostanol myristearate ester, gamma-sitostanol palmitate ester, campestanol ricinoleate ester, stigmastanol ricinoleate ester, campestanol ricinoleate ester, beta-sitostanol, alpha-sitostanol, gamma-sitostanol, campestanol, and stigmastanol.

Sterol compounds of a dietary supplement of a Supplement Formulation K can have a melting point below 145° C. In other embodiments, the sterol compounds can have a melting point below 85° C., below 65° C., or below 45° C.

A dietary supplement of a Supplement Formulation K can contain any appropriate type of sterol compound such as a phytosterol, phytosterol ester, phytostanol, or phytostanol ester. In addition, a dietary supplement of a Supplement Formulation K can contain any appropriate amount of sterol compounds (e.g., 10, 25, 50, 100, 200, 250, 300, 325, 350, 375, 400, 425, 450, 475, 500, 525, 550, 575, 600, 625, 650, 675, 700, 750, 800, or 900 mg). For example, between 35 to 95 percent (e.g., from 35 to 95 percent, from 50 to 95 percent, from 75 to 95 percent, from 85 to 95 percent, from 35 to 85 percent, from 35 to 75 percent, or from 35 to 55 percent) of a dietary supplement of a Supplement Formulation K can contain sterol compounds. In some cases, a dietary supplement of a Supplement Formulation K can be designed to contain multiple sterol compounds in any relative ratio (e.g., 1:1, 2:1, 3:1, 4:1, 5:1, 6:1, 7:1, 8:1, 9:1, or 10:1). In certain cases, a dietary supplement of a Supplement Formulation K can be a nutritional supplement with a label indicating that a suggested serving size includes greater than 1 g (e.g., about 1.1, 1.2, 1.3, 1.4, 1.5, 1.6, 1.7, 1.8, 1.9, 2.0, 2.1, 2.2, 2.3, 2.4, 2.5, 2.6, 3.0, 3.5 g or more) of total sterol compounds per day.

Typically, a dietary supplement of a Supplement Formulation K can be designed to contain a phytosterol ester compound or mixtures thereof. In addition, a dietary supplement of a Supplement Formulation K can be designed to contain one or more phytosterol ester compounds in a total amount ranging from about 45% to about 95% by weight of the supplement. In certain embodiments, one or more phytosterol ester compounds can be provided in a total amount from about 45% to about 60% by weight of the supplement. In other embodiments, one or more phytosterol ester compounds can be provided in a total amount of about 70% to about 85% by weight of the dietary supplement of a Supplement Formulation K.

In some cases, a dietary supplement of a Supplement Formulation K can contain one or more phytosterol compounds (e.g., a compound according to Structure Ia or Ib where R in Structure I is H). In certain embodiments, one or more phytosterols can be present in a total amount from about 1% to about 85% by weight of the supplement. In certain compositions, one or more phytosterol compounds may be present in a total amount from about 1% to about 10% by weight of the supplement. In other compositions, one or more phytosterols can be present in a total amount of from about 40% to about 55%, or from about 70% to about 85% by weight of the dietary supplement of a Supplement Formulation K.

In certain embodiments, a dietary supplement of a Supplement Formulation K can contain one or more phytostanol ester compounds, e.g., in a total amount of from about 45% to about 95% by weight of the supplement. In certain embodiments, one or more phytostanol ester compounds can be provided in a total amount of about 45% to about 60% by weight of the supplement. In other embodiments, one or more phytostanol ester compounds can be provided in a total amount of about 70% to about 85% by weight of the dietary supplement of a Supplement Formulation K.

In some cases, one or more phytostanol compounds can be present in a total amount from about 1% to about 85% by weight of the dietary supplement of a Supplement Formulation K. In some cases, one or more phytostanols can be present in a total amount of from about 1% to about 10%, from about 40% to about 55%, or from about 70% to about 85% by weight of the dietary supplement of a Supplement Formulation K.

Fatty Acid Compounds

A dietary supplement of a Supplement Formulation K can contain one or more fatty acid compounds (e.g., ω-3 fatty acid compounds). An ω-3 fatty acid for use in a dietary supplement of a Supplement Formulation K can have the following structure:

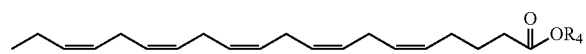

Structure III. ω-3 fatty acids can generally be in the simple form (e.g., where $R_4$ is H) or alternatively in the glyceride ester form. For example, $R_4$ can be hydrogen; a linear or branched, saturated or unsaturated C2-C12 alkyl chain; or a 2-hydroxypropyl, hydroxyethyl, tocopheryl, alkyl, or glyceryl (e.g., mono-, di-, or triglyceride) ester. Compounds according to Structure III are generally known as eicosapentanoic acid (EPA) and derivatives thereof.

In some embodiments, an ω-3 fatty acid compound can have the following structure:

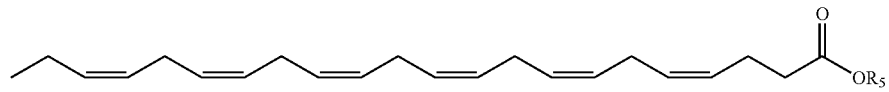

Structure IV, where $R_5$ can be hydrogen; a linear or branched, saturated or unsaturated C2-C12 alkyl chain; or a 2-hydroxypropyl, hydroxyethyl, tocopheryl, alkyl, or glyceryl (e.g., mono-, di-, or triglyceride) ester. Compounds according to Structure IV are known as docosahexanoic acid (DHA) and derivatives thereof.

In other embodiments, an ω-3 fatty acid compound can have the following structure:

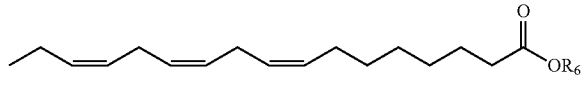

Structure V, where $R_6$ can be hydrogen; a linear or branched, saturated or unsaturated C2-C12 alkyl chain; or a 2-hydroxypropyl, hydroxyethyl, tocopheryl, alkyl, or glyceryl (e.g., mono-, di-, or triglyceride) ester. Compounds according to Structure V are known as α-linolenic acid (ALA) and derivatives thereof.

Fatty acid compounds such as ω-3 fatty acid compounds can be obtained from fish oils or vegetable oils, or synthesized. In some cases, fatty acid compounds such as ω-3 fatty acid compounds can be formulated in a dietary supplement of a Supplement Formulation K as a fish oil or vegetable oil or mixture thereof. For example, a fish oil containing DHA, EPA, or both, and/or a vegetable oil containing ALA (or derivatives thereof) can be used to make a dietary supplement of a Supplement Formulation K. Fish oils are available commercially from BLT Berg Lipidtech AS, Clover Corporation, Denofa AS, Bioriginal Food and Science Corp., ProNova Biocare, BASF, and Nutri Science Innovations LLC, and can demonstrate a range of ω-3 fatty acid profiles. In certain cases, a fish oil can contain about 11-14% DHA and about 16-19% EPA, and a total ω-3 fatty acid content of about 33-41%. For example, a fish oil can contain about 12% DHA and about 18% EPA. In other cases, a fish oil can contain about 30-33% EPA and about 20-22% DHA, and a total ω-3 fatty acid content of about 50-67%. In other cases, a fish oil can contain about 50-55% DHA and about 5-10% EPA. In yet other cases, a fish oil can contain about 50-55% EPA and about 5-10% DHA. In other examples, a fish oil can contain at least 20% DHA and at least 25% EPA, and a total ω-3 fatty acid content of at least 60%, e.g., at least 65%. In yet other cases, a fish oil can contain about 5% EPA and about 25% DHA, and a total ω-3 fatty acid content of about 30%, e.g., about 35%. A vegetable oil can contain greater than 10% ω-3 fatty acids by weight, or greater than 25% ω-3 fatty acids by weight. Any appropriate type of vegetable oil can be used to make a dietary supplement of a Supplement Formulation K including, without limitation, canola, flaxseed, or rapeseed oil.

In addition to use of a pure fish oil or vegetable oil, a fish oil or vegetable oil containing EPA, DHA, and/or ALA (or derivatives thereof) can be modified by, e.g., the addition of purified EPA, DHA, or ALA (or derivatives thereof) to result in a particular ratio or amount of EPA, DHA, or ALA (or derivatives thereof). In other embodiments, purified DHA, EPA, or ALA, or derivatives thereof, can be used to make a dietary supplement of a Supplement Formulation K. In certain embodiments, a ratio of EPA to DHA, or derivatives thereof, can be from about 1:5 to about 5:1, or from about 1:2 to about 2:1, or from about 1.5:1 to about 1:1.5. For example, a fish oil can contain EPA and DHA at a ratio of about 1.5:1.

Typically, a dietary supplement of a Supplement Formulation K can contain a fish oil or a vegetable oil, or both, in a range from about 10% to about 55% by weight of the supplement, or from about 10% to about 30% by weight of the supplement. In other embodiments, EPA, DHA, and/or ALA, or derivatives thereof, can be used in purified form to make a dietary supplement of a Supplement Formulation K. The combined amount of EPA and DHA (or derivatives thereof) can range from about 30% to about 55% by weight of the supplement. In certain embodiments, the combined amount of EPA and DHA can range from about 20% to about 40% by weight of the supplement. In other embodiments, the combined amount of EPA and DHA can range from about 12% to about 16% by weight of a dietary supplement of a Supplement Formulation K.

Fish oils, vegetable oils, purified EPA, DHA, and ALA, and derivatives thereof such as DHA, EPA, or ALA esters or glycerides can be obtained commercially from, for example, Croda, Inc. (Parsippany, N.J.), Roche Vitamins Ltd. (Parsippany, N.J.), Martek (Boulder, Colo.), Maritex (Sortland, Norway), Seven Seas, Pronova (Lysker, Norway), and Loder Croklann Lipid Nutrition (Channahon, Ill.), and Cargill, Inc. (Minneapolis, Minn.). In certain embodiments, ω-3 fatty acids, particularly those according to Structure V (e.g., ALA) can be provided in a flax seed oil mixture, a canola oil mixture, a walnut oil mixture, or mixtures thereof.

In some cases, a dietary supplement of a Supplement Formulation K can include a label indicating that a suggested serving size includes at least 300 mg (e.g., about 300, 350, 400, 420, 450, 500, 500-600, 600-900, 1000, 1100, 1200, 900-1200, 1200-1500 mg, 1500 mg-2 g, 2 g-2.5 g, 2.5 g-3 g, or more) of total ω-3 fatty acids per day. One or more ω-3 fatty acids can be derived from one or more fish or vegetable oils, purified ω-3 fatty acids, or mixtures thereof. In some embodiments, a dietary supplement of a Supplement Formulation K can include a label indicating that a suggested serving size includes at least 300 mg of DHA and EPA per day.

In dietary supplements of a Supplement Formulation K containing one or more phystosterol compounds and one or more ω-3 fatty acid compounds, a ratio of the combined amount of sterol compounds (e.g., phytosterol compounds) relative to the combined amount of fatty acid compounds (e.g., ω-3 fatty acid compounds) can be ≤about 5:1 (e.g., about 4:1, 3:1, 2:1, or 1.5:1).

Carboxylic Acid Esters

A dietary supplement of a Supplement Formulation K can contain one or more carboxylic acid esters (e.g., a small carboxylic acid ester) having the following structure:

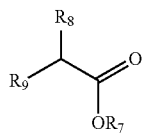

Structure VI, where $R_7$ can be a linear or branched, saturated or unsaturated alkyl group having 1 to 12 carbon atoms (e.g., methyl, ethyl, butyl, isopropyl); $R_8$ and $R_9$ can be, independently, —H, —OH; —OR, wherein R is a linear or branched alkyl group having 1 to 10 carbon atoms; an acyl group (e.g., acetate, propionate, butyrate); or a linear or branched $C_1$-$C_6$ alkyl group containing a carboxylate ester.

Examples of small carboxylic acid esters include, without limitation, ethyl lactate, propyl acetate, triethyl citrate, diethyl maleate, diethylmalonate, diethyl succinate, triisopropyl citrate, diethyl tartrate, propyl lactate, butyl acetate, tripropylcitrate, diisopropyl maleate, dibutylmalonate, dipropyl succinate, trimethyl citrate, and dihexyl tartrate.

Typically, small carboxylic acid esters can be present in an amount from about 0.01% to about 15% by weight of a dietary supplement of a Supplement Formulation K, from about 0.1 to about 10%, or from about 0.5 to about 5% by weight of the supplement.

Enzymes and Enzyme Blends

A dietary supplement of a Supplement Formulation K can contain an enzyme or an enzyme blend. Examples of enzymes or enzyme blends include, without limitation, bromelain, papain, fungal proteases, acid stable proteases, neutral stable proteases, alkaline stable proteases, and mixtures thereof. The enzyme or enzyme blend can be derived from animals, plants, or fungi. Generally, the enzyme or enzyme blend is provided in an amount ranging from about 0.1% to about 5% by weight of the supplement, or from about 0.5% to about 2.5% by weight of the supplement.

In certain embodiments, the enzyme blend bromelain is used to make a dietary supplement of a Supplement Formulation K. Bromelain is the generic name for a family of sulfhydryl-containing proteolytic enzymes obtained from the pineapple plant. A bromelain enzyme blend generally contains a sulfydryl proteolytic fraction, a peroxidase, an acid phosphatase, several protease inhibitors, and calcium.

Enzymes or enzyme blends can be obtained commercially from, for example, National Enzyme Company (Forsyth, Mo.), American Laboratories, Inc. (Omaha, Nebr.), Botanical International (Long Beach, Calif.) or Marcor Development Corporation (Carlstadt, N.J.). Enzymes or enzyme blends used to make a composition provided herein can be food and/or pharmaceutical grade.

Surfactants

A dietary supplement of a Supplement Formulation K can be designed to contain a surfactant that wets, solubilizes, and/or emulsifies lipophilic components such as sterol compounds (e.g., phytosterol compounds) and/or fatty acid compounds (e.g., fish oil components and ω-3 fatty acids such as EPA, DHA, or ALA). Typically, a surfactant is a food grade surfactant. A surfactant can be anionic, cationic, zwitterionic, or non-ionic. In certain embodiments, a surfactant can have a surface tension below 70 dyne/cm$^2$, or below 40 dyne/cm$^2$. A surfactant can have a hydrophilic/lipophilic balance of less than 20, or less than 10. See, e.g., *Surfactants in Chemistry*, J. Falbe, Ed., Springer-Verlag (1989), pp: 149-152.

One or more surfactants can be used in any combination or relative ratio to make a dietary supplement of a Supplement Formulation K. Examples of surfactants include, without limitation, alkanoylglycerides, monoacylglycerides, or monoglycerides (e.g., from rapeseed, canola, and cottonseed oils); propylene glycol monoesters (e.g., propylene glycol monostearate); lactoylesters; stearic acid; sodium stearoyl lactylate; ethoxylated alcohols; ethoxylated fatty esters and fatty esters; ethyoxylated glycerol esters; phosphorous organic derivatives such as dodecyl phosphonic acid, dodecyl phosphate, decylphosphonic acid, decyl phosphate, dioctylphosphate, myristearylphosphonic acid, lecithin and lecithin derivatives; sorbitan derivatives such as polyoxyethylene sorbitan monolaurate, sorbitan oleate, sorbitan laurate, sorbitan palmitate, sorbitan stearate, sorbitan myristearate, sorbitan ricinoleate, sorbitan linoleneate, and sorbitan linoleate; stearoyl-2-lactylates of sodium or calcium; sucrose and glucose esters and derivatives thereof; sulfosuccinates and derivatives; and mixtures of any of the above. Sorbitan derivatives and phosphorous organic derivatives, such as lecithin, can be used as surfactants to increase stability of a dietary supplement of a Supplement Formulation K, particularly a dietary supplement of a Supplement Formulation K formulated as a soft gel cap or hard shell caplet, or to increase bioavailability of a sterol compound (e.g., a phytosterol compound) and/or a fatty acid compound (e.g., a ω-3 fatty acid compound). A surfactant can be included at a concentration of about 0.01% to about 15%, or from about 0.1% to about 10%, or from about 0.1% to about 7% by weight of the supplement.

Surfactants can be obtained commercially as described elsewhere ("McCutcheon's Emulsifiers and Detergents," Int'l Ed. (2001), The Manufacturing Confectioner Publishing Co., NJ, USA). Typically, a surfactant is present in an amount from about 0.01% to about 15% by weight of a supplement, or from about 0.1 to about 10%, or from about 0.1 to about 7% by weight of the supplement.

Radical Scavengers, Antioxidants, and Reducing Agents

A dietary supplement of a Supplement Formulation K can contain an agent such as a radical scavenger, an antioxidant, a reducing agent, and mixtures thereof. Radical scavengers, antioxidants, and reducing agents can be obtained commercially from common suppliers. Sodium bisulfate can be used as a reducing agent. Examples of radical scavengers and antioxidants include, without limitation, ascorbic acid, tocopheryl acetate, Coenzyme Q-10, tocopheryl palmitate, tocotrienol, retinyl palmitate, betacarotene, zeaxanthine, lutene, lycopene, retinyl acetate, polyphenolic-containing herbs or plant matter (e.g., green tea extracts or grape seed extracts), and butyl hydroxytoluene. Coenzyme Q-10 (CoQ-10) is a fat-soluble quinone that is structurally similar to vitamin K and is commonly known as ubiquinone. Mixtures of one or more radical scavengers, antioxidants, and reducing agents can be used to make a dietary supplement of a Supplement Formulation K. A radical scavenger, antioxidant, and/or reducing agent can be included in an amount ranging from about 0.01% to about 2% by weight of the supplement, or from about 0.1% to about 1% by weight.

Other Optional Ingredients

A dietary supplement of a Supplement Formulation K can contain additional optional ingredients. For example, optional coloring and/or flavoring agents, e.g., to reduce the odor associated with fish oil and fish oil components, can be included. In addition, a dietary supplement of a Supplement Formulation K can contain a pharmaceutically acceptable carrier for in vivo administration to a mammal, including, without limitation, preservatives and other additives such as, for example, botanical extracts.

In one example, a serving of a dietary supplement of a Supplement Formulation K can include:

| | |
|---|---|
| Vitamin C (as ascorbic acid) | 20 mg |
| Vitamin E (as d-alpha tocopherol) | 12 IU |
| Phytosterol Esters | 2000 mg |
| Fish Oil (165 mg EPA and 110 mg DHA | 1000 mg |
| Coenzyme Q10 | 30 mg |
| Alpha Lipoic Acid | 30 mg |

In some cases, a dietary supplement of a Supplement Formulation K can be made and used as described in U.S. Patent Application Publication No. 2005/0032757 or U.S. Patent Application Publication No. 2011/0038848, each of which is herein incorporated by reference in its entirety. For example, a dietary supplement of a Supplement Formulation K can be made to have the ingredients as set forth in U.S. Patent Application Publication No. 2005/0032757 or U.S. Patent Application Publication No. 2011/0038848.

Supplement Formulation L

A dietary supplement of a Supplement Formulation L can include, without limitation, calcium. Calcium can be obtained using any appropriate process. For example, calcium can be obtained as one or more of calcium carbonate, dicalcium phosphate, calcium citrate, calcium gluconate, or a calcium-amino acid/polyfructose complex. A suitable calcium supplement is sold by Melaleuca, Inc. (Idaho Falls, Id.) as Vitality Calcium Complete®.

In some cases, a dietary supplement of a Supplement Formulation L can contain any appropriate amount of calcium. In some cases, a dietary supplement of a Supplement Formulation L can contain between about 200 mg and about 1500 mg (e.g., between about 250 mg and about 1250 mg) of calcium. In some cases, a dietary supplement of a Supplement Formulation L can be formulated to contain an amount of calcium such that a daily dose of between about 500 mg and about 1500 mg (e.g., between about 750 and about 1250 mg) of calcium can be conveniently administered.

In some cases, a dietary supplement of a Supplement Formulation L can include additional components such as Vitamin $D_3$ and magnesium. In some cases, a dietary supplement of a Supplement Formulation L can have one of the following formulas.

Example Formula

| | |
|---|---|
| Vitamin D3 (as Colecalciferol) | 300 IU |
| Calcium (as calcium carbonate, dicalcium phosphate, calcium citrate, calcium gluconate, or a calcium-amino acid/polyfructose complex) | 750 mg |
| Magnesium (as magnesium oxide, magnesium lactate, magnesium citrate, or a magnesium-amino acid/polyfructose complex) | 150 mg |

Example Formula

| | |
|---|---|
| Vitamin D3 (as Colecalciferol) | 400 IU |
| Calcium (as calcium carbonate, dicalcium phosphate, calcium citrate, calcium gluconate, or a calcium-amino acid/polyfructose complex) | 1000 mg |
| Magnesium (as magnesium oxide, magnesium lactate, magnesium citrate, or a magnesium-amino acid/polyfructose complex) | 200 mg |

Example Formula

| | |
|---|---|
| Vitamin D3 (as Colecalciferol) | 500 IU |
| Calcium (as calcium carbonate, dicalcium phosphate, calcium citrate, calcium gluconate, or a calcium-amino acid/polyfructose complex) | 1250 mg |
| Magnesium (as magnesium oxide, magnesium lactate, magnesium citrate, or a magnesium-amino acid/polyfructose complex) | 250 mg |

Supplement Formulation M

Supplement Formulation M can provide ingredients selected to promote bone and joint health. For example, two suitable formula for a dietary supplement of a Supplement Formulation M may be Replenex® and Replenex® Extra Strength, both commercially available from Melaleuca, Inc. (Idaho Falls, Id.). In some cases, a dietary supplement of a Supplement Formulation M can be as described elsewhere (e.g., U.S. Pat. Nos. 6,713,096 and 7,138,149, both of which are incorporated by reference herein in their entireties).

Examples dietary supplements of a Supplement Formulation M include the following:

| Ingredient | Amount |
|---|---|
| Example #1 | |
| Glucosamine HCl | 510 mg |
| Calcium Carbonate | 269.9 mg |
| Ginger Root Extract | 60 mg |
| Microcrystalline Cellulose | 56 mg |
| Bromelain | 25 mg |
| Green Tea Extract Powder | 20 mg |
| Stearic Acid | 20 mg |
| Hydroxy Propyl Cellulose | 17.6 mg |
| Croscarmellose Sodium | 15 mg |
| Silicon Dioxide | 6 mg |
| Magnesium Stearate | 0.5 mg |
| Example #2 | |
| Glucosamine HCl | 750 mg |
| Dicalcium phosphate | 269.9 mg |
| Ginger Root Extract | 180 mg |
| Microcrystalline Cellulose | 56 mg |
| Bromelain | 50 mg |
| Green Tea Extract Powder | 50 mg |
| Stearic Acid | 20 mg |
| Acacia powder | 17.6 mg |
| Sodium starch glycolate | 15 mg |
| Silicon Dioxide | 6 mg |
| Calcium Stearate | 0.5 mg |
| Example #3 | |
| Glucosamine Sulfate | 510 mg |
| Calcium Carbonate | 269.9 mg |
| Ginger Root Extract | 100 mg |
| Microcrystalline Cellulose | 56 mg |
| Bromelain | 75 mg |
| Green Tea Extract | 75 mg |

In some cases, a dietary supplement of a Supplement Formulation M can include 1500 mg of glucosamine HCl, 250 mg of chondroitin sulfate, 500 mg of methylsulfonylmethane (MSM), a 50 mg of a blend of bromelain and papain, and a component comprising the formula of a Supplement Formulation C as described herein. For example, the formula can include turmeric, ginger root extract, green tea extract, aronia (chokeberry) powder, *angelica gigas* root (decursinol), and Devil's claw extract in the above disclosed amounts.

In some cases, a dietary supplement of a Supplement Formulation M can be made and used as described in U.S. Pat. Nos. 6,713,096 or 7,138,149, each of which is herein incorporated by reference in its entirety. For example, a dietary supplement of a Supplement Formulation M can be made to have the ingredients as set forth in U.S. Pat. Nos. 6,713,096 or 7,138,149.

Supplement Formulation N

Supplement Formulation N can include a green coffee bean extract, a green tea phytosome, a green tea extract, Capsimax (encapsulated capsaicinoids), a *capsicum* extract, or any combination of two or more thereof.

In some cases, a dietary supplement of a Supplement Formulation N can contain any appropriate amount of a green coffee bean extract. In some cases, a dietary supplement of a Supplement Formulation N can contain between about 200 mg and about 800 mg (e.g., between about 300 mg and about 500 mg) of a green coffee bean extract. In some cases, a dietary supplement of a Supplement Formulation N can be formulated to contain an amount of green coffee bean extract such that a daily dose of between about 200 mg and about 800 mg (e.g., between about 300 and about 500 mg) of a green coffee bean extract can be conveniently administered.

In some cases, a dietary supplement of a Supplement Formulation N can contain any appropriate amount of a *capsicum* (red pepper) extract containing capsaicinoids, including the capsaicinoid capsaicin. In one preferred embodiment Supplement Formulation N can contain from about 0.1 about 5 mg capsaicin, more preferably from about 1 mg to about 3 mg capsaicin, still more preferable about 2 mg capsaicin.

In some cases, a dietary supplement of a Supplement Formulation N can contain any appropriate amount of a *capsicum* extract having 1% capsaicinoids. In such cases, a dietary supplement of a Supplement Formulation N can contain between about 50 mg and about 500 mg (e.g., between about 150 mg and about 250 mg) of *capsicum* extract. In some cases, a dietary supplement of a Supplement Formulation N can be formulated to contain an amount of a *capsicum* extract such that a daily dose of between about 50 mg and about 500 mg (e.g., between about 150 mg and about 250 mg) of a *capsicum* extract can be conveniently administered.

In another embodiment a *capsicum* extract is provided as an encapsulated capsaicinoid component having 2% capsaicinoids. In some cases, a dietary supplement of a Supplement Formulation N can contain between about 30 mg and about 200 mg (e.g., between about 80 mg and about 120 mg) of encapsulated capsaicinoids having 2% capsaicinoids. In some cases, a dietary supplement of a Supplement Formulation N can be formulated to contain an amount of encapsulated capsaicinoids having 2% capsaicinoids such that a daily dose of between about 30 mg and about 200 mg (e.g., between about 80 mg and about 120 mg) of encapsulated capsaicinoids can be conveniently administered.

In some cases, a dietary supplement of a Supplement Formulation N can contain any appropriate amount of a red pepper extract. In such cases, a dietary supplement of a Supplement Formulation N can contain between about 50 mg and about 500 mg (e.g., between about 150 mg and about 250 mg) of red pepper extract. In some cases, a dietary supplement of a Supplement Formulation N can be formulated to contain an amount of a red pepper extract such that a daily dose of between about 50 mg and about 500 mg (e.g., between about 150 mg and about 250 mg) of a red pepper extract can be conveniently administered.

In one example, a daily dose serving of a dietary supplement of Supplement Formulation N can include:

| | Daily dose (mg/day) | Range (mg/day) |
|---|---|---|
| green coffee bean extract | 400 mg/day | 200-800 |
| green tea phytosome (encapsulated) | 300 | 100-600 |
| encapsulated capsaicin (2% capsaicinoids) | 100 | 30-200 |

In another example, a daily dose serving of a dietary supplement can include:

|  | Daily dose (mg/day) | Range (mg/day) |
|---|---|---|
| green coffee bean extract | 400 mg/day | 200-800 |
| green tea phytosome (encapsulated) | 300 | 100-600 |
| red pepper extract (1% capsaicinoids) | 200 | 50-500 |

In another example, a daily dose of a dietary supplement can include:

|  | Daily dose (mg/day) | Range (mg/day) |
|---|---|---|
| green coffee bean extract | 400 mg/day | 200-800 |
| green tea extract | 1100 | 500-2000 |
| red pepper extract (1% capsaicinoids) | 200 | 50-500 |

Dietary Supplement Formulations

The dietary supplements provided herein can be formulated for oral administration and can include suitable excipients, flavorings, colorants, and other ingredients. For oral administration, tablets or capsules can be prepared with pharmaceutically acceptable excipients such as binding agents, fillers, lubricants, disintegrants, or wetting agents. Liquid preparations for oral administration can take the form of, for example, solutions, syrups, or suspension, or they can be presented as a dry product for constitution with saline or other suitable liquid vehicle before use. In some cases, liquid preparations can contain pharmaceutically acceptable additives such as suspending agents, emulsifying agents, non-aqueous vehicles, preservatives, buffer salts, flavoring agents, coloring agents, and sweetening agents as appropriate. Preparations for oral administration can be suitably formulated to give controlled release of one or more compounds. Typically, a dietary supplement provided herein is in the form of a capsule or tablet form with a fast disintegration time or with a delayed release.

In some cases, the dietary supplements provided herein can contain a pharmaceutically acceptable carrier for administration to a mammal, including, without limitation, sterile aqueous, or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Pharmaceutically acceptable carriers also can include physiologically acceptable aqueous vehicles (e.g., physiological saline) or other carriers appropriate for oral administration.

In some cases, the dietary supplements provided herein can be in the form of a capsule or tablet configured to have a unit dosage equal to the daily desired dosage for a particular mammal. For example, if a mammal desires 100 mg of a particular agent, each tablet or capsule can include about 100 mg in weight of that agent. As used herein, mammals generally refer to humans, but also can include domesticated mammals (e.g., dogs, cats, and livestock such as cows, horses, pigs, or sheep). The dosages of a particular dietary supplement provided herein will depend on many factors including the general health of a mammal. In some cases, a total daily dose may be prepared and administered in the form of one or more dosage forms (e.g., two tablets or capsules, three tablets or capsules, four tablets or capsules, five tablets or capsules, or six tablets or capsules).

In some cases, the dietary supplements provided herein can contain one or more additional additives including, but not limited to, gelatin, glycerin, water, beeswax, lecithin, cocoa, caramel, titanium dioxide, or carmine.

In some cases, the dietary supplements provided herein can be in the form of a softgel. Softgels are predominantly used to contain liquids containing one or more active ingredients in a dissolved or suspended state. Use of softgel formulations can enhanced bioavailability of one or more active ingredients resulting from the fact that the agent is already in solution at the site of absorption, thereby permitting faster and more uniform absorption to occur. Softgels can be provided with suitable coatings that typically contain gelatin and/or suitable edible dye(s). In some cases, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses. In some cases, flavoring may be added to the softgel coat to enhance the taste.

In some cases, the dietary supplements provided herein can be in the form of a capsule or tablet that is provided in a size acceptable for a human consumer to swallow. For example, capsules can be in the range from about 250 mg to 3 g in size, or any size therebetween (e.g., 275 mg, 300 mg, 350 mg, 400 mg, 450 mg, 475 mg, 490 mg, 500 mg, 550 mg, 575 mg, 600 mg, 650 mg, 675 mg, 700 mg, 750 mg, 800 mg, 900 mg, 1000 mg, 1250 mg, 1500 mg, 1750 mg, 1800 mg, 1900 mg, 2 g, 2.1 g, 2.2 g, 2.3 g, 2.4 g, 2.5 g, 2.6 g, 2.7 g, 2.8 g, or 2.9 g).

In some cases, the dietary supplements provided herein can be provided in the form of a gel cap, soft gelatin capsule (e.g., soft gel capsule), or hard gelatin capsule. For example, a dietary supplement provided herein can be encapsulated by a hard gel capsule. For oral administration, soft gel capsules can be prepared by conventional means with pharmaceutically acceptable excipients such as binding agents, fillers, lubricants, disintegrants, or wetting agents. Soft gel capsule manufacturing methods are described in, e.g., U.S. Pat. No. 6,333,047. In some cases, a dietary supplement provided herein can be formulated as capsules that can demonstrate improved shelf life, homogeneity, and product stability.

Multi-Supplement Compositions

A multi-supplement composition provided herein can include three or more different dietary supplement formulations within a single packaging unit. For example, a single packaging unit can include at least three different dietary supplement formulations (e.g., three, four, five, six, seven, eight, nine, ten, eleven, twelve, or more different dietary supplement formulations) selected from the group of one or more dietary supplements of a Supplement Formulation A, one or more dietary supplements of a Supplement Formulation B, one or more dietary supplements of a Supplement Formulation C, one or more dietary supplements of a Supplement Formulation D, one or more dietary supplements of a Supplement Formulation E, one or more dietary supplements of a Supplement Formulation F, one or more dietary supplements of a Supplement Formulation G, one or more dietary supplements of a Supplement Formulation H, one or more dietary supplements of a Supplement Formulation I, one or more dietary supplements of a Supplement Formulation J, one or more dietary supplements of a Supplement Formulation K, one or more dietary supplements of a Supplement Formulation L, and one or more dietary supplements of a Supplement Formulation M.

In some cases, a single packaging unit can include a dietary supplement of a dietary supplement of a Supplement Formulation A, a dietary supplement of a Supplement Formulation B, and a dietary supplement of a Supplement Formulation C; a dietary supplement of a dietary supplement of a Supplement Formulation A, a dietary supplement of a Supplement Formulation B, and a dietary supplement of a Supplement Formulation D; a dietary supplement of a dietary supplement of a Supplement Formulation A, a dietary supplement of a Supplement Formulation B, and a dietary supplement of a Supplement Formulation E; a dietary supplement of a dietary supplement of a Supplement Formulation A, a dietary supplement of a Supplement Formulation B, and a dietary supplement of a Supplement Formulation F; a dietary supplement of a dietary supplement of a Supplement Formulation A, a dietary supplement of a Supplement Formulation C, and a dietary supplement of a Supplement Formulation D; a dietary supplement of a dietary supplement of a Supplement Formulation A, a dietary supplement of a Supplement Formulation C, and a dietary supplement of a Supplement Formulation E; a dietary supplement of a dietary supplement of a Supplement Formulation A, a dietary supplement of a Supplement Formulation C, and a dietary supplement of a Supplement Formulation F; a dietary supplement of a dietary supplement of a Supplement Formulation B, a dietary supplement of a Supplement Formulation C, and a dietary supplement of a Supplement Formulation D; a dietary supplement of a dietary supplement of a Supplement Formulation B, a dietary supplement of a Supplement Formulation C, and a dietary supplement of a Supplement Formulation E; a dietary supplement of a dietary supplement of a Supplement Formulation B, a dietary supplement of a Supplement Formulation C, and a dietary supplement of a Supplement Formulation F; a dietary supplement of a dietary supplement of a Supplement Formulation C, a dietary supplement of a Supplement Formulation D, and a dietary supplement of a Supplement Formulation E; a dietary supplement of a dietary supplement of a Supplement Formulation C, a dietary supplement of a Supplement Formulation D, and a dietary supplement of a Supplement Formulation F; a dietary supplement of a Supplement Formulation A, a dietary supplement of a Supplement Formulation B, a dietary supplement of a Supplement Formulation C, and a dietary supplement of a Supplement Formulation D; a dietary supplement of a Supplement Formulation A, a dietary supplement of a Supplement Formulation B, a dietary supplement of a Supplement Formulation C, and a dietary supplement of a Supplement Formulation E; a dietary supplement of a Supplement Formulation A, a dietary supplement of a Supplement Formulation B, a dietary supplement of a Supplement Formulation C, and a dietary supplement of a Supplement Formulation F; a dietary supplement of a Supplement Formulation A, a dietary supplement of a Supplement Formulation C, a dietary supplement of a Supplement Formulation D, and a dietary supplement of a Supplement Formulation E; a dietary supplement of a Supplement Formulation A, a dietary supplement of a Supplement Formulation C, a dietary supplement of a Supplement Formulation D, and a dietary supplement of a Supplement Formulation F; a dietary supplement of a Supplement Formulation A, a dietary supplement of a Supplement Formulation D, a dietary supplement of a Supplement Formulation E, and a dietary supplement of a Supplement Formulation F; a dietary supplement of a Supplement Formulation B, a dietary supplement of a Supplement Formulation C, a dietary supplement of a Supplement Formulation D, and a dietary supplement of a Supplement Formulation E; a dietary supplement of a Supplement Formulation B, a dietary supplement of a Supplement Formulation C, a dietary supplement of a Supplement Formulation D, and a dietary supplement of a Supplement Formulation F; a dietary supplement of a Supplement Formulation A, a dietary supplement of a Supplement Formulation B, a dietary supplement of a Supplement Formulation C, a dietary supplement of a Supplement Formulation D, and a dietary supplement of a Supplement Formulation E; a dietary supplement of a Supplement Formulation A, a dietary supplement of a Supplement Formulation B, a dietary supplement of a Supplement Formulation C, a dietary supplement of a Supplement Formulation D, and a dietary supplement of a Supplement Formulation F; or a dietary supplement of a Supplement Formulation B, a dietary supplement of a Supplement Formulation C, a dietary supplement of a Supplement Formulation D, a dietary supplement of a Supplement Formulation E, and a dietary supplement of a Supplement Formulation F.

In some cases, a single packaging unit can include a dietary supplement of a Supplement Formulation A, a dietary supplement of a Supplement Formulation B, a dietary supplement of a Supplement Formulation C, a dietary supplement of a Supplement Formulation E, and a dietary supplement of a Supplement Formulation F.

For example, in one embodiment, a single packaging unit can include one or more dietary supplements of a Supplement Formulation A, one or more dietary supplements of a Supplement Formulation B, one or more dietary supplements of a Supplement Formulation C, one or more dietary supplements of a Supplement Formulation D, one or more dietary supplements of a Supplement Formulation E, and one or more dietary supplements of a Supplement Formulation F.

In another example, a single packaging unit can include one or more dietary supplements of a Supplement Formulation A, one or more dietary supplements of a Supplement Formulation B, one or more dietary supplements of a Supplement Formulation C, one or more dietary supplements of a Supplement Formulation D, one or more dietary supplements of a Supplement Formulation E, one or more dietary supplements of a Supplement Formulation F, one or more dietary supplements of a Supplement Formulation G, and one or more dietary supplements of a Supplement Formulation H.

In another example, a single packaging unit can include one or more dietary supplements of a Supplement Formulation E, one or more dietary supplements of a Supplement Formulation I, one or more dietary supplements of a Supplement Formulation J, and one or more dietary supplements of a Supplement Formulation K.

In another example, a single packaging unit can include one or more dietary supplements of a Supplement Formulation A, one or more dietary supplements of a Supplement Formulation B, one or more dietary supplements of a Supplement Formulation C, one or more dietary supplements of a Supplement Formulation D, one or more dietary supplements of a Supplement Formulation E, one or more dietary supplements of a Supplement Formulation F, one or more dietary supplements of a Supplement Formulation I, one or more dietary supplements of a Supplement Formulation J, and one or more dietary supplements of a Supplement Formulation K.

In another example, a single packaging unit can include one or more dietary supplements of a Supplement Formulation A, one or more dietary supplements of a Supplement Formulation B, one or more dietary supplements of a Supplement Formulation C, one or more dietary supplements of a Supplement Formulation D, one or more dietary supplements of a Supplement Formulation E, one or more dietary supplements of a Supplement Formulation F, one or more dietary supplements of a Supplement Formulation I, and one or more dietary supplements of a Supplement Formulation L.

The invention will be further described in the following examples, which do not limit the scope of the invention described in the claims.

EXAMPLES

Example 1a

An Exemplary Dietary Supplement of Supplement Formulation H

Phosphatidylserine, DHA, EPA, antioxidants, and *Ginkgo biloba* were used to create a mixture. The mixture was blended and encapsulated in soft gelatin capsule form to provide a dietary composition containing 12% by weight phosphatidylserine, 7% by weight DHA, 7% by weight EPA, 2.8% by weight antioxidants, and 4.7% by weight *Ginkgo biloba*.

Example 1b

An Exemplary Dietary Supplement of Supplement Formulation H

Phosphatidylserine, DHA, EPA, antioxidants, and *Ginkgo biloba* were used to create a mixture. The mixture was blended and incorporated into a consumable chocolate form to provide a dietary composition containing 12% by weight phosphatidylserine, 7% by weight DHA, 7% by weight EPA, 2.8% by weight antioxidants, and 4.7% by weight *Ginkgo biloba*. The blend was incorporated into a chocolate base to create a chocolate bar (molded) that contains one serving of described mixture. This product can be consumed as one serving, for example, in lieu of one serving of a capsule, gelcap, or tablet of product.

Example 1c

An Exemplary Dietary Supplement of Supplement Formulation H

Phosphatidylserine, DHA, EPA, antioxidants, and *Ginkgo biloba* were used to create a mixture. The mixture was blended and encapsulated in soft gelatin capsules form to provide a dietary composition containing 3.5% by weight phosphatidylserine, 11.7% by weight DHA, 10.5% by weight EPA, 4.7% by weight antioxidants, and 2.9% by weight *Ginkgo biloba*.

Example 1d

An Exemplary Dietary Supplement of Supplement Formulation H

Phosphatidylserine, DHA, EPA, antioxidants, and *Ginkgo biloba* were used to create a mixture. The mixture was blended and incorporated into a consumable chocolate form to provide a dietary composition containing 3.5% by weight phosphatidylserine, 11.7% by weight DHA, 10.5% by weight EPA, 4.7% by weight antioxidants, and 2.9% by weight *Ginkgo biloba*.

Example 2a

An Exemplary Dietary Supplement of Supplement Formulation K

A soft gel capsule containing:

| Ingredients | Amount, mg |
| --- | --- |
| Phytosterol Esters (>90%; Cognis) | 567 |
| 30% Fish oil (EPA:DHA 1.5:1 (18%:12%)) | 433 |
| Lecithin | 5 |
| CoQ-10 | 5 |
| Bromelain | 10 |

Serving recommendation is 3 capsules per day.

Example 2b

An Exemplary Dietary Supplement of Supplement Formulation K

A soft gel capsule containing:

| Ingredients | Amount, mg |
| --- | --- |
| Phytosterol Esters (>94%, Cognis) | 425 |
| EPA | 88 |
| DHA | 58 |
| Polysorbate 20 | 10 |

Serving recommendation is 4 capsules per day.

Example 2c

An Exemplary Dietary Supplement of Supplement Formulation K

A soft gel capsules containing:

| Ingredients | Amount, mg |
| --- | --- |
| Phytosterol Esters (>94%, Cognis) | 567 |
| EPA | 117 |
| DHA | 77 |

Serving recommendation is 3 capsules per day.

Example 2d

An Exemplary Dietary Supplement of Supplement Formulation K

A soft gel capsule containing:

| Ingredients | Amount, mg |
| --- | --- |
| Phytosterol Esters (>94%, Cognis) | 567 |
| EPA | 117 |
| DHA | 77 |
| Acyl-lactylate | 10 |
| bromelain | 10 |

Serving recommendation is 3 capsules per day.

Example 2e

An Exemplary Dietary Supplement of Supplement Formulation K

A hard shell gel capsule containing:

| Ingredients | Amount, mg |
| --- | --- |
| Phytosterols (>90%, Cognis) | 400 |
| Fish oil powder (EPA:DHA 1.5:1) | 350 |
| Polysorbate 20 | 5 |
| CoQ-10 | 5 |
| Bromelain | 10 |

Serving recommendation is 3 capsules per day.

Example 2f

An Exemplary Dietary Supplement of Supplement Formulation K

A hard shell gel capsule containing:

| Ingredients | Amount, mg |
| --- | --- |
| Phytosterols (>90%) | 400 |
| Fish oil powder (EPA:DHA 1.5:1) | 350 |
| Lecithin | 5 |
| Tocotrienol | 7 |
| Bromelain | 8 |

Serving recommendation is 3-4 capsules per day.

Example 2g

An Exemplary Dietary Supplement of Supplement Formulation K

A hard shell gel capsule containing:

| Ingredients | Amount, mg |
| --- | --- |
| Phytosterols (>90%) | 400 |
| Fish oil powder (EPA:DHA 1.5:1) | 350 |
| Lecithin | 5 |
| CoQ-10 | 5 |

Serving recommendation is 3 capsules per day.

Example 2h

An Exemplary Dietary Supplement of Supplement Formulation K

A soft gel capsule containing:

| Ingredients | Amount, mg |
| --- | --- |
| Phytosterol Esters (>94% phytostanol esters) | 567 |
| EPA | 60 |
| DHA | 40 |
| Polysorbate 80 | 5 |
| Bromelain | 5 |

Serving recommendation is 3 capsules per day.

Example 2i

An Exemplary Dietary Supplement of Supplement Formulation K

A soft gel capsule containing:

| Ingredients | Amount, mg |
| --- | --- |
| Phytostanol Esters (>92%) | 567 |
| EPA | 60 |
| DHA | 40 |
| Polysorbate 20 | 5 |
| Bromelain | 10 |

Serving recommendation is 3 capsules per day.

Example 2j

An Exemplary Dietary Supplement of Supplement Formulation K

A soft gel capsule containing the following was made:

| Ingredients | Amount, mg |
| --- | --- |
| Phytosterol Esters (>90%) | 375 |
| Fish oil (30%; EPA:DHA 18%:12%) | 275 |
| Bromelain | 13 |
| Lecithin | 15 |
| Ubiquinone Q-10 | 5 |
| Triethyl citrate | 5 |
| Sorbitan oleate | 10 |

Serving recommendation is 4 capsules per day.

Example 2k

An Exemplary Dietary Supplement of Supplement Formulation K

A soft gel capsule containing the following was made:

| Ingredients | Amount, mg |
|---|---|
| Phytosterol Esters (>90%) | 375 |
| Fish oil (30%, EPA:DHA 18%:12%)) | 275 |
| Bromelain | 13 |
| Lecithin | 15 |
| Triethyl citrate | 5 |
| Sorbitan oleate | 10 |

Serving recommendation is 4 capsules per day.

Example 2l

An Exemplary Dietary Supplement of Supplement Formulation K

A soft gel capsule containing:

| Ingredients | Amount, mg |
|---|---|
| Phytosterol Esters (>90%) | 375 |
| Fish oil (30%, EPA:DHA 18%:12%) | 275 |
| Bromelain | 13 |
| Lecithin | 15 |
| Ubiquinone Q-10 | 5 |
| Triethyl citrate | 5 |
| Sorbitan oleate | 10 |
| Lemon oil | 6 |

Serving recommendation is 4 capsules per day.

Example 2m

An Exemplary Dietary Supplement of Supplement Formulation K

A nutritional supplement containing:

| Serving Size: 3-4 capsules | | | |
|---|---|---|---|
| Ingredient | Specs | Amount Per Serving | % Daily Value* |
| Phytosterol esters | >94% | 1.7 g | ** |
| Omega-3 Fatty Acid (triglyceride form) | | 300 mg | ** |
| EPA | | 180 mg | ** |
| DHA | | 120 mg | ** |
| Bromelain | | 50 mg | ** |
| Lecithin | | 15 mg | |
| CoQ-10 | | 10 mg | ** |

*Percent Daily Value is based on a 2000 calorie diet (US RDA).
**Daily Value not established.

Example 2n

An Exemplary Dietary Supplement of Supplement Formulation K

A nutritional supplement containing:

| Serving Size: 3-4 Capsules | | | |
|---|---|---|---|
| | Specs | Amount Per Serving | % Daily Value* |
| Phytosterol esters | >94% | 1.7 g | ** |
| Omega-3 Fatty Acid (triglycerides form) | | 300 mg | ** |
| EPA | | 180 mg | ** |
| DHA | | 120 mg | ** |
| Bromelain | | 50 mg | ** |
| Polysorbate -20 | | 10 mg | |

*Percent Daily Value is based on a 2000 calorie diet (US RDI).
**Daily Value not established.

Example 2o

An Exemplary Dietary Supplement of Supplement Formulation K

A nutritional supplement containing:

| Serving Size: 3-4 capsules | | | |
|---|---|---|---|
| | Specs | Amount Per Serving | % Daily Value* |
| Phytosterol esters | >94% | 1.7 g | ** |
| Omega-3 Fatty Acid (triglycerides form) | | 300 mg | ** |
| EPA | | 180 mg | ** |
| DHA | | 120 mg | ** |
| Lecithin | | 25 mg | |

*Percent Daily Value is based on a 2000 calorie diet (US RDA).
**Daily Value not established.

Example 2p

An Exemplary Dietary Supplement of Supplement Formulation K

A nutritional supplement containing the following was made:

| Serving Size: 3-4 capsules | | | |
|---|---|---|---|
| | Specs | Amount Per Serving | % Daily Value* |
| Phytosterol esters | >94% | 1.7 g | ** |
| Omega-3 Fatty Acid (triglycerides form) | | 300 mg | ** |
| EPA | | 180 mg | ** |
| DHA | | 120 mg | ** |
| Bromelain | | 50 mg | ** |
| Sorbitan oleate | | 40 mg | |
| Triethyl Citrate | | 20 mg | |
| CoQ-10 | | 5 mg | ** |

*Percent Daily Value is based on a 2000 calorie diet (US RDA).
**Daily Value not established.

Example 2q

An Exemplary Dietary Supplement of Supplement Formulation K

A nutritional supplement containing:

| Serving Size: 3-4 capsules | | | |
|---|---|---|---|
| | Specs | Amount Per Serving | % Daily Value* |
| Phytosterol esters | >94% | 1.7 g | ** |
| Omega-3 Fatty Acid (triglycerides form) | | 300 mg | ** |
| EPA | | 180 mg | ** |
| DHA | | 120 mg | ** |

*Percent Daily Value is based on a 2000 calorie diet (US RDA).
**Daily Value not established.

Example 2r

An Exemplary Dietary Supplement of Supplement Formulation K

The following procedure was used to encapsulate soft gel caps. The capsule ingredients were weighed and compounded by shearing in a vacuum mixture until homogeneous. The mixture was cooled to 31-34° C. A gelatin mixture (containing gelatin, colorant, glycerin, and water) was then heated, sheared and kept under vacuum in the vacuum mixer until any foam subsided. The gelatin mixture was held at >34° C. A Kamata or Bo Cheng encapsulator was used, with die roll size 18 oval (or oblong), segment size 14 oval (or oblong). The mix and gelatin mix were charged into the batch. The capsules were sampled and inspected. Capsules were dried on trays to a final moisture content of 5-10%.

Example 3a

Stability of Bacterial Compositions of Supplement Formulation A

Two bacterial compositions were produced (Prototype trial 1 and Prototype trial 2) as follows. The final formulations were stored in various bottles as described below:
(i) MCC 101 and MCC 112 were used as diluent in prototype trials.
(ii) PET bottle, HDPE bottle, and sealed Aluminum foil packet were used in storing the final capsule.

Prototype Trial 1:

| Component | Potency of raw ingredients (billion CFU/g) | % of ingredients | Final Potency (Billion CFU/g) |
|---|---|---|---|
| Lactobacillus acidophilus | 200 | 7.58 | 15.00 |
| Bifidobacterium lactis | 450 | 2.07 | 9.00 |
| Fructooligosaccharides | | 3.70 | |
| Dicalcium Phosphate | | 1.85 | |
| MCC 101 | | 81.90 | |
| Calcium Stearate | | 1.40 | |
| Silicon Dioxide | | 1.48 | |
| Total | | 100.0% | 24 |

270 mg of above blend was filled into a single capsule.

Potency of 270 mg of blend=24/1000*270=6.48 billion CFUs/capsule

Prototype Trial 2:

| Component | Potency of raw ingredients (billion CFU/g) | % of ingredients | Final Potency (Billion CFU/g) |
|---|---|---|---|
| Lactobacillus acidophilus | 200 | 7.58 | 15.00 |
| Bifidobacterium lactis | 450 | 2.07 | 9.00 |
| Fructooligosaccharides | | 3.70 | |
| MCC 112 | | 83.75 | |
| Calcium Stearate | | 1.40 | |
| Silicon Dioxide | | 1.48 | |
| Total | | 100.0% | 24 |

270 mg of above blend was filled into a single capsule.

Potency of 270 mg of blend=24/1000*270=6.48 billion CFUs/capsule

Prototype trial 3 is made as follows:

| Component | Potency of raw ingredients (billion CFUs/g) | % of ingredients | Final Potency (Billion CFU/g) |
|---|---|---|---|
| Lactobacillus acidophilus | 200 | 7.58 | 15.00 |
| Bifidobacterium lactis | 450 | 2.07 | 9.00 |
| Fructooligosaccharides | | 3.70 | |
| Dicalcium Phosphate | | 1.85 | |
| MCC 112 | | 81.90 | |
| Calcium Stearate | | 1.40 | |
| Silicon Dioxide | | 1.48 | |
| Total | | 100.0% | 24 |

270 mg of above blend is used to fill a single capsule.

Potency of 270 mg of blend=24/1000*270=6.48 billion CFUs/capsule

Once produced, the two bacterial compositions were tested for stability and observed with the following probiotics count (CFUs/capsule) and water activity:

| | Formulation filler | | | | | | | |
|---|---|---|---|---|---|---|---|---|
| | MCC 101 | | MCC 112 | | MCC 112 | | MCC 112 | |
| | Packaging type | | | | | | | |
| | PET (Polyethylene terephthalate) bottle | | PET bottle | | High Density Polyethylene (HDPE) bottle | | Aluminum foil packet | |
| | CFU/capsule | $A_w$ | CFU/capsule | $A_w$ | CFU/capsule | $A_w$ | CFU/capsule | $A_w$ |
| Initial | 7.3 billion | NA | 5.4 billion | 0.165 | 5.0 billion | 0.130 | 5.8 billion | 0.130 |
| after 3 months at 25° C./60 relative humidity | NA | NA | 8.4 billion | 0.169 | 8.4 billion | 0.133 | 8.1 billion | 0.141 |
| after 3 months at 30° C./75 relative humidity | 0.0016 billion | NA | 2.9 billion | 0.171 | 8.7 billion | 0.125 | 7.8 billion | 0.141 |

These results demonstrate that, using microcrystalline cellulose in bacterial compositions having at least two strains, MCC 112 improved stability over MCC 101 and that using a High Density Polyethylene (HDPE) bottle or Aluminum foil packet improved stability over using a PET bottle.

Example 3b

Stability of Bacterial Compositions of Supplement Formulation A

A bacterial composition was produced as follows:

| Component | Potency of strain | % of ingredients, by weight | Final Potency in Billion CFU |
|---|---|---|---|
| Lactobacillus acidophilus | 200 | 3.75 | 7.5 |
| Lactobacillus plantarum | 400 | 2.5 | 10 |
| Lactobacillus casei | 300 | 2.5 | 7.5 |
| Lactobacillus rhamnosus | 200 | 4.0 | 8.0 |
| Bifidobacterium longum | 100 | 4.0 | 4.0 |
| Bifidobacterium lactis | 450 | 2.0 | 9.0 |
| Bifidobacterium bifidum | 100 | 4.0 | 4.0 |
| Fructooligosaccharides | | 5.0 | |
| MCC 112 | | 70.25 | |
| Magnesium Stearate (Palmstar MGST 325) | | 1.50 | |
| Silicon Dioxide (Syloid 244) | | 0.50 | |
| Total | | 100.0% | 50 |

400 mg of the above blend was filled into a single DR capsule. The potency of the 400 mg of blend was 20 billion CFUs/capsule.

Once produced, the bacterial composition was tested for stability and observed with the following probiotics count (CFUs/capsule) and water activity:

| | |
|---|---|
| Formulation filler | MCC 112 |
| Bottle type | HDPE |
| Initial CFUs/capsule | 12.7 billion |
| Initial water activity ($A_w$) | 0.139 |
| CFUs/capsule after 3 months at 25° C./60 relative humidity | 14.0 billion |
| Water activity ($A_w$) after 3 months at 25° C./60 relative humidity | 0.133 |

These results confirm that using microcrystalline cellulose MCC 112 and a High Density Polyethylene (HDPE) bottle maintained stability in a bacterial composition having seven strains of bacteria.

Example 3c

Bacterial Composition of Supplement Formulation A

A bacterial composition was prepared as follows (in the Table shown below titled "Bacterial Composition Example"). Briefly, lyophilized bacteria of varying CFUs of each of Lactobacillus acidophilus, Lactobacillus plantarum, Lactobacillus casei, Lactobacillus rhamnosus, Bifidobacterium longum, Bifidobacterium lactis, and Bifidobacterium bifidum, and further including silicon dioxide (silica; 2 mg) were blended for two minutes to coat the dried bacteria uniformly. Without being bound by any theory, it is believed that the silica adsorb excess moisture, keeping the lyophilized bacteria dry with minimal water activity and improving the stability of final formulation. MCC 112 (grade of microcrystalline cellulose with $A_w$ of less than 0.2 (700 mg), and fructooligosaccharides (50 mg) were then added, and the mixture was blended for an additional 20 minutes. After blending, additional silica (3 mg) as a glidant and magnesium stearate (15 mg) as lubricant, were added, and the mixture was blended for another three minutes. The final mixture was inserted into capsules (e.g., DR capsules). DR capsules are vegetarian capsules made with a hypromellose (HPMC) formulation that can help protect sensitive ingredients from the low pH environment of the stomach. By protecting against early disintegration, disintegration generally starts approximately 45 minutes later than a typical immediate release capsule of about 5 minutes, and the ingredients are released in the intestine at an alkaline pH.

Bacterial Composition Example

| Component | raw ingr. level (billion CFUs/g) | example formula 1 % of ingr., by weight | example formula 1 finished product (billion CFUs/g) | example formula 2 % of ingr., by weight | example formula 2 finished product (billion CFUs/g) | example formula 3 % of ingr., by weight | example formula 3 finished product (billion CFUs/g) | example formula 4 % of ingr., by weight | example formula 4 finished product (billion CFUs/g) | example formula 5 % of ingr., by weight | example formula 5 finished product (billion CFUs/g) |
|---|---|---|---|---|---|---|---|---|---|---|---|
| *Lactobacillus acidophilus* | 200 | 3.75% | 7.5 | 3.75% | 7.5 | 3.75% | 7.5 | 7.50% | 15.0 | 7.50% | 15 |
| *Lactobacillus plantarum* | 400 | 2.50% | 10 | 2.50% | 10 | 2.50% | 10 | 1.00% | 4.0 | 2.00% | 8 |
| *Lactobacillus casei* | 300 | 2.50% | 7.5 | 2.50% | 7.5 | 2.50% | 7.5 | 1.80% | 5.40 | 0.90% | 2.7 |
| *Lactobacillus rhamnosus* | 200 | 4.00% | 8 | 4.00% | 8 | 4.00% | 8 | 0.90% | 1.80 | 0.90% | 1.8 |
| *Bifidobacterium longum* | 100 | 4.00% | 4 | 4.00% | 4 | 4.00% | 4 | 1.00% | 1.00 | 0.10% | 0.1 |
| *Bifidobacterium lactis* | 450 | 2.00% | 9 | 2.00% | 9 | 2.00% | 9 | 15.00% | 67.5 | 7.50% | 33.75 |
| *Bifidobacterium bifidum* | 100 | 4.00% | 4 | 4.00% | 4 | 4.00% | 4 | 0.20% | 0.20 | 0.10% | 0.1 |
| Fructooligo-saccharides | | 5.00% | | 5.00% | | 5.00% | | 5.00% | | 5.00% | |
| MCC 112 | | 70.25% | | | | | | | | | |
| MCC 101 | | | | | | 30 | | 65.6 | | | |
| MCC 302 | | | | | | | | | | 74% | |
| Rice Maltodextrin | | | | 70.25 | | 40.25 | | | | | |
| Magnesium Stearate (Palmstar MGST 325) | | 1.50% | | 1.00% | | 0.75% | | 1.5% | | | |
| Calcium Stearate | | | | 0.25 | | 0.5 | | | | 1.50% | |
| colloidal silicon dioxide (AEROSIL ® R 972 Pharma) | | | | | | | | 0.25% | | | |
| Silicon Dioxide (Syloid 244) | | 0.50% | | 0.75% | | 0.75% | | 0.25 | | 0.50% | |
| Total | | 100% | 50 | | | | | 100.0 | 94.9 | 100% | 61.45 |

Ingr. = ingredient

Example 4a

An Exemplary Dietary Supplement Composition of Supplement Formulation G

A dietary supplement was prepared with the composition shown below.

| | |
|---|---|
| Huperzine A | 50 μg |
| Acetyl L-Carnitine HCl | 600 mg |
| Bacopa monniera | 300 mg |
| Vitamin E | 200 IU |
| Vitamin B12 | 1000 μg |
| Folic Acid | 800 μg |
| Curcumin | 100 mg |

Example 4b

An Exemplary Dietary Supplement Composition of Supplement Formulation G

A dietary supplement can be prepared with the composition shown below.

| | |
|---|---|
| Huperzine A | 0.3 mg |
| Acetyl L-Carnitine HCl | 1000 mg |
| Bacopa monniera | 400 mg |
| Vitamin E | 500 IU |
| Vitamin B12 | 2000 μg |
| Vitamin B6 | 10 mg |
| Curcumin | 400 mg |

Example 4c

An Exemplary Dietary Supplement Composition of Supplement Formulation G

A dietary supplement can be prepared with the composition shown below.

| | |
|---|---|
| Huperzine A | 0.02 mg |
| Acetyl L-Carnitine HCl | 1500 mg |
| Bacopa monniera | 250 mg |
| Vitamin E | 100 IU |
| Vitamin B6 | 5 mg |
| Vitamin B12 | 1500 μg |
| Folic Acid | 900 μg |
| Curcumin | 200 mg |

Example 5a

An Exemplary Multi-Supplement Composition of Dietary Supplement Formulations within a Single Packaging Unit A single package unit of a multi-supplement composition included a dietary supplement of a Supplement Formulation A, a dietary supplement of a Supplement Formulation B, a dietary supplement of a Supplement Formulation C, a dietary supplement of a Supplement Formulation D, a dietary supplement of a Supplement Formulation E, and a dietary supplement of a Supplement Formulation F. Each of the dietary supplements (e.g., a dietary supplement of Supplement Formulation A, a dietary supplement of a Supplement Formulation B, a dietary supplement of a Supplement Formulation C, a dietary supplement of a Supplement Formulation D, a dietary supplement of a Supplement Formulation E, and a dietary supplement of a Supplement Formulation F) were provided in the form of one or more pills. The single package unit, thus, included a foil packet containing the individual pills of each dietary supplement.

Example 5b

Health Assessment Study

Test Subjects

A study was conducted with 48 healthy human subjects of various ages. None of the test subjects were taking any type of medication. However, according to their health markers, 24 of the subjects had slightly elevated blood pressure, cholesterol, or bodyweight that were still within a normal range for humans. The other 24 subjects had healthy markers closer to median values of a normal range for humans.

The test population included 24 healthy individuals (referred to as the "Healthy" test group) and 24 individuals with metabolic syndrome (referred to as the "Metabolic" test group) male and female subjects divided in two subgroups of age 25+/−5 and 50+/−5 years, BMI 20-24 (healthy) and BMI>30 (metabolic syndrome) groups, respectively.

Subjects with metabolic syndrome included male and female subjects, age 25-55 years with the metabolic syndrome according to the ATP III Criteria. (NIH 2002: Waist circumference >102 cm, triglycerides >150 mg/dl, HDL cholesterol <40 mg/dl, BP >130/85 mmHg, fasting blood glucose >100 mg/dl).

Methodology

The methodology of the study consisted of taking blood from each individual subject. Blood samples were tested for free radical activity, cholesterol levels, blood lipid levels, C-reactive protein, glucose levels and insulin response, and inflammation. Heart rate and blood pressure were also recorded.

Measurements were taken before and immediately after a specific prescribed amount of exercise. Subjects were asked to come to the laboratory having fasted for eight hours. The tests went on for a period of 12 weeks. Each subject was asked to not change anything about their lifestyle or diet during those 12 weeks, except to take the multi-supplement composition of Supplement Formulations as disclosed in Example 5a.

The testing method was based upon the monitoring of ESR signal of spin probe oxidation that has been mixed with freshly drawn blood. During the process the blood cells stand under the original physiological environment (t=37° C., pO2=110 mm/Hg) and remain surrounded by blood plasma that releases biologically available reactive oxygen species (ROS) that interacts in intracellular and extracellular space with CMH to form a stable radical CM•. Addition of oxygen sensitive label (NOX-15.1-5 µM) to the blood sample was used to monitor oxygen concentrations and cellular as well as mitochondrial oxygen consumption. A bench-top EPR spectrometer "Noxyscan" was used.

An ex vivo cellular inflammatory response assay was also performed. Application of this assay provided results describing changes in ROS generation by blood cells after stimulation with external (non-endogenous) TNF-α. TNF-α had previously been reported to be a key factor of inflammation. The assay was performed using blood samples from each of the study subjects (20 µL). Samples were not analyzed for changes in TNF-α concentration but rather for changes in downstream effects resulting from exogenous TNF-α challenge. A kinetic curve slope (EPR signal amplitude vs. time) for a 60 minutes analysis was integrated and expressed as formation of ROS µM/min.

Analysis of circulating NO concentration in human blood, second key signaling molecule of vascular physiology and an in vivo antioxidant, was performed.

Health parameters (blood pressure, heart rate, lipid and glucose profile, bioavailability of circulating NO was analyzed on control day, as well as after 6 and 12 weeks of twice daily supplementation. To establish each person's baseline health metrics, extensive testing was conducted separately on each subject prior to taking the supplements. The AM and PM packs of the supplements were then administered along with a small roll of bread in order to aid digestion and to evaluate the body's insulin response.

Measurements were taken again, one hour after the subject first took the supplements. This was done with all 48 subjects. Subjects were asked to take the supplements every day for a period of six weeks and return to the laboratory where tests identical to those administered prior to taking the supplements were repeated.

Subjects were asked to continue taking the supplements for an additional six weeks and then return again to repeat the blood tests.

The reactive oxygen species, inflammatory parameters and nitric oxide levels in this study were measured according to the methods described in one or more of the following references:

Fink B., Dikalov S., Bassenge E. A new approach for extracellular spin trapping of nitroglycerin-induced superoxide radicals both in vitro and in vivo. *Free Radic Biol Med;* 28:121-8; 2000.

Bassenge E., Fink N., Skatchkov M., Fink B. Dietary supplement with vitamin C prevents nitrate tolerance. *J Clin Invest;* 102:67-71; 1998.

Mrakic-Sposta S., Gussoni M., Montorsi M., Porcelli S., Vezzoli A. Assessment of a standardized ROS production profile in humans by electron paramagnetic resonance. *Oxid Med Cell Longev;* 2012:973927; 2012.

Komarov D. A., Dhimitruka I., Kirilyuk I. A., Trofimiov D. G., Grigor'ev I. A., Zweier J. L. et al. Electron paramagnetic resonance monitoring of ischemia-induced myocardial oxygen depletion and acidosis in isolated rat hearts using soluble paramagnetic probes. *Magn Reson Med;* 68:649-55; 2012.

Bobko A. A., Dhimitruka I., Eubank T. D., Marsh C. B., Zweier J. L., Khramtsov V. V. Trityl-based EPR probe with enhanced sensitivity to oxygen. *Free Radic Biol Med;* 47:654-8; 2009.

Feuerstein G. Z., Liu T., Barone F. C. Cytokines, inflammation, and brain injury: role of tumor necrosis factor-alpha. *Cerebrovasc Brain Metab Rev;* 6:341-60; 1994; Dikalov S., Fink B. ESR techniques for the detection of nitric oxide in vivo and in tissues. *Methods Enzymol;* 396:597-610; 2005.

Pisaneschi S., Strigini F. A., Sanchez A. M., Begliuomini S., Casarosa E., Ripoli A. et al. Compensatory feto-placental upregulation of the nitric oxide system during fetal growth restriction. *PLoS One;* 7:e45294; 2012.

Results in One Hour

The subjects' hearts were observed to not have to work as hard to perform exactly the same exercise as they had done prior to taking the supplements. About one hour after using the supplements for the first time, an average reduction of heart rate by five beats per minute after the prescribed exercise was observed. Such a result within one hour after taking the supplements was an unexpected result.

Besides the improvement in heart rate in the first hour, the following observations were also made:

A 10.2% reduction in free radicals during exercise.

A 27.4% significant reduction in blood sugar spike after eating.

Blood Lipid Findings

The study showed significant improvements in total cholesterol, HDL, LDL, and triglyceride levels for the 48 subjects in the study.

Cholesterol

In particular, the following improvements were observed after six weeks of consistent twice-a-day use of the supplements:

The 48 subjects recorded an average 7.5% reduction in total cholesterol in their blood, bringing the average down from the normal but elevated range to within the ideal range.

Those subjects whose cholesterol levels were normal but elevated recorded an even greater reduction of 8.5% in total cholesterol levels. LDL (or bad cholesterol) dropped an average of 6.7% among the 48 subjects.

Subjects who had normal but elevated LDL showed the greatest improvement.

The elevated group recorded an 11.3% drop in LDL cholesterol levels.

Also significant, study participants who had normal but less than ideal HDL cholesterol levels recorded an average 18.3% increase in HDL (or good cholesterol).

The table below provide metabolic markers of the test subject over time.

Blood Pressure Response

In addition, the 48 study subjects recorded an average of a 5.2% reduction in systolic blood pressure after 6 weeks of continued use of the supplements.

Those who began the study with normal but slightly elevated systolic blood pressure recorded a 5.9% reduction.

Effect on Nitric Oxide

To provide further evidence that the supplements can help maintain healthy blood pressure, nitric oxide in the blood was also measured. Nitric oxide is the major metabolite responsible for maintaining healthy blood pressure.

Among the 48 study subjects, levels of nitric oxide in the blood more than doubled after 12 weeks of taking the supplements twice daily.

Blood Sugar Metabolism

During the study, the impact of the supplements on blood sugar levels was evaluated after consumption of a bread roll. The results show a significant reduction in post prandial hyperglycemia as soon as subjects took the supplements for the first time, with an increasingly greater reduction after several weeks of continual use of the supplements.

Indeed, the sugar spike was reduced by 27.4% the first day, 37.2% after 6 weeks, and 44.3% after 12 weeks of using the supplements.

A much healthier insulin response was also observed, especially among subjects who had preliminary signs of insulin resistance but were not diabetic.

Among this group, after 12 weeks of use we observed a significant 28% drop in the HOMA index, which is a measure of insulin sensitivity.

FIG. 1 provides graph comparisons of the control and test groups (i.e., the healthy and metabolic groups) showing HOMA, HbA1c, and postprandial plasma glucose levels after one dose, 6 weeks, and 12 weeks.

Heart Rate and Energy

As subjects continued taking the nutrients in the supplements over time, the body's ability to efficiently produce energy appeared to significantly increase. Part of the study was to take the pulse of the 48 subjects after exercising on an elliptical machine at a specific rate of revolutions per minute. The subjects were each tested before they had consumed the supplements, and tested again one hour after taking the supplements, and then again after six weeks, and after 12 weeks of continued use of the supplements. After six weeks of using the supplements the 48 subjects had an average heart rate of eight fewer beats per minute than they had doing exactly the same exercise prior to taking the supplements.

|  | HEALTHY | | | METABOLIC | | |
| --- | --- | --- | --- | --- | --- | --- |
|  | Control | 6 Weeks | 12 Weeks | Control | 6 Weeks | 12 Weeks |
| Total Cholesterol | 191.6 ± 6.8 | 184.2 ± 6.7* | 185.2 ± 6.5 | 233.3 ± 6.8 | 208.7 ± 6.4* | 207.8 ± 6.0* |
| Triglycerides | 88.4 ± 8.3 | 85.5 ± 5.5 | 84.7 ± 5.9 | 141.4 ± 12.0 | 120.8 ± 9.6* | 104.0 ± 7.7* |
| LDL-C | 116.4 ± 6.1 | 109.8 ± 5.4* | 107.3 ± 5.3* | 140.5 ± 8.1 | 130.9 ± 5.5* | 130.3 ± 5.5* |
| HDL-C | 62.3 ± 3.8 | 66.0 ± 3.5 | 68.7 ± 3.0* | 65.8 ± 4.0 | 70.0 ± 3.2* | 69.3 ± 4.6* |
| VLDL-C | 11.6 ± 1.3 | 7.7 ± 0.8* | 8.4 ± 1.0* | 18.3 ± 2.4 | 14.4 ± 1.6* | 9.4 ± 0.9* |
| TC/HDL | 3.3 ± 0.2 | 2.9 ± 0.1* | 2.8 ± 0.1* | 3.9 ± 0.2 | 3.1 ± 0.2* | 3.3 ± 0.2* |

Triglycerides

An average of an 8.8% drop in triglycerides was recorded among the total population of 48 subjects.

But this drop was notably greater for people with normal but slightly elevated triglycerides. This group recorded an average decrease in triglycerides of 23.3%.

After 12 weeks of taking the supplements, the subjects were observed being able to conduct the same exercise with a pulse of nine fewer beats per minute.

Figure 2:
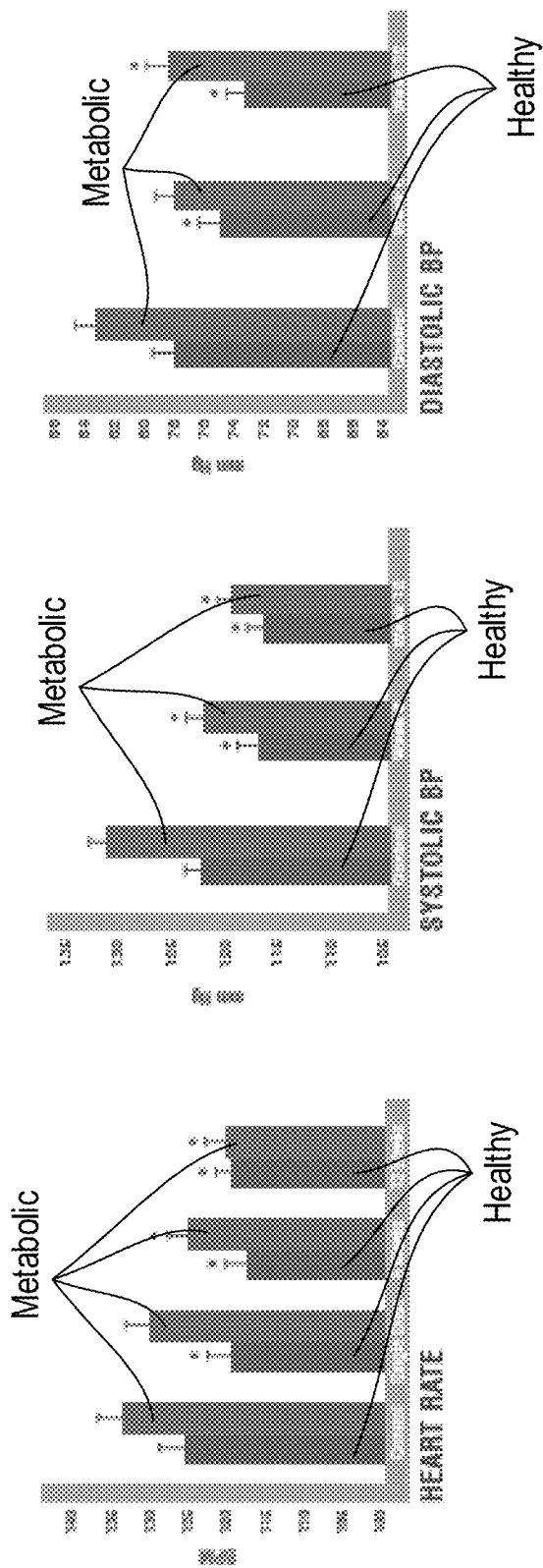
FIG. 2 provides bar graph comparing control and test groups (i.e., the healthy (left bar) and metabolic (right bar) groups) showing heart rate, systolic blood pressure, and diastolic blood pressure after one dose, 6 weeks, and 12 weeks.

FIG. 2 provides graph comparisons of the control and test groups (i.e., the healthy and metabolic groups) showing heart rate, systolic blood pressure, and diastolic blood pressure after one dose, 6 weeks, and 12 weeks.

Free Radical Reduction

The amount of free radicals in the blood during rest and then during exercise was tested in the subjects. Again, the results were unexpected. In the research, free radicals were measured as Reactive Oxygen Species, or ROS.

After six weeks of using the supplements, the 48 subjects recorded an average of a 22.07% reduction in ROS while resting and a 25.9% reduction in ROS during exercise.

Such a reduction in ROS from simple nutritional supplements was unexpected.

Figure 3:
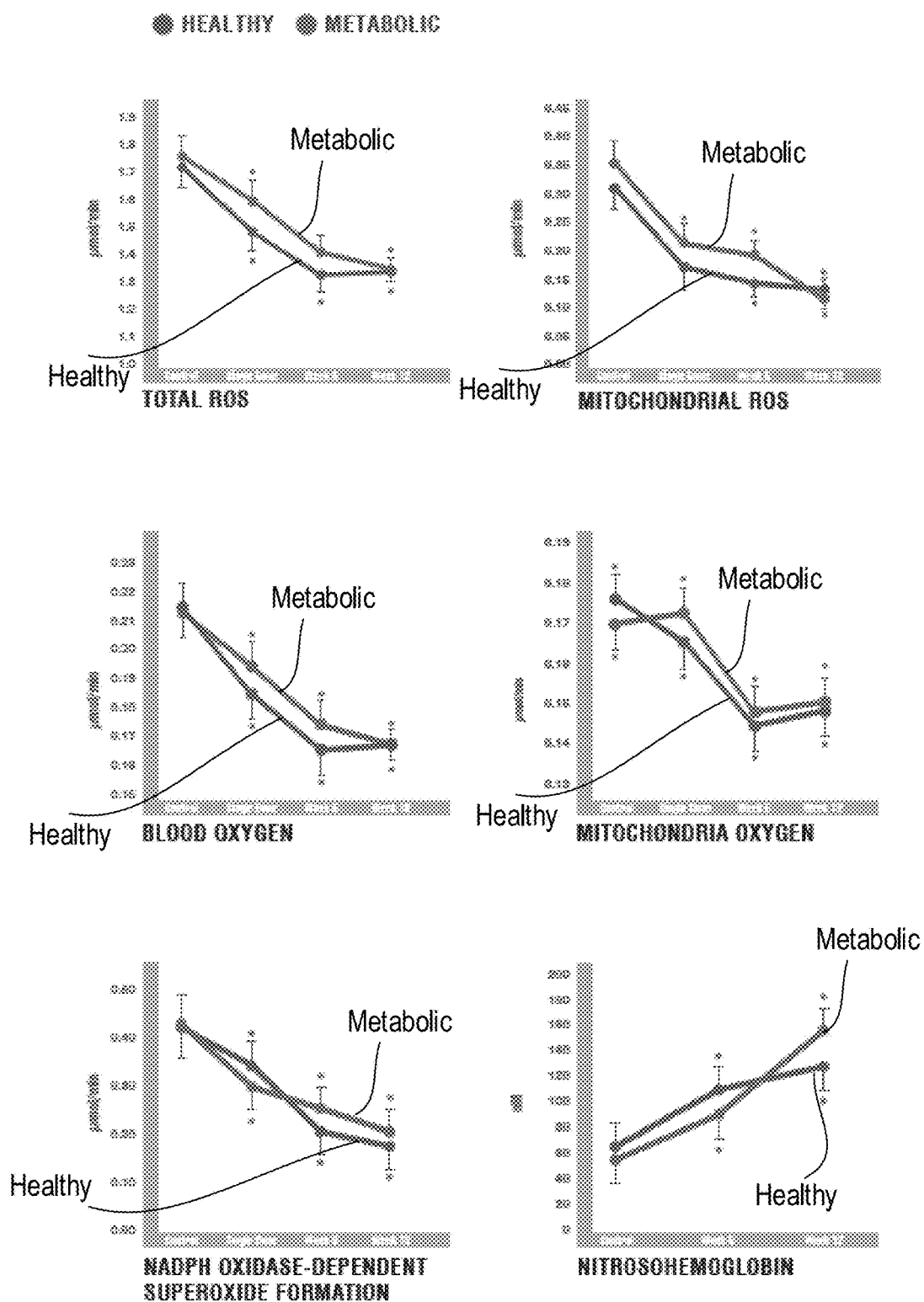
FIG. 3 provides bar graphs comparing control and test groups (i.e., healthy (left bar) and metabolic (right bar) groups, respectively) showing total ROS, mitochondrial ROS, blood oxygen levels, mitochondria oxygen levels, NADPH oxidase-dependent superoxide formation, and nitrosohemoglobin levels.

FIG. 3 provides comparison graphs of the control and test groups (i.e., the healthy and metabolic groups) showing total ROS, mitochondrial ROS, blood oxygen levels, mitochondria oxygen levels, NADPH oxidase-dependent superoxide formation, and nitrosohemoglobin levels. Both test groups show decreased initial and TNF-activated levels when compared to the control group after one dose, 6 weeks, and 12 weeks.

Figure 4:
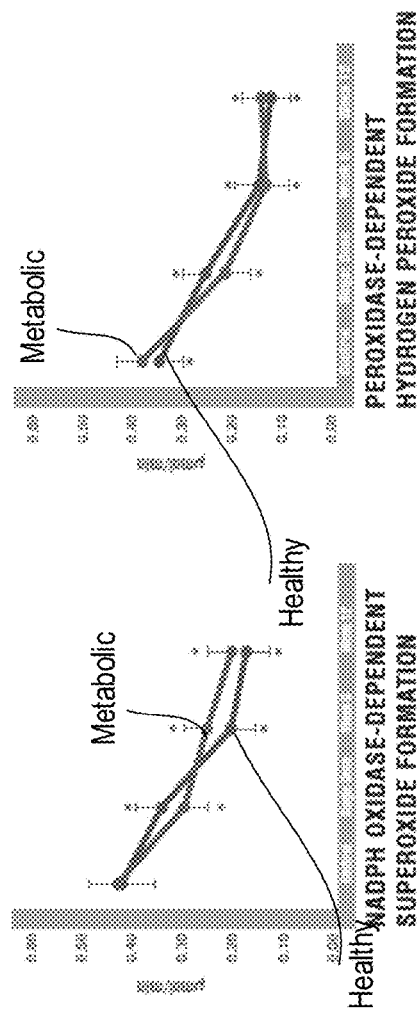
FIG. 4 provides line graphs comparing control and test groups (i.e., healthy (darker line) and metabolic (lighter line) groups, respectively) showing NADPH oxidase-dependent superoxide formation, peroxidase-dependent hydrogen peroxide formation, stress heart rate, and circulating nitric oxide levels after one dose, 6 weeks, and 12 weeks.
Figure 4:
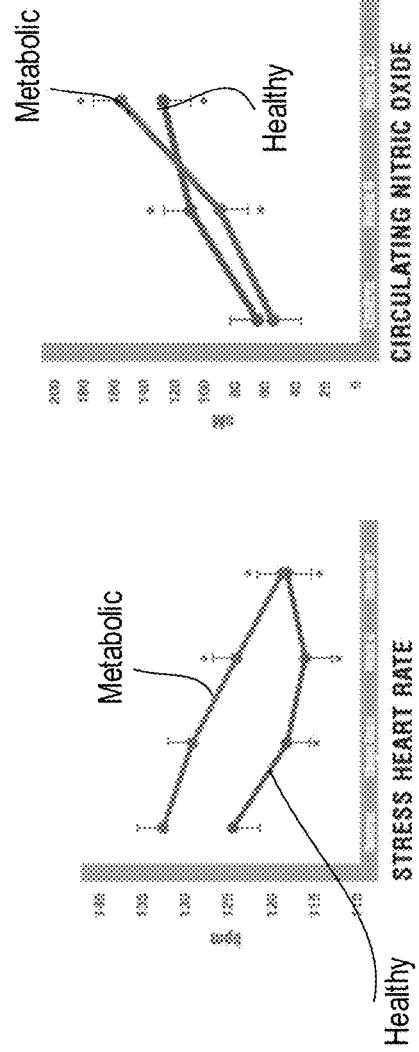

FIG. 4 provides graph comparisons of the control and test groups (i.e., the healthy and metabolic groups) showing NADPH oxidase-dependent superoxide formation, peroxidase-dependent hydrogen peroxide formation, stress heart rate and circulating nitric oxide levels after one dose, 6 weeks, and 12 weeks.

Inflammation Resistance

Unexpected results in inflammation response were observed for the 48 study subjects.

In the first inflammation test, resistance to inflammation improved an average of 35.8% in one hour following administration of the supplements.

The second test measured high-sensitivity C-reactive protein, also known as hs-CRP.

CRP readings of 3.0 mg/L or higher, although still considered within the normal range, can potentially increase a person's risk of heart disease. The risk seems even greater in women than in men. By contrast, people with extremely low levels of CRP, less than 0.5 mg/L, do not often have heart attacks.

After 12 weeks of regular supplementation with the multi-supplement composition of Example 3, subjects showed a significant 21.3% reduction in hs-CRP.

Subjects who had higher hs-CRP, but still within normal range, recorded a striking 34.1% reduction in hs-CRP after 12 weeks of consistently taking the multi-supplement composition of Example 5a.

Generally, the average of hs-CRP among these participants moved from a normal but elevated range to the much more healthy and moderate range.

Figure 5:
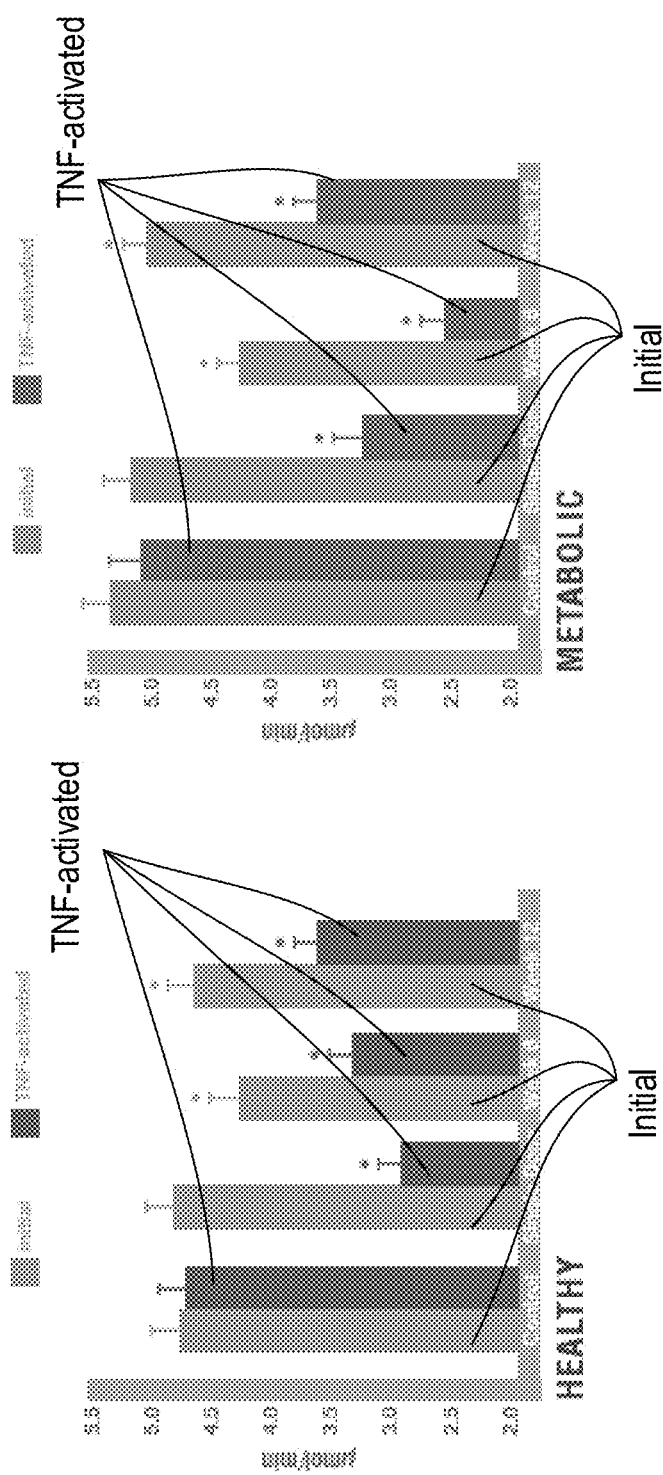
FIG. 5 provides bar graphs comparing control and test groups (i.e., healthy and metabolic groups, respectively) following inducement of inflammation. Both test groups show decreased initial (left bar) and TNF-activated (right bar) levels when compared to the control group after one dose, 6 weeks, and 12 weeks.
Figure 6:
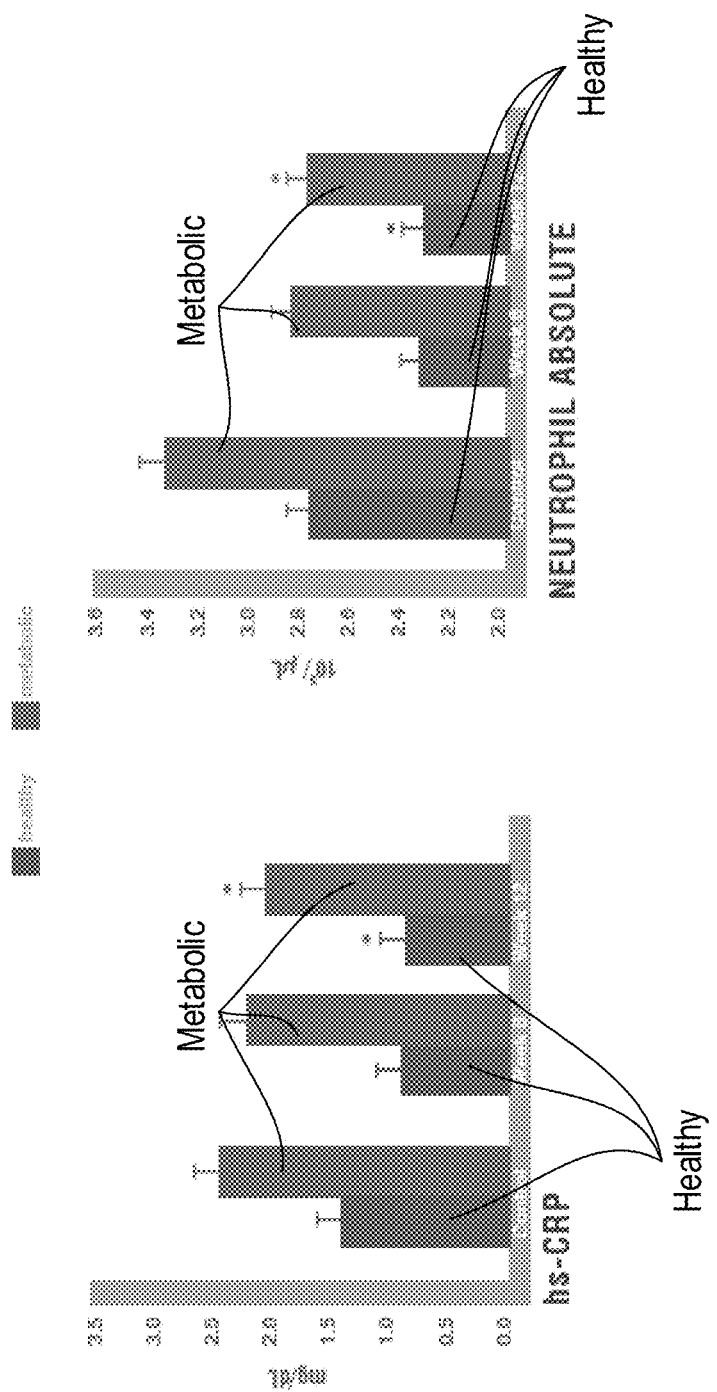
FIG. 6 provides the hs-CRP and neutrophil (absolute) values of control and test groups (i.e., healthy (left bar) and metabolic (right bar) groups, respectively) after one dose, 6 weeks, and 12 weeks.

Induce inflammation results of control and test groups (i.e., the healthy and metabolic groups) are shown in FIG. 5. Both test groups show decreased initial and TNF-activated levels when compared to the control group after one dose, 6 weeks, and 12 weeks. FIG. 6 provides the hs-CRP and neutrophil (absolute) values of the control and test groups (i.e., the healthy and metabolic groups) after one dose, 6 weeks, and 12 weeks.

Summary

In summary, a controlled, long-term study in healthy and metabolic syndrome volunteers show that the formulated complex nutritional supplement of Example 5a can inhibit both oxidative stress and inflammatory response. After six and 12 weeks of using twice daily the multi-supplement composition of Example 5a, the 48 test subjects on average improved significantly in every marker measured. Those with normal but elevated markers improved to an even greater extent. The study has demonstrated the anti-inflammatory and antioxidant capabilities of complex supplements. The regulation of enzyme expression, formation of secondary biologically active compounds and second messenger molecules, which are independent of NADPH oxidase and peroxidases function and polymorphism, were shown.

Inflammation may contribute to the pathogenesis of multiple cardiovascular and metabolic disorders over p22phox-based NADPH oxidases and peroxidases existing in the vessel wall. The p22phox-based NADPH oxidases and peroxidases may act as important superoxide and H2O2 generating systems, modulating an inflammatory response and oxidative stress.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A multi-supplement composition comprising:
   (a) a dietary supplement of a Supplement Formulation A comprising:
      (i) from about 5 billion to about 15 billion cfu of a mixture of *Lactobacillus acidophilus, Lactobacillus plantarum, Lactobacillus casei, Lactobacillus rhamnosus*, and *Bifidobacterium lactis*,
      (ii) a filler having a water activity less than 0.2, and
      (iii) fructooligosaccharides,
   wherein said dietary supplement of Supplement Formulation A is in the form of a capsule that releases said *Lactobacillus acidophilus, Lactobacillus plantarum, Lactobacillus casei, Lactobacillus rhamnosus*, and *Bifidobacterium lactis*, within an intestine of a mammal following oral administration to said mammal;
   (b) a dietary supplement of a Supplement Formulation B comprising:
      (i) a fat-soluble antioxidant,
      (ii) a phenolic compound, and
      (iii) a water soluble antioxidant;
   (c) a dietary supplement of a Supplement Formulation C comprising:
      (i) an iridoid,
      (ii) a ginger component,
      (iii) an anthocyanin, and
      (iv) at least one agent selected from the group consisting of a coumarin, a curcuminoid, and a green tea extract;
   (d) a dietary supplement of a Supplement Formulation E comprising:
      (i) a grape seed extract, and
      (ii) an enzyme selected from the group consisting of a fungal protease, an acid stable protease, and bromelain; and
   (e) a dietary supplement of a Supplement Formulation F consisting essentially of one or more mineral-amino acid compound/polysaccharide complexes, wherein each of said one or more mineral-amino acid/polysaccharide complexes comprises one or more mineral-amino acid compounds conjugated to one or more polysaccharides.

2. The composition of claim 1, further comprising a dietary supplement of a Supplement Formulation G comprising:
    (i) huperzine A,
    (ii) acetyl-L-carnitine,
    (iii) a *Bacopa monnieri* extract, and
    (iv) curcumin.

3. The composition of claim 1, further comprising a dietary supplement of a Supplement Formulation H comprising phosphatidylserine.

4. The composition of claim 3, wherein Supplement Formulation H further comprises:
    (i) DHA,
    (ii) EPA,
    (iii) an antioxidant, and
    (iv) *Ginkgo biloba*.

5. The composition of claim 1, further comprising a dietary supplement of a Supplement Formulation D comprising fish oil.

6. The composition of claim 1, further comprising a dietary supplement of a Supplement Formulation I comprising Vitamin $K_2$ and Vitamin $D_3$.

7. The composition of claim 1, further comprising a dietary supplement of a Supplement Formulation J comprising CoQ10, a tocotrienol, and alpha-lipoic acid.

8. The composition of claim 1, further comprising a dietary supplement of a Supplement Formulation K comprising:
    (i) a sterol compound, and
    (ii) omega 3 fatty acids.

9. The composition of claim 1, further comprising a dietary supplement of a Supplement Formulation L comprising calcium.

10. The composition of claim 1, further comprising a dietary supplement of a Supplement Formulation M that comprises glucosamine hydrochloride.

11. The composition of claim 10, wherein Supplement Formulation M further comprises chondroitin sulfate and methyl sulfonyl methane.

12. The composition of claim 1, further comprising a dietary supplement of a Supplement Formulation N comprising a green coffee bean extract, a green tea phytosome, a green tea extract, and a red pepper extract.

13. The composition of claim 1, wherein the mineral-amino acid compound/polysaccharide complex is prepared by heating a composition comprising water, one or more mineral-amino acid compounds, and one or more polysaccharides at a temperature from about 100° F. to about 180° F.

14. The composition of claim 1, wherein the mineral-amino acid compound/polysaccharide complex has a ratio of mineral-amino acid compound to polysaccharide of from about 5:1 to about 1:1.

15. The composition of claim 5, wherein the composition results in an average reduction of heart rate of at least 5 bpm in a subject after the subject performs an exercise within one hour of administration to the subject as compared to a heart rate of the subject after performing the exercise without administration of the composition.

16. The composition of claim 5, wherein the composition results in at least a 21% reduction in hs-CRP in a subject after administration of the composition to the subject for at least 12 weeks.

17. The composition of claim 5, wherein the composition results in an average reduction in resting ROS during rest of at least 22% after administration of the composition to the subject for at least 6 weeks.

18. The composition of claim 5, wherein the composition results in an average reduction in ROS during exercise of at least 25% after administration of the composition to the subject for at least 6 weeks.

19. A multi-supplement composition comprising:
    a dietary supplement of a Supplement Formulation A comprising:
        (i) from about 5 billion to about 15 billion cfu of a mixture of *Lactobacillus acidophilus*, *Lactobacillus plantarum*, *Lactobacillus casei*, *Lactobacillus rhamnosus*, and *Bifidobacterium lactis*,
        (ii) a filler having a water activity less than 0.2, and
        (iii) fructooligosaccharides,
    wherein said dietary supplement of Supplement Formulation A is in the form of a capsule that releases said *Lactobacillus acidophilus*, *Lactobacillus plantarum*, *Lactobacillus casei*, *Lactobacillus rhamnosus*, and *Bifidobacterium lactis*, within an intestine of a mammal following oral administration to said mammal;
    a dietary supplement of a Supplement Formulation B comprising:
        150-600 mg Vitamin C,
        25-100 mg α-tocopherol,
        0.05-0.2 mg α-carotene,
        1-4 mg β-carotene,
        0.1-0.4 mg criptoxanthin,
        0.05-0.2 mg zeaxanthin,
        0.05-0.2 mg lutein,
        1.5-6 mg lycopene,
        3.5-13 mg β-tocopherol,
        12-50 mg δ-tocopherol,
        50-200 mg γ-tocopherol,
        75-300 mg olive fruit extract, and
        12-50 mg grape seed extract;
    a dietary supplement of a Supplement Formulation C comprising 100-1000 mg of a combination of Devil's Claw Extract, Ginger Root Extract, Chokeberry Extract, Green Tea Leaf Extract, *Angelica gigas* Root Extract, and Turmeric Root Extract;
    a dietary supplement of a Supplement Formulation D comprising 1000-5000 mg fish oil concentrate;
    a dietary supplement of a Supplement Formulation E comprising:
        100-1000 HUT fungal protease,
        20-200 mg quercetin,
        0.1-200 mg Bilberry extract, and
        0.1-100 mg *Ginkgo biloba* Leaf Extract; and
    a dietary supplement of a Supplement Formulation F comprising:
        200-1000 mg calcium, at least a portion of which is present as calcium amino acid oligofructose complex,
        0-18 mg iron, at least a portion of which is present as iron amino acid oligofructose complex,
        100-300 mcg iodine, at least a portion of which is present as iodine amino acid oligofructose complex,
        100-400 mg magnesium, at least a portion of which is present as magnesium amino acid oligofructose complex,
        5-30 mg zinc, at least a portion of which is present as zinc amino acid oligofructose complex,
        35-150 mcg selenium, at least a portion of which is present as selenium amino acid oligofructose complex,
        1-5 mg copper, at least a portion of which is present as copper amino acid oligofructose complex, 1-5 mg manganese, at least a portion of which is present as manganese amino acid oligofructose complex, 60-360 mcg chromium, at least a portion of which is present as chromium amino acid oligofructose complex, 50-150 mcg molybdenum, at least a portion of which is present as molybdenum amino acid oligofructose complex, and 0-300 mcg boron, at least a portion of which is present as boron amino acid oligofructose complex.

20. A multi-supplement composition comprising:

a dietary supplement of a Supplement Formulation A comprising:
  (i) from about 5 billion to about 15 billion cfu of a mixture of *Lactobacillus acidophilus, Lactobacillus plantarum, Lactobacillus casei, Lactobacillus rhamnosus*, and *Bifidobacterium lactis*,
  (ii) a filler having a water activity less than 0.2, and
  (iii) fructooligosaccharides, wherein said dietary supplement of Supplement Formulation A is in the form of a capsule that releases said *Lactobacillus acidophilus, Lactobacillus plantarum, Lactobacillus casei, Lactobacillus rhamnosus*, and *Bifidobacterium lactis*, within an intestine of a mammal following oral administration to said mammal;

a dietary supplement of a Supplement Formulation B comprising:
  2500 IU Vitamin A,
  300 mg Vitamin C,
  60 IU Vitamin E,
  1000 mcg carotenoids,
  32 mg of a combination of β-tocopherol, δ-tocopherol, and γ-tocopherol,
  150 mg olive fruit extract, and
  25 mg grape seed extract;

a dietary supplement of a Supplement Formulation C comprising 605 mg of a combination of Devil's Claw Extract, Ginger Root Extract, Chokeberry Extract, Green Tea Leaf Extract, *Angelica Gigas* Root Extract, and Turmeric Root Extract;

a dietary supplement of a Supplement Formulation D comprising 2000 mg fish oil concentrate;

a dietary supplement of a Supplement Formulation E comprising:
  330 mg of a combination of grape seed and grape skin extracts, and
  60 mg of a combination of bromelain, fungal protease, quercetin, Bilberry extract, and *Ginkgo biloba* Leaf Extract; and a dietary supplement of a Supplement Formulation F comprising:
  250 mg calcium, at least a portion of which is present as calcium amino acid oligofructose complex,
  150 mcg iodine, at least a portion of which is present as iodine amino acid oligofructose complex,
  200 mg magnesium, at least a portion of which is present as magnesium amino acid oligofructose complex,
  15 mg zinc, at least a portion of which is present as zinc amino acid oligofructose complex,
  105 mcg selenium, at least a portion of which is present as selenium amino acid oligofructose complex,
  3 mg copper, at least a portion of which is present as copper amino acid oligofructose complex,
  120-180 mcg chromium, at least a portion of which is present as chromium amino acid oligofructose complex,
  75-90 mcg molybdenum, at least a portion of which is present as molybdenum amino acid oligofructose complex, and
  150 mcg boron, at least a portion of which is present as boron amino acid oligofructose complex.

21. The composition of claim 1, wherein said Supplement Formulation A has a water activity of about 0.1 to about 0.2.

22. The composition of claim 1, wherein said Supplement Formulation A comprises about 3.5 wt % to about 5.0 wt % fructooligosaccharides.

23. The composition of claim 1, wherein said Supplement Formulation A comprises about 1 mg and about 50 mg fructooligosaccharides per every gram of the composition.

24. The composition of claim 1, wherein said dietary supplement of Supplement Formulation A has a water activity of about 0.125 to about 0.171.

* * * * *